US010285853B2

(12) United States Patent
Rangel-Friedman et al.

(10) Patent No.: US 10,285,853 B2
(45) Date of Patent: May 14, 2019

(54) SYSTEMS AND METHODS FOR DELIVERING AN OCULAR IMPLANT TO THE SUPRACHOROIDAL SPACE WITHIN AN EYE

(71) Applicant: GLAUKOS CORPORATION, Laguna Hills, CA (US)

(72) Inventors: Gary Rangel-Friedman, Laguna Niguel, CA (US); David S. Haffner, Mission Viejo, CA (US)

(73) Assignee: Glaukos Corporation, San Clemente, CA (US)

( * ) Notice: Subject to any disclaimer, the term of this patent is extended or adjusted under 35 U.S.C. 154(b) by 440 days.

(21) Appl. No.: 14/776,563

(22) PCT Filed: Mar. 12, 2014

(86) PCT No.: PCT/US2014/024889
§ 371 (c)(1),
(2) Date: Sep. 14, 2015

(87) PCT Pub. No.: WO2014/151070
PCT Pub. Date: Sep. 25, 2014

(65) Prior Publication Data
US 2016/0038338 A1 Feb. 11, 2016

Related U.S. Application Data

(60) Provisional application No. 61/790,759, filed on Mar. 15, 2013.

(51) Int. Cl.
*A61F 9/00* (2006.01)
*A61F 9/007* (2006.01)

(52) U.S. Cl.
CPC ........ *A61F 9/0017* (2013.01); *A61F 9/00781* (2013.01)

(58) Field of Classification Search
CPC .................... A61F 9/0017; A61F 9/00781
See application file for complete search history.

(56) References Cited

U.S. PATENT DOCUMENTS

| 2,031,754 | A | 2/1936 | Mills |
| 2,127,903 | A | 8/1938 | Bowen |

(Continued)

FOREIGN PATENT DOCUMENTS

| AU | 200072059 A1 | 7/2001 |
| CA | 2244646 A1 | 2/1999 |

(Continued)

OTHER PUBLICATIONS

Chu, Jennifer, "Detecting the Danger Signs of Glaucoma", Technology Review Published by MIT, Aug. 15, 2007, 2 pp., http://www.technologyreview.com/printer_friendly_article.aspx?id=19257.

(Continued)

*Primary Examiner* — Benjamin J Klein
(74) *Attorney, Agent, or Firm* — Knobbe Martens Olson & Bear LLP

(57) ABSTRACT

Delivery devices, systems and methods are provided for inserting an implant into an eye. The delivery or inserter devices or systems can be used to dispose or implant an ocular stent or implant, such as a shunt, in communication with a suprachoroidal space of the eye. The implant can drain fluid from an anterior chamber of the eye to a physiologic outflow path of the eye, such as, the suprachoroidal space or other portion of the uveoscleral outflow path. The delivery or inserter devices or systems can be used in conjunction with other ocular surgery, for example, but not limited to, cataract surgery-through a preformed corneal incision, or independently with the inserter configured to make a corneal incision. The implant can be preloaded with (Continued)

or within the inserter to advantageously provide a sterile, easy-to-use package for use by an operator.

25 Claims, 29 Drawing Sheets

(56) References Cited

U.S. PATENT DOCUMENTS

| | | |
|---|---|---|
| 2,269,963 A | 1/1942 | Frederick |
| 3,439,675 A | 4/1969 | Cohen |
| 3,717,151 A | 2/1973 | Collett |
| 3,809,093 A | 5/1974 | Abraham |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Aklyama |
| 3,948,871 A | 4/1976 | Butterfield et al. |
| 3,976,077 A | 8/1976 | Kerfoot, Jr. |
| 4,030,480 A | 6/1977 | Meyer |
| 4,043,346 A | 8/1977 | Mobley et al. |
| 4,113,088 A | 9/1978 | Binkhorst |
| 4,168,697 A | 9/1979 | Cantekin |
| 4,175,563 A | 11/1979 | Arenberg et al. |
| 4,299,227 A | 11/1981 | Lincoff |
| 4,328,803 A | 5/1982 | Pape |
| 4,366,582 A | 1/1983 | Faulkner |
| 4,402,681 A | 9/1983 | Haas et al. |
| 4,449,529 A | 5/1984 | Burns et al. |
| 4,449,974 A | 5/1984 | Messingschlager |
| 4,501,274 A | 2/1985 | Skjaerpe |
| 4,521,210 A | 6/1985 | Wong |
| 4,560,383 A | 12/1985 | Leiske |
| 4,578,058 A | 3/1986 | Grandon |
| 4,632,842 A | 12/1986 | Karwoski et al. |
| 4,634,418 A | 1/1987 | Binder |
| 4,642,090 A | 2/1987 | Ultrata |
| 4,692,142 A | 9/1987 | Dignam et al. |
| 4,718,907 A | 1/1988 | Karwoski et al. |
| 4,733,665 A | 3/1988 | Palmaz |
| 4,782,819 A | 11/1988 | Adair |
| 4,800,870 A | 1/1989 | Reid, Jr. |
| 4,800,890 A | 1/1989 | Cramer |
| 4,804,382 A | 2/1989 | Turina et al. |
| 4,820,626 A | 4/1989 | Williams et al. |
| 4,846,172 A | 7/1989 | Berlin |
| 4,846,793 A | 7/1989 | Leonard et al. |
| 4,867,173 A | 9/1989 | Leoni |
| 4,870,953 A | 10/1989 | DonMicheal et al. |
| 4,886,488 A | 12/1989 | White |
| 4,900,300 A | 2/1990 | Lee |
| 4,905,667 A | 3/1990 | Foerster et al. |
| 4,986,810 A | 1/1991 | Semrad |
| 4,991,602 A | 2/1991 | Amplatz et al. |
| 5,005,577 A | 4/1991 | Frenekl |
| 5,053,040 A | 10/1991 | Goldsmith, III |
| 5,053,044 A | 10/1991 | Mueller et al. |
| 5,095,887 A | 3/1992 | Leon et al. |
| 5,116,327 A | 5/1992 | Seder et al. |
| 5,129,895 A | 7/1992 | Vassiliadis et al. |
| 5,139,502 A | 8/1992 | Berg et al. |
| 5,169,386 A | 12/1992 | Becker et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,248,231 A | 9/1993 | Denham et al. |
| 5,284,476 A | 2/1994 | Koch |
| 5,290,295 A | 3/1994 | Querals et al. |
| 5,318,513 A | 6/1994 | Leib et al. |
| 5,324,306 A | 6/1994 | Makower et al. |
| 5,334,137 A | 8/1994 | Freeman |
| 5,342,370 A | 8/1994 | Simon et al. |
| 5,358,492 A | 10/1994 | Feibus |
| 5,360,399 A | 11/1994 | Stegmann |
| 5,415,666 A | 5/1995 | Gourlay et al. |
| 5,443,505 A | 8/1995 | Wong et al. |
| 5,445,637 A | 8/1995 | Bretton |
| 5,462,558 A | 10/1995 | Kolesa et al. |
| 5,472,440 A | 12/1995 | Beckman |
| 5,486,165 A | 1/1996 | Stegmann |
| 5,556,400 A | 9/1996 | Tunis |
| 5,558,637 A | 9/1996 | Allonen et al. |
| 5,562,641 A | 10/1996 | Flomenblit et al. |
| 5,601,094 A | 2/1997 | Reiss |
| 5,626,588 A | 5/1997 | Sauer et al. |
| 5,639,278 A | 6/1997 | Dereume et al. |
| 5,643,321 A | 7/1997 | McDevitt |
| 5,651,782 A | 7/1997 | Simon et al. |
| 5,651,783 A | 7/1997 | Reynard |
| 5,653,724 A | 8/1997 | Imonti |
| 5,669,501 A | 9/1997 | Hissong et al. |
| 5,676,679 A | 10/1997 | Simon et al. |
| 5,681,275 A | 10/1997 | Ahmed |
| 5,681,323 A | 10/1997 | Arick |
| 5,695,479 A | 12/1997 | Jagpal |
| 5,702,414 A | 12/1997 | Richter et al. |
| 5,702,419 A | 12/1997 | Berry et al. |
| 5,723,005 A | 3/1998 | Herrick |
| 5,725,529 A | 3/1998 | Nicholson et al. |
| 5,725,546 A | 3/1998 | Samson |
| 5,733,256 A | 3/1998 | Costin |
| 5,741,292 A | 4/1998 | Mendius |
| 5,741,333 A | 4/1998 | Frid |
| 5,762,625 A | 6/1998 | Igaki |
| 5,766,243 A | 6/1998 | Christensen et al. |
| 5,785,674 A | 7/1998 | Mateen |
| 5,792,099 A | 8/1998 | DeCamp et al. |
| 5,800,376 A | 9/1998 | Vaskelis |
| 5,807,244 A | 9/1998 | Barot |
| 5,810,870 A | 9/1998 | Myers et al. |
| 5,817,100 A | 10/1998 | Igaki |
| 5,824,071 A | 10/1998 | Nelson et al. |
| 5,830,171 A | 11/1998 | Wallace |
| 5,833,694 A | 11/1998 | Poncet |
| 5,836,939 A | 11/1998 | Negus et al. |
| 5,846,199 A | 12/1998 | Hijlkema et al. |
| 5,865,831 A | 2/1999 | Cozean et al. |
| 5,868,697 A | 2/1999 | Richter et al. |
| 5,891,084 A | 4/1999 | Lee |
| 5,893,837 A | 4/1999 | Eagles et al. |
| 5,908,449 A | 6/1999 | Bruchman et al. |
| 5,913,852 A | 6/1999 | Magram |
| 5,927,585 A | 7/1999 | Moorman et al. |
| 5,932,299 A | 8/1999 | Katoot |
| 5,941,250 A | 8/1999 | Aramant et al. |
| 5,984,913 A | 11/1999 | Kritzinger et al. |
| 6,004,302 A | 12/1999 | Brierley |
| 6,007,511 A | 12/1999 | Prywes |
| 6,030,416 A | 2/2000 | Huo et al. |
| 6,033,434 A | 3/2000 | Borghi |
| 6,036,678 A | 3/2000 | Giungo |
| 6,036,682 A | 3/2000 | Lange et al. |
| 6,045,557 A | 4/2000 | White et al. |
| 6,050,999 A | 4/2000 | Paraschac et al. |
| 6,071,286 A | 6/2000 | Mawad |
| 6,074,395 A | 6/2000 | Trott et al. |
| 6,077,299 A | 6/2000 | Adelberg et al. |
| 6,135,977 A | 10/2000 | Drasler et al. |
| 6,142,990 A | 11/2000 | Burk |
| 6,146,387 A | 11/2000 | Trott et al. |
| 6,165,210 A | 12/2000 | Lau et al. |
| 6,174,305 B1 | 1/2001 | Mikus et al. |
| 6,186,974 B1 | 2/2001 | Allan et al. |
| 6,187,016 B1 | 2/2001 | Hedges et al. |
| 6,221,078 B1 | 4/2001 | Bylsma |
| 6,224,570 B1 | 5/2001 | Le et al. |
| 6,231,597 B1 | 5/2001 | Deem et al. |
| 6,241,721 B1 | 6/2001 | Cozean et al. |
| 6,254,612 B1 | 7/2001 | Hieshima |
| 6,264,668 B1 | 7/2001 | Prywes |
| 6,287,313 B1 | 9/2001 | Sasso |
| 6,299,603 B1 | 10/2001 | Hecker et al. |
| 6,306,114 B1 | 10/2001 | Freeman et al. |
| 6,342,058 B1 | 1/2002 | Portney |

(56) References Cited

U.S. PATENT DOCUMENTS

| | | |
|---|---|---|
| 6,355,033 B1 | 3/2002 | Moorman et al. |
| 6,358,222 B1 | 3/2002 | Grundei |
| 6,361,519 B1 | 3/2002 | Knudson et al. |
| 6,363,938 B2 | 4/2002 | Saadat et al. |
| 6,375,642 B1 | 4/2002 | Grieshaber et al. |
| 6,402,734 B1 | 6/2002 | Weiss |
| 6,405,732 B1 | 6/2002 | Edwards et al. |
| 6,428,501 B1 | 8/2002 | Reynard |
| 6,428,566 B1 | 8/2002 | Holt |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,517,483 B2 | 2/2003 | Park et al. |
| 6,530,896 B1 | 3/2003 | Elliott |
| 6,544,249 B1 | 4/2003 | Yu et al. |
| 6,561,974 B1 | 5/2003 | Grieshaber et al. |
| 6,582,426 B2 | 6/2003 | Moorman et al. |
| 6,582,453 B1 | 6/2003 | Tran et al. |
| 6,585,680 B2 | 7/2003 | Bugge |
| 6,585,753 B2 | 7/2003 | Eder et al. |
| 6,589,198 B1 | 7/2003 | Soltanpour et al. |
| 6,589,203 B1 | 7/2003 | Mitrev |
| 6,605,053 B1 | 8/2003 | Kamm et al. |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,629,981 B2 | 10/2003 | Bui et al. |
| 6,638,239 B1 | 10/2003 | Bergheim et al. |
| 6,676,607 B2 | 1/2004 | De Juan, Jr. et al. |
| 6,682,500 B2 | 1/2004 | Soltanpour et al. |
| 6,699,272 B2 | 3/2004 | Slepian et al. |
| D490,152 S | 5/2004 | Myall et al. |
| 6,763,833 B1 | 7/2004 | Khera et al. |
| 6,764,439 B2 | 7/2004 | Schaaf et al. |
| 6,767,346 B2 | 7/2004 | Damasco et al. |
| 6,780,165 B2 | 8/2004 | Kadziauskas et al. |
| 6,827,738 B2 | 12/2004 | Willis et al. |
| 6,893,413 B2 | 5/2005 | Martin |
| 6,902,577 B2 | 6/2005 | Lipshitz et al. |
| 6,955,656 B2 | 10/2005 | Bergheim et al. |
| 6,966,888 B2 | 11/2005 | Cullen et al. |
| 7,077,821 B2 | 7/2006 | Durgin |
| 7,077,848 B1 | 7/2006 | de Juan et al. |
| 7,090,681 B2 | 8/2006 | Weber et al. |
| 7,101,402 B2 | 9/2006 | Phelps et al. |
| 7,135,009 B2 | 11/2006 | Tu et al. |
| 7,135,016 B1 | 11/2006 | Asia et al. |
| 7,144,616 B1 | 12/2006 | Unger et al. |
| 7,163,543 B2 | 1/2007 | Smedley et al. |
| 7,186,232 B1 | 3/2007 | Smedley et al. |
| 7,192,484 B2 | 3/2007 | Chappa et al. |
| 7,217,263 B2 | 5/2007 | Humayun et al. |
| 7,273,475 B2 | 9/2007 | Tu et al. |
| 7,294,115 B1 | 11/2007 | Wilk |
| 7,297,130 B2 | 11/2007 | Bergheim et al. |
| 7,331,984 B2 | 2/2008 | Tu et al. |
| 7,344,528 B1 | 3/2008 | Tu et al. |
| 7,431,710 B2 | 10/2008 | Tu et al. |
| 7,468,065 B2 | 12/2008 | Weber et al. |
| 7,488,303 B1 | 2/2009 | Haffner et al. |
| 7,520,876 B2 | 4/2009 | Ressemann et al. |
| D592,746 S | 5/2009 | Highley et al. |
| RE40,722 E | 6/2009 | Chappa |
| 7,563,241 B2 | 7/2009 | Tu et al. |
| D606,190 S | 12/2009 | Pruitt et al. |
| 7,758,624 B2 | 7/2010 | Dorn et al. |
| 7,771,388 B2 | 8/2010 | Olsen et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,905,904 B2 | 3/2011 | Stone et al. |
| 7,931,660 B2 | 4/2011 | Aranyi et al. |
| 7,945,336 B2 | 5/2011 | Sauter-Starace et al. |
| 7,959,632 B2 | 6/2011 | Fugo |
| 7,967,772 B2 | 6/2011 | McKenzie et al. |
| 7,997,460 B2 | 8/2011 | Pardes et al. |
| 8,007,459 B2 | 8/2011 | Haffner et al. |
| 8,062,244 B2 | 11/2011 | Tu et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,197,418 B2 | 6/2012 | Lal et al. |
| 8,267,882 B2 | 9/2012 | Euteneuer et al. |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,506,515 B2 | 8/2013 | Burns et al. |
| 8,540,659 B2 | 9/2013 | Berlin |
| 8,579,846 B2 | 11/2013 | Tu et al. |
| 8,617,094 B2 | 12/2013 | Smedley et al. |
| 8,656,958 B2 | 2/2014 | Unger et al. |
| 8,679,089 B2 | 3/2014 | Berlin |
| 8,801,648 B2 | 8/2014 | Bergheim et al. |
| 8,808,219 B2 | 8/2014 | Bergheim et al. |
| 8,808,220 B2 | 8/2014 | Coroneo |
| 8,814,820 B2 | 8/2014 | Bergheim et al. |
| 8,852,137 B2 | 10/2014 | Horvath et al. |
| 8,852,266 B2 | 10/2014 | Brooks et al. |
| 8,998,983 B2 | 4/2015 | Auld |
| 9,173,775 B2 | 11/2015 | Haffner et al. |
| 9,220,632 B2 | 12/2015 | Smedley et al. |
| 9,301,875 B2 | 4/2016 | Tu et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,592,151 B2 | 3/2017 | Rangel-Friedman et al. |
| 9,597,230 B2 | 3/2017 | Haffner et al. |
| 9,603,741 B2 | 3/2017 | Berlin |
| 9,636,255 B2 | 5/2017 | Haffner et al. |
| 9,833,357 B2 | 12/2017 | Berlin |
| 9,849,027 B2 | 12/2017 | Highley et al. |
| 10,188,551 B2 | 1/2019 | Rangel-Friedman et al. |
| 2001/0000527 A1 | 4/2001 | Yaron et al. |
| 2001/0025150 A1 | 9/2001 | de Juan et al. |
| 2001/0053873 A1 | 12/2001 | Schaaf et al. |
| 2002/0052640 A1 | 5/2002 | Bigus et al. |
| 2002/0072673 A1 | 6/2002 | Yamamoto et al. |
| 2002/0099434 A1 | 7/2002 | Buscemi et al. |
| 2002/0111608 A1 | 8/2002 | Baerveldt et al. |
| 2002/0120284 A1 | 8/2002 | Schachar et al. |
| 2002/0120285 A1 | 8/2002 | Schachar et al. |
| 2002/0133168 A1 | 9/2002 | Smedley et al. |
| 2002/0143284 A1 | 10/2002 | Tu et al. |
| 2002/0165522 A1 | 11/2002 | Holmen |
| 2002/0177856 A1 | 11/2002 | Richter et al. |
| 2003/0014021 A1 | 1/2003 | Holmen |
| 2003/0014092 A1 | 1/2003 | Neuhann |
| 2003/0019833 A1 | 1/2003 | Unger et al. |
| 2003/0060752 A1 | 3/2003 | Bergheim et al. |
| 2003/0079329 A1 | 5/2003 | Yaron et al. |
| 2003/0093084 A1 | 5/2003 | Nissan et al. |
| 2003/0097117 A1 | 5/2003 | Buono |
| 2003/0097151 A1 | 5/2003 | Smedley et al. |
| 2003/0105456 A1 | 6/2003 | Lin |
| 2003/0109907 A1 | 6/2003 | Shadduck |
| 2003/0135149 A1 | 7/2003 | Cullen et al. |
| 2003/0139729 A1 | 7/2003 | Stegmann et al. |
| 2003/0195438 A1 | 10/2003 | Petillo |
| 2003/0208163 A1 | 11/2003 | Yaron et al. |
| 2003/0208217 A1 | 11/2003 | Dan |
| 2003/0212383 A1 | 11/2003 | Cote et al. |
| 2003/0236483 A1 | 12/2003 | Ren |
| 2004/0015140 A1 | 1/2004 | Shields |
| 2004/0088048 A1 | 5/2004 | Richter et al. |
| 2004/0098122 A1 | 5/2004 | Lee et al. |
| 2004/0102729 A1 | 5/2004 | Haffner et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0215126 A1 | 10/2004 | Ahmed |
| 2004/0225250 A1 | 11/2004 | Yablonski |
| 2004/0236343 A1 | 11/2004 | Taylor et al. |

(56) References Cited

U.S. PATENT DOCUMENTS

| | | |
|---|---|---|
| 2004/0243227 A1 | 12/2004 | Starksen et al. |
| 2004/0249404 A1 | 12/2004 | Haefliger |
| 2004/0254517 A1 | 12/2004 | Quiroz-Mercado et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2005/0038498 A1 | 2/2005 | Dubrow et al. |
| 2005/0055075 A1 | 3/2005 | Pinchuk et al. |
| 2005/0096639 A1 | 5/2005 | Slatkine et al. |
| 2005/0107734 A1 | 5/2005 | Coroneo |
| 2005/0125003 A1 | 6/2005 | Pinchuk et al. |
| 2005/0165385 A1 | 7/2005 | Simon |
| 2005/0171562 A1 | 8/2005 | Criscuolo et al. |
| 2005/0209549 A1 | 9/2005 | Bergheim et al. |
| 2005/0209672 A1 | 9/2005 | George et al. |
| 2005/0240143 A1 | 10/2005 | Dohlman |
| 2005/0240222 A1 | 10/2005 | Shipp |
| 2005/0267478 A1 | 12/2005 | Corradi et al. |
| 2005/0277864 A1 | 12/2005 | Haffner et al. |
| 2006/0032507 A1 | 2/2006 | Tu |
| 2006/0069340 A1 | 3/2006 | Simon |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0155238 A1 | 7/2006 | Shields |
| 2006/0155300 A1 | 7/2006 | Stamper et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0210605 A1 | 9/2006 | Chang et al. |
| 2006/0217741 A1 | 9/2006 | Ghannoum |
| 2006/0241580 A1 | 10/2006 | Mittelstein et al. |
| 2006/0241749 A1 | 10/2006 | Tu et al. |
| 2007/0004998 A1 | 1/2007 | Rodgers et al. |
| 2007/0021653 A1 | 1/2007 | Hattenbach et al. |
| 2007/0073275 A1 | 3/2007 | Conston et al. |
| 2007/0073390 A1 | 3/2007 | Lee |
| 2007/0078471 A1 | 4/2007 | Schachar et al. |
| 2007/0088242 A1 | 4/2007 | Coroneo |
| 2007/0093740 A1 | 4/2007 | Shetty |
| 2007/0106199 A1 | 5/2007 | Krivoy et al. |
| 2007/0106235 A1 | 5/2007 | Coroneo |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0123919 A1 | 5/2007 | Schachar et al. |
| 2007/0149915 A1 | 6/2007 | Yablonski |
| 2007/0149927 A1 | 6/2007 | Itou et al. |
| 2007/0154621 A1 | 7/2007 | Raad |
| 2007/0156079 A1 | 7/2007 | Brown |
| 2007/0161981 A1 | 7/2007 | Sanders et al. |
| 2007/0179426 A1 | 8/2007 | Selden |
| 2007/0179471 A1 | 8/2007 | Christian et al. |
| 2007/0191863 A1 | 8/2007 | De Juan et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0276315 A1 | 11/2007 | Haffner |
| 2007/0282244 A1 | 12/2007 | Tu et al. |
| 2007/0287958 A1 | 12/2007 | McKenzie et al. |
| 2007/0292470 A1 | 12/2007 | Thornton |
| 2007/0293873 A1 | 12/2007 | Chang |
| 2008/0033351 A1 | 2/2008 | Trogden et al. |
| 2008/0039931 A1 | 2/2008 | Jelle et al. |
| 2008/0045878 A1 | 2/2008 | Bergheim et al. |
| 2008/0051681 A1 | 2/2008 | Schwartz |
| 2008/0058704 A1 | 3/2008 | Hee et al. |
| 2008/0082078 A1 | 4/2008 | Berlin |
| 2008/0091224 A1 | 4/2008 | Griffis, III et al. |
| 2008/0097214 A1 | 4/2008 | Meyers et al. |
| 2008/0097335 A1 | 4/2008 | Trogden et al. |
| 2008/0108932 A1 | 5/2008 | Rodgers |
| 2008/0108933 A1 | 5/2008 | Yu et al. |
| 2008/0109037 A1 | 5/2008 | Steiner et al. |
| 2008/0114440 A1 | 5/2008 | Hlavka et al. |
| 2008/0125691 A1 | 5/2008 | Yaron et al. |
| 2008/0140059 A1 | 6/2008 | Schachar et al. |
| 2008/0147083 A1 | 6/2008 | Vold et al. |
| 2008/0161907 A1 | 7/2008 | Chen et al. |
| 2008/0183289 A1 | 7/2008 | Werblin |
| 2008/0188860 A1 | 8/2008 | Vold |
| 2008/0195027 A1 | 8/2008 | Coroneo |
| 2008/0200860 A1 | 8/2008 | Tu et al. |
| 2008/0200923 A1 | 8/2008 | Beckman et al. |
| 2008/0208176 A1 | 8/2008 | Loh |
| 2008/0210322 A1 | 9/2008 | Unger et al. |
| 2008/0215062 A1 | 9/2008 | Bowen et al. |
| 2008/0221501 A1 | 9/2008 | Cote et al. |
| 2008/0228127 A1* | 9/2008 | Burns ............... A61F 9/00781 604/9 |
| 2008/0236669 A1 | 10/2008 | Unger et al. |
| 2008/0243156 A1 | 10/2008 | John |
| 2008/0243243 A1 | 10/2008 | Williams et al. |
| 2008/0255545 A1 | 10/2008 | Mansfield et al. |
| 2008/0269730 A1 | 10/2008 | Dotson |
| 2008/0277007 A1 | 11/2008 | Unger et al. |
| 2008/0281250 A1 | 11/2008 | Bergsneider et al. |
| 2008/0289710 A1 | 11/2008 | Unger et al. |
| 2008/0306429 A1 | 12/2008 | Shields et al. |
| 2009/0043242 A1 | 2/2009 | Bene et al. |
| 2009/0043321 A1 | 2/2009 | Conston et al. |
| 2009/0043365 A1 | 2/2009 | Friedland et al. |
| 2009/0112245 A1 | 4/2009 | Haefliger |
| 2009/0124973 A1 | 5/2009 | D'Agostino et al. |
| 2009/0132040 A1 | 5/2009 | Frion et al. |
| 2009/0137983 A1 | 5/2009 | Bergheim et al. |
| 2009/0137989 A1 | 5/2009 | Kataoka |
| 2009/0138081 A1 | 5/2009 | Bergheim et al. |
| 2009/0151422 A1 | 6/2009 | Unger et al. |
| 2009/0182421 A1 | 7/2009 | Silvestrini et al. |
| 2009/0198213 A1 | 8/2009 | Tanaka |
| 2009/0204053 A1 | 8/2009 | Nissan et al. |
| 2009/0227934 A1 | 9/2009 | Eutenever et al. |
| 2009/0264813 A1 | 10/2009 | Chang |
| 2009/0287233 A1 | 11/2009 | Huculak |
| 2009/0326432 A1 | 12/2009 | Schmidt et al. |
| 2010/0004581 A1 | 1/2010 | Brigatti et al. |
| 2010/0010416 A1 | 1/2010 | Juan, Jr. et al. |
| 2010/0010452 A1 | 1/2010 | Paques et al. |
| 2010/0025613 A1 | 2/2010 | Tai et al. |
| 2010/0030150 A1 | 2/2010 | Paques et al. |
| 2010/0042209 A1 | 2/2010 | Guarnieri |
| 2010/0057055 A1 | 3/2010 | Camras et al. |
| 2010/0057093 A1 | 3/2010 | Ide et al. |
| 2010/0076419 A1 | 3/2010 | Chew et al. |
| 2010/0087774 A1 | 4/2010 | Haffner et al. |
| 2010/0121248 A1 | 5/2010 | Yu et al. |
| 2010/0121249 A1 | 5/2010 | Yu et al. |
| 2010/0121342 A1 | 5/2010 | Schieber et al. |
| 2010/0137981 A1 | 6/2010 | Silvestrini et al. |
| 2010/0152626 A1 | 6/2010 | Schwartz |
| 2010/0152641 A1 | 6/2010 | Yablonski |
| 2010/0173866 A1 | 7/2010 | Hee et al. |
| 2010/0175767 A1 | 7/2010 | Unger et al. |
| 2010/0185138 A1 | 7/2010 | Yaron et al. |
| 2010/0185205 A1 | 7/2010 | Novakovic et al. |
| 2010/0191103 A1 | 7/2010 | Stamper et al. |
| 2010/0234791 A1 | 9/2010 | Lynch et al. |
| 2010/0234817 A1* | 9/2010 | Nazzaro ............ A61B 17/3468 604/272 |
| 2010/0240987 A1 | 9/2010 | Christian et al. |
| 2010/0241046 A1 | 9/2010 | Pinchuk et al. |
| 2010/0262174 A1 | 10/2010 | Sretavan |
| 2010/0274258 A1 | 10/2010 | Silvestrini et al. |
| 2010/0274259 A1 | 10/2010 | Yaron et al. |
| 2010/0280317 A1 | 11/2010 | Silvestrini et al. |
| 2011/0009874 A1 | 1/2011 | Wardle et al. |
| 2011/0009958 A1 | 1/2011 | Wardle et al. |
| 2011/0022065 A1 | 1/2011 | Shipp |
| 2011/0028883 A1 | 2/2011 | Juan, Jr. et al. |
| 2011/0028884 A1 | 2/2011 | Coroneo |
| 2011/0028983 A1 | 2/2011 | Silvestrini et al. |

(56) References Cited

U.S. PATENT DOCUMENTS

| | | |
|---|---|---|
| 2011/0046536 A1 | 2/2011 | Stegmann et al. |
| 2011/0046728 A1 | 2/2011 | Shareef et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0071524 A1 | 3/2011 | Keller |
| 2011/0077626 A1 | 3/2011 | Baerveldt et al. |
| 2011/0082385 A1 | 4/2011 | Diaz et al. |
| 2011/0087151 A1 | 4/2011 | Coroneo |
| 2011/0092878 A1 | 4/2011 | Tu et al. |
| 2011/0092965 A1 | 4/2011 | Slatkine et al. |
| 2011/0098629 A1 | 4/2011 | Juan, Jr. et al. |
| 2011/0098809 A1 | 4/2011 | Wardle et al. |
| 2011/0105987 A1 | 5/2011 | Bergheim et al. |
| 2011/0112546 A1 | 5/2011 | Juan, Jr. et al. |
| 2011/0118649 A1 | 5/2011 | Stegmann et al. |
| 2011/0118835 A1 | 5/2011 | Silvestrini et al. |
| 2011/0144641 A1 | 6/2011 | Dimalanta, Jr. et al. |
| 2011/0202049 A1 | 8/2011 | Jia et al. |
| 2011/0224597 A1 | 9/2011 | Stegmann et al. |
| 2011/0230877 A1 | 9/2011 | Huculak et al. |
| 2011/0244014 A1 | 10/2011 | Williams et al. |
| 2011/0245753 A1 | 10/2011 | Sunalp |
| 2011/0257623 A1 | 10/2011 | Marshall et al. |
| 2011/0306915 A1 | 12/2011 | De Juan, Jr. et al. |
| 2011/0319793 A1 | 12/2011 | Hyhynen |
| 2011/0319806 A1 | 12/2011 | Wardle |
| 2012/0016286 A1 | 1/2012 | Silvestrini et al. |
| 2012/0022409 A1 | 1/2012 | Gertner et al. |
| 2012/0022424 A1 | 1/2012 | Yamamoto et al. |
| 2012/0022429 A1 | 1/2012 | Silvestrini et al. |
| 2012/0035524 A1 | 2/2012 | Silvestrini |
| 2012/0035525 A1 | 2/2012 | Silverstrini |
| 2012/0065570 A1 | 3/2012 | Yeung et al. |
| 2012/0071809 A1 | 3/2012 | Tu et al. |
| 2012/0071908 A1 | 3/2012 | Sorensen et al. |
| 2012/0078158 A1 | 3/2012 | Haffner et al. |
| 2012/0078281 A1 | 3/2012 | Cox et al. |
| 2012/0089072 A1 | 4/2012 | Cunningham, Jr. |
| 2012/0089073 A1 | 4/2012 | Cunningham, Jr. |
| 2012/0109040 A1 | 5/2012 | Smedley et al. |
| 2012/0123439 A1 | 5/2012 | Romoda et al. |
| 2012/0123440 A1 | 5/2012 | Horvath et al. |
| 2012/0165721 A1 | 6/2012 | Grabner et al. |
| 2012/0165722 A1 | 6/2012 | Horvath |
| 2012/0165723 A1 | 6/2012 | Horvath et al. |
| 2012/0165933 A1 | 6/2012 | Haffner et al. |
| 2012/0197175 A1* | 8/2012 | Horvath .............. A61F 9/00781 604/8 |
| 2012/0203262 A1 | 8/2012 | Connors et al. |
| 2012/0220917 A1 | 8/2012 | Silvestrini et al. |
| 2012/0232570 A1 | 9/2012 | Jenson et al. |
| 2012/0271272 A1 | 10/2012 | Hammack et al. |
| 2012/0283557 A1 | 11/2012 | Berlin |
| 2012/0289883 A1 | 11/2012 | Meng et al. |
| 2012/0310137 A1 | 12/2012 | Silvestrini |
| 2012/0323159 A1 | 12/2012 | Wardle et al. |
| 2013/0006164 A1 | 1/2013 | Yaron et al. |
| 2013/0006165 A1 | 1/2013 | Eutenener et al. |
| 2013/0018295 A1 | 1/2013 | Haffner et al. |
| 2013/0018296 A1 | 1/2013 | Bergheim et al. |
| 2013/0018412 A1 | 1/2013 | Journey et al. |
| 2013/0079701 A1 | 3/2013 | Schieber et al. |
| 2013/0079759 A1 | 3/2013 | Dotson et al. |
| 2013/0090534 A1 | 4/2013 | Burns et al. |
| 2013/0110125 A1 | 5/2013 | Silvestrini et al. |
| 2013/0131577 A1 | 5/2013 | Bronstein et al. |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0158381 A1 | 6/2013 | Rickard |
| 2013/0158462 A1* | 6/2013 | Wardle .............. A61F 9/00781 604/8 |
| 2013/0165840 A1 | 6/2013 | Orge |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0253528 A1 | 9/2013 | Haffner et al. |
| 2013/0281910 A1 | 10/2013 | Tu et al. |
| 2013/0289467 A1 | 10/2013 | Haffner et al. |
| 2014/0034607 A1 | 2/2014 | Meng et al. |
| 2014/0052046 A1 | 2/2014 | Peartree et al. |
| 2014/0081194 A1 | 3/2014 | Burns et al. |
| 2014/0135916 A1 | 5/2014 | Clauson et al. |
| 2014/0155803 A1 | 6/2014 | Silvestrini |
| 2014/0276332 A1 | 9/2014 | Crimaldi et al. |
| 2015/0065940 A1 | 3/2015 | Rangel-Friedman et al. |
| 2015/0374546 A1 | 12/2015 | Hill |
| 2016/0151204 A1 | 6/2016 | Haffner et al. |
| 2017/0273829 A1 | 9/2017 | Tu et al. |
| 2017/0312124 A1 | 11/2017 | Rangel-Friedman et al. |
| 2018/0036172 A1 | 2/2018 | Haffner et al. |
| 2018/0104102 A1 | 4/2018 | Lynch et al. |
| 2018/0325732 A1 | 11/2018 | Burns et al. |

FOREIGN PATENT DOCUMENTS

| | | |
|---|---|---|
| CA | 2643357 | 11/1999 |
| CH | 92111244 | 7/1993 |
| DE | 10042310 A1 | 3/2002 |
| DE | 10127666 A1 | 1/2003 |
| EP | 0436232 | 7/1991 |
| FR | 2553658 A1 | 4/1985 |
| FR | 2757068 A1 | 6/1998 |
| JP | 2003-520077 | 7/2003 |
| JP | 5328788 B2 | 10/2013 |
| RU | 2022539 C1 | 11/1994 |
| RU | 2143250 | 12/1999 |
| RU | 2160573 C1 | 12/2000 |
| WO | WO 89/00869 A1 | 2/1989 |
| WO | WO 92/08406 | 5/1992 |
| WO | WO 94/02081 | 2/1994 |
| WO | WO 94/13234 | 6/1994 |
| WO | WO 96/20742 A1 | 7/1996 |
| WO | WO 98/23237 A1 | 6/1998 |
| WO | WO 98/37831 | 9/1998 |
| WO | WO 99/26567 A1 | 6/1999 |
| WO | WO 99/30641 A1 | 6/1999 |
| WO | WO 2000/67687 A1 | 11/2000 |
| WO | WO 01/68016 A2 | 9/2001 |
| WO | WO 01/85065 | 11/2001 |
| WO | WO 2001/97727 | 12/2001 |
| WO | WO 2002/36052 | 5/2002 |
| WO | WO 02/074052 A2 | 9/2002 |
| WO | WO 02/102274 A2 | 12/2002 |
| WO | WO 03/041622 | 5/2003 |
| WO | WO 03/045290 A1 | 6/2003 |
| WO | WO 03/073968 A2 | 9/2003 |
| WO | WO 2004/008945 A2 | 1/2004 |
| WO | WO 2004/093761 A1 | 11/2004 |
| WO | WO 2005/107664 A2 | 11/2005 |
| WO | WO 2005/107845 | 11/2005 |
| WO | WO 05/117780 | 12/2005 |
| WO | WO 2008/061043 A2 | 5/2008 |
| WO | WO 09/012406 | 1/2009 |
| WO | WO 10/093945 A3 | 8/2010 |
| WO | WO 10/135369 | 11/2010 |
| WO | WO 11/020633 A1 | 2/2011 |
| WO | WO 13/148275 | 10/2013 |

OTHER PUBLICATIONS

Constad, William H., et al., Use of an Angiotensin Converting Enzyme Inhibitor in Ocular Hypertension and Primary Open-Angle Glaucoma, 103 Am J Opthalmol 674 (1988).

(56) References Cited

OTHER PUBLICATIONS

Coote, "Glaucoma Hollow Fiber Filters—A New Glaucoma Seton. Preliminary Results," J. Glaucoma, vol. 8, No. 1, Supplement (1999), p. S4 (1 page).
De Juan et al., "Refinements in microinstrumentation for vitrous surgery," Am. J. Ophthalmol. 109:218-20 (1990).
Dorland's Illustrated Medical Dictionary, 28th Edition, Philadelphia: W.B. Saunders Company, 1994, p. 167.
Duane's Ophthalmology on CD-ROM, 2006 Edition, Chapter 56—Medical Therapy of Glaucoma by Marc Weitzman and Joseph Caprioli.
Fletcher, Daniel A., Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.
Hill, Richard A., MD, George Baerveldt, MD, Serdar A. Ozler, MD, Michael Pickford, BA, Glen A. Profeta, BS, & Michael W. Berns, PhD, Laser Trabecular Ablation (LTA), *Lasers in Surgery and Medicine*, 1991, vol. 11, pp. 341-346.
Hoskins, H. Dunbar, et al., Diagnosis and Therapy of the Glaucomas, Chapter 4: Aqueous Humor Outflow, 61 edition, pp. 41-66 (1989) (28 pages).
Johnson, et al., *Schlemm's Canal Becomes Smaller After Successful Filtration Surgery*, (reprinted) ARCM Ophthalmol/vol. 118, Sep. 2000 (www.archophthalmol.com) p. 1251-1256.
Johnstone, M.A., R. Stegmann, and B.A. Smit, *American Glaucoma Society, 12th Annual Meeting, Cylindrical Tubular Structures Spanning from Trabecular Meshwork Across SC*, Laboratory Studies with SEM, TEM and Tracers Correlated with Clinical Findings, Abstract No. 18., p. 39, 2002.
Johnson, Douglas H., M.D., et al.: Basic Sciences in Clinical Glaucoma: How Does Nonpenetrating Glaucoma Surgery Work? Aqueous Outflow Resistance and Glaucoma Surger; Journal of Glaucoma; 2001, vol. 10, No. 1, pp. 55-67.
Jordan et al., Cyclodialysis ab interno as a surgical approach to intractable glaucoma, Graefe's Arch Clin Exp Opthalmol (2007) 245, pp. 1071-1076.
Jordon, et al., "A Novel Approach to Suprachoroidal Drainage for the Surgical Treatment of Intractable Glaucoma," J Glaucoma 15(3): 200-205 (2006).
Karlen, M. E., et al., "Deep sclerectomy with collagen implant: medium term results", Br. J. Ophthalmol. vol. 83, No. 1, Jan. 1999, pp. 6-11 (abstract only).
Katuri, Kalyan C., Asrani, Sanjay and Ramasubramanian, Melur K., "Intraocular Pressure Monitoring Sensors", IEEE Sensors Journal, vol. 8, No. 1, Jan. 2008, 8 pp.
Kim et al., Controlled Drug Release from an Ocular Implant: An Evaluation Using Dynamic Three-Dimensional Magnetic Resonance Imaging. Invest Ophthalmol Vis Sci. 2004;45:2722-2731.
Kimura, T., et al.; The Efficacy of Isopropyl Unoppostone in the Concomitant Application of B Blocker, Dipivefrin and Pilocarpine; Glaucoma Clinical Pharmacology II, Abstract B56, IVOS 1998 vol. 39, (cover page and p. S258).
Klemm, A. Balazs, J. Draeger, R. Wiezorrek, *Experimental use of space-retaining substances with extended duration: functional and morphological results*, Graefe's Arch Clin Exp Ophthalmol (1995) 233:592-597.
Krejci, "Cyclodialysis with Hydroxyethyl Methacrylate Capillary Strip (HCS)," Opthalmologica, vol. 164 (1972), pp. 113-121 (9 pages).
Moses, Robert A., et al., "Blood Reflux in Schlemm's Canal", Arch Ophthamol., vol. 97, Jul. 1979, pp. 1307-1310.
Oatts et al., "In vitro an in vivo comparison of two suprachoroidal shunts," Invest. Opthalmol. Vis. Sci. 54:5416-23 (2013).
Ozdamar, et al., "Suprachoroidal Seton Implantation in Refractory Glaucoma: A novel Surgical Technique", Journal of Glaucoma 12:354-359, 2003.
Pajic, Bojan et al., "A novel technique of ab interno glaucoma surgery: follow-up results after 24 months", Graefe's Arch Clin Exp Ophthalmol, Jul. 2005, (2006) 244:22-27.
Pederson, Jonathan et al., "Uveoscleral Aqueous Outflow in the Rhesus Monkey: Importance of Uveal Reabsorption," Invest. Ophthalmol, Visual Sci. Nov. 1977, Uveal Reabsorption of Aqueous Humor, vol. 16, No. 11, pp. 1008-1017.
Qu, I., et al., Isolation and characterization of noncytopathic pestivirus mutants reveals a role for nonstructural protein NS4B in viral cytopathogenicity. Nov. 2001 Journal of Virology. vol. 75, No. 22, 10651-62, see Fig. 1 and p. 10654.
Rizq, et al., Intraocular Pressure Measurement at the Choroid Surface: A Feasibility Study with Implications for Implantable Microsystems, Br J Ophthalmol 2001; 85:868-871, Jul. 2001.
Rosenberg, et al., "Implants in Glaucoma Surgery", The Glaucomas 1996, Chapter 88, pp. 1783-1807 (27 pages).
Sherman, Steven H., et al., "The Fate of Anterior Chamber Fluorescein in the Monkey Eye 1. The Anterior Chamber Outflow Pathways", Exp. Eye Res. vol. 27, pp. 159-173 (1978) (15 pages).
Timmermans, et al., Possible Subdivision of Postsynaptic Adrenoceptors Mediating Pressor Responses in the Pithed Rat; Nauyn-Schmeideberg's Arch. Pharmacol., 310, pp. 189-193 (1979).
Tsontcho Ianchulev, Chapter 21: The CyPass Suprachoroidal Micro-Stent, in J.R. Samples & I.I.K. Ahmed (eds.), Surgical Innovations in Glaucoma 229 (Springer Science+Business Media 2014).
Troncoso, M.D., Cyclodialysis with Insertion of a Metal Implant in the Treatment of Glaucoma, Read before the Section on Ophthalmology at the Ninetieth Annual Session of the American Medical Association, St. Louis, May 17, 1939, Archives of Ophthalmology, pp. 270-300, downloaded from www.archophthalmol.com on Aug. 5, 2010.
Van Der Veen, G., et al., "The Gonioseton, A Surgical Treatment for Chronic Glaucoma," Documenta Ophthalmologica, 1990 (75) pp. 365-375.
Webster's Third New International Dictionary of the English Language (Unabridged), definitions of "deploy" and "deployment", p. 605 (2002) (4 pages).
Welsh, N. H., et al., "The 'deroofing' of Schlemm's canal in patients with open-angle glaucoma through placement of a collagen drainage device", Ophthalmic Surg. Lasers, vol. 29, No. 3, Mar. 1998,pp. 216-226 (abstract only).
Zhou, Jianbo, PhD, Gregory T. Smedley, PhD., *A Trabecular Bypass Flow Hypothesis*, Feb. 2005, vol. 14 No. 1, pp. 74-83.
Bae, et al., "In vitro experiment of the pressure regulating valve for a glaucoma implant", Journal of Micromechanics and Microengineering 13.5, 13:613-619, No. 5, Sep. 2003.
Bartolomei, et al., "Seton implantation to divert aqueous humor", Journal of Glaucoma, 13:348- 349, No. 4, Aug. 2004.
Chen, et al., "Trabeculetomy combined with implantation of sil-icon rubber slice for intractable glaucoma", Eye Science, 18:95-98, vol. 2, Jun. 2002.
Gal, "A novel glaucoma drainage valve", ProQuest Dissertations Publishing, 131 pages, 1999.
Lim, "Development of a new glaucoma drainage device", ProQuest Dissertations Publishing, 147 pages, 2001.
Refojo, "Current status of biomaterials in ophthalmology", Survey of ophthalmology, 26:257-265, No. 5, 1982.
Scott, et al., "Use of glaucoma drainage devices in the management of glaucoma associated with aniridia", American Journal of Ophthalmology, 135:155-159, No. 2, Feb. 1, 2003.
Tham, et al., "Incisional surgery for angle closure glaucoma", Seminars in Ophthalmology, 17:92-99, No. 2, Jun. 2002.
Yablonski, "Internal tube shunt from anterior chamber to suprachoroidal space: A novel glaucoma surgery", IOVS, vol. 46, No. Suppl., p. 1223, 2005.
Yablonski, Trabeculectomy with internal Tube Shunt—A novel Glaucoma surgery, Journal of Glaucoma, vol. 14, No. 2:91-97, 2005.
Yan, et al., "Schlemm's Canal and Trabecular Meshwork in Eyes with Primary Open Angle Glaucoma: A Comparative Study Using High-Frequency", PLOS ONE, 15 pages, Jan. 4, 2016.

(56) References Cited

OTHER PUBLICATIONS

Ning, "Optimum Design of a New Aqueous Humor Drainage Implant for Glaucoma and the Animal", ProQuest Dissertations Publishing, 2004.

Tsontcho Ianchulev, Chapter 3: Suprachoroidal Space as a Therapeutic Target, in J.R. Samples & I.I.K. Ahmed (eds.), Surgical Innovations in Glaucoma 33 (Springer Science+Business Media 2014).

* cited by examiner

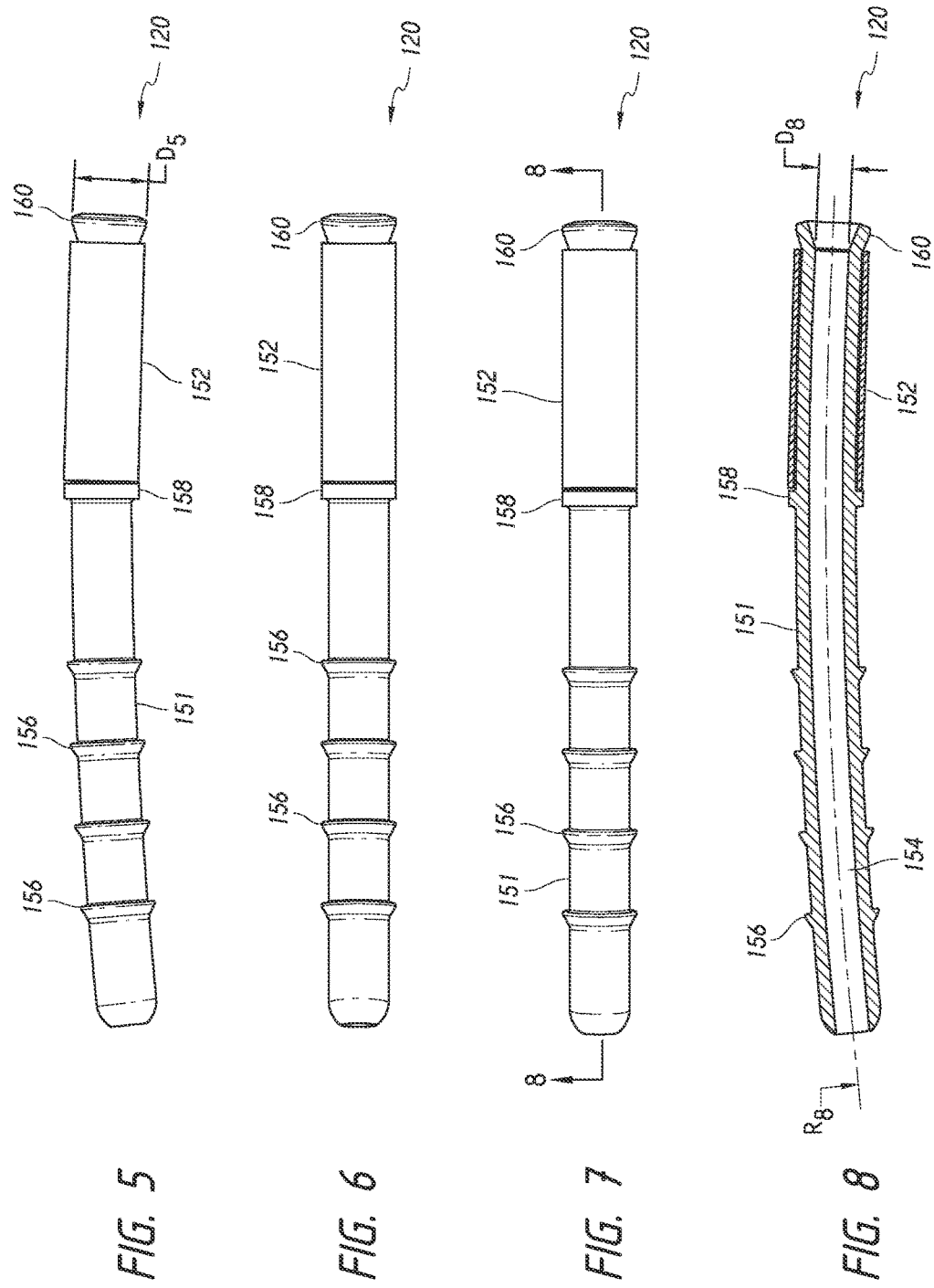

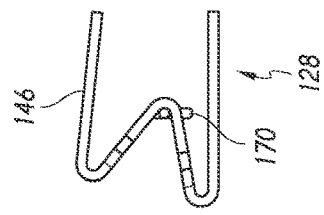
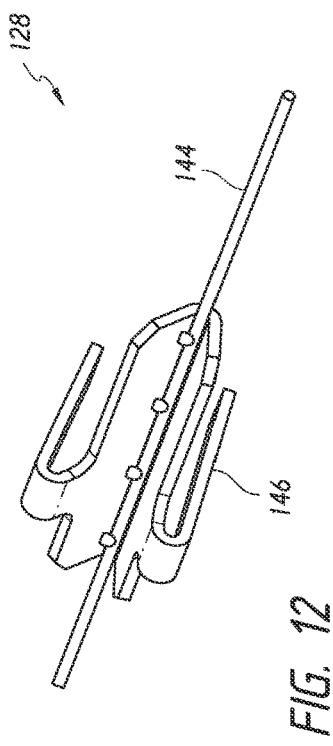
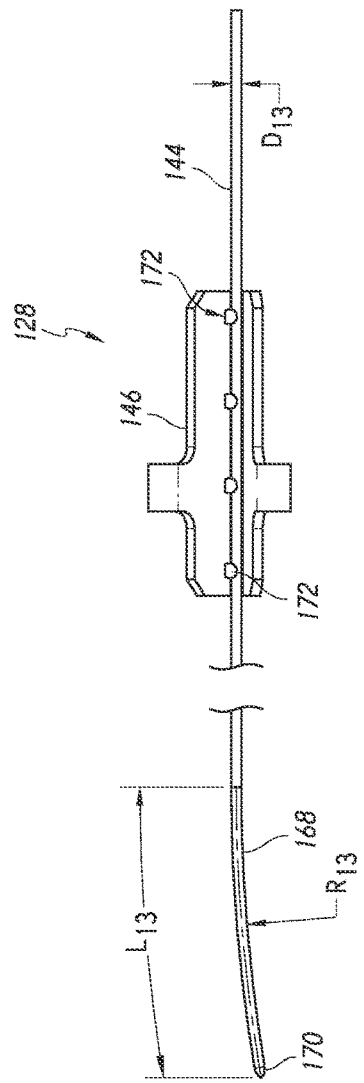
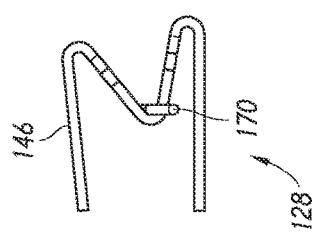

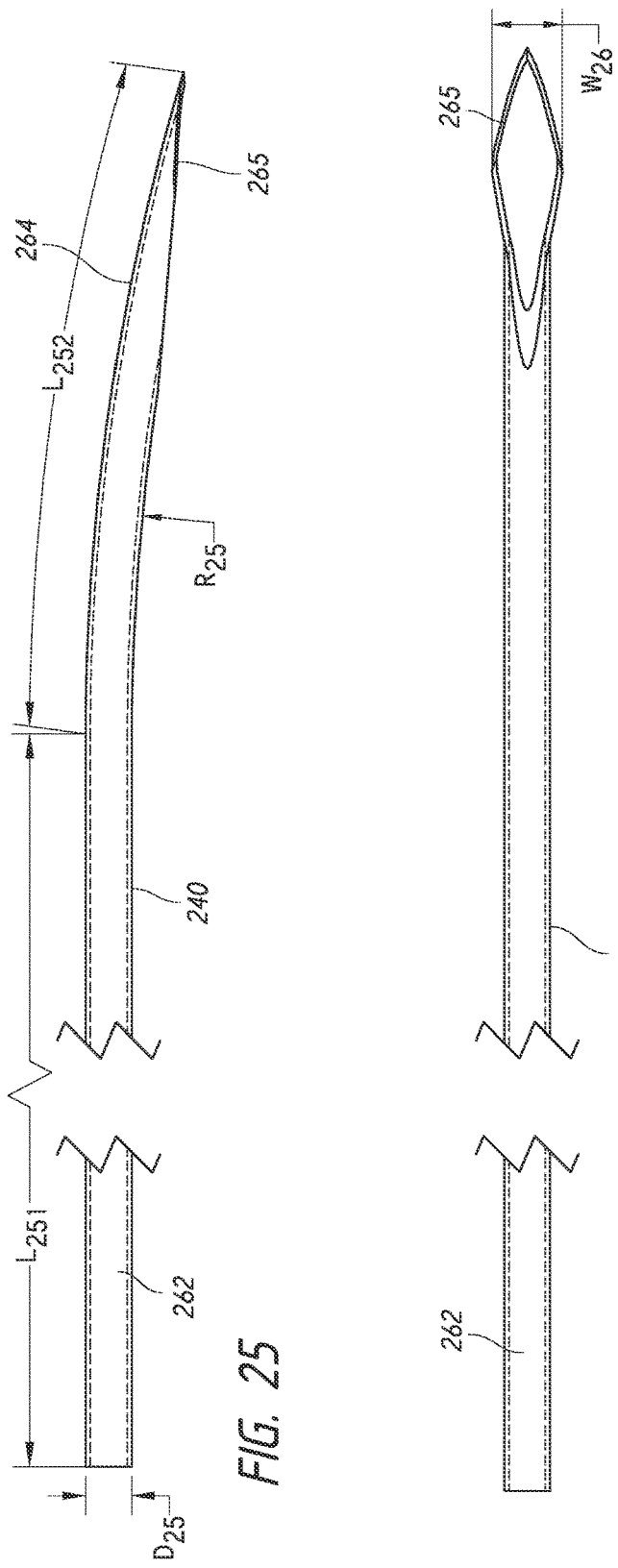

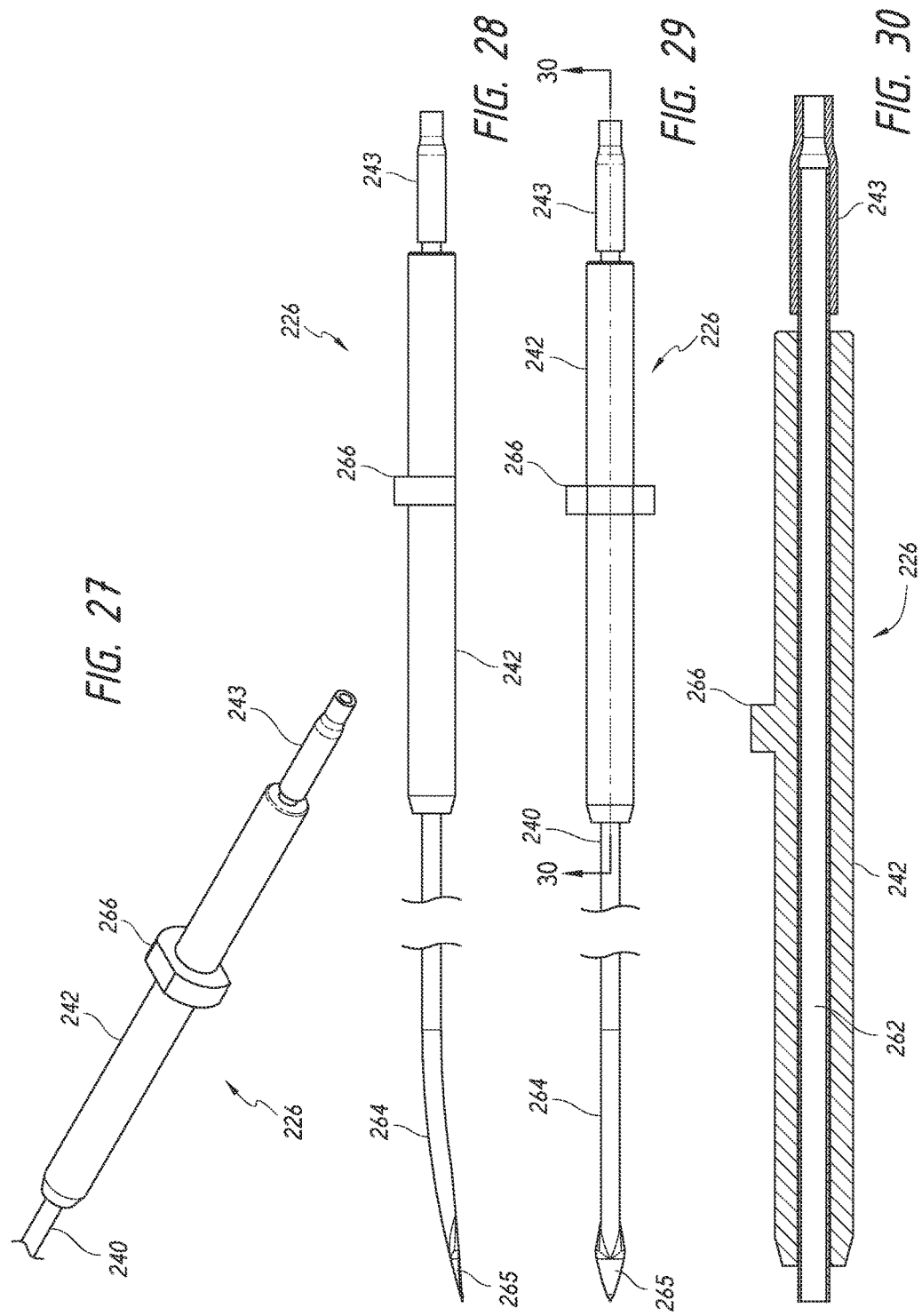

SYSTEMS AND METHODS FOR DELIVERING AN OCULAR IMPLANT TO THE SUPRACHOROIDAL SPACE WITHIN AN EYE

FIELD

This disclosure generally relates to intraocular pressure reduction and more specifically to systems, devices and methods for delivering an intraocular implant to the suprachoroidal space within an eye to treat glaucoma, ocular hypertension and/or other ocular disorders.

BACKGROUND

A human eye is a specialized sensory organ capable of light reception and is able to receive visual images. Aqueous humor is a transparent liquid that fills at least the region between the cornea, at the front of the eye, and the lens. A trabecular meshwork, located in an anterior chamber angle, which is formed between the iris and the cornea, normally serves as a drainage channel for aqueous humor from the anterior chamber so as to maintain a balanced pressure within the anterior chamber of the eye.

Glaucoma is a group of eye diseases encompassing a broad spectrum of clinical presentations, etiologies, and treatment modalities, Glaucoma causes pathological changes in the optic nerve, visible on the optic disk, and it causes corresponding visual field loss, resulting in blindness if untreated, Lowering intraocular pressure is a major treatment goal in glaucomas.

In glaucomas associated with an elevation in eye pressure (intraocular hypertension), a main source of resistance to outflow is typically in the trabecular meshwork. The tissue of the trabecular meshwork normally allows the aqueous humor (hereinafter also referred to as "aqueous") to enter Schlemm's canal, which then empties into aqueous collector channels in the posterior wall of Schlemm's canal and then into aqueous veins, which form the episcleral venous system. Aqueous is continuously secreted by a ciliary body around the lens so there is a constant flow of aqueous from the ciliary body to the anterior chamber of the eye. Pressure within the eye is determined by a balance between the production of aqueous and its exit through the trabecular meshwork (major route) and uveoscleral outflow (minor route) pathways. The portion of the trabecular meshwork adjacent to Schlemm's canal (the juxtacanilicular meshwork) can cause most of the resistance to aqueous outflow.

Glaucoma is broadly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye.

Open-angle glaucoma is any glaucoma in which the exit of aqueous through the trabecular meshwork is diminished while the angle of the anterior chamber remains open. For most cases of open-angle glaucoma, the exact cause of diminished filtration is unknown. Primary open-angle glaucoma is the most common of the glaucomas, and is often asymptomatic in the early to moderately advanced stages of glaucoma. Patients may suffer substantial, irreversible vision loss prior to diagnosis and treatment.

Most current therapies for glaucoma are directed toward decreasing intraocular pressure. Medical therapy includes topical ophthalmic drops or oral medications that reduce the production of aqueous or increase the outflow of aqueous. However, drug therapies for glaucoma are sometimes associated with significant side effects. The most frequent and perhaps most serious drawback to drug therapy, especially the elderly, is patient compliance. Patients often forget to take their medication at the appropriate times or else administer eye drops improperly, resulting in under- or overdosing. Patient compliance is particularly problematic with therapeutic agents requiring dosing frequencies of three times a day or more, such as pilocarpine. Because the effects of glaucoma are irreversible, when patients dose improperly, allowing ocular concentrations to drop below appropriate therapeutic levels, further permanent damage to vision occurs.

SUMMARY

As such, a need exists for a more facile, convenient, less invasive, and less traumatic means of delivering an intraocular pressure controlling implant into an eye while providing a cost-effective but safe surgical procedure, it is one advantage of certain embodiments of the invention(s) disclosed herein to provide delivery devices, systems and methods for inserting an implant into an eye. The delivery or inserter devices or systems can be used to dispose or implant an ocular stent or implant, such as a shunt, in communication with the suprachoroidal space, uveoscleral outflow pathway (sometimes referred to as uveal scleral outflow pathway) and/or supraciliary space of the eye. The implant can drain fluid from an anterior chamber of the eye to a physiologic outflow path of the eye, such as, the suprachoroidal space, uveoscleral outflow pathway, or supraciliary space. Alternatively, or in addition, the implant can elute a drug or therapeutic agent. The delivery or inserter devices or systems can be used in conjunction with other ocular surgery, for example, but not limited to, cataract surgery through a preformed corneal incision, or independently with the inserter configured to make a corneal or limbal incision. The implant can be preloaded with or within the inserter to advantageously provide an operator-friendly package, such as a sterile package, for convenient use by a surgeon, doctor or operator. In some embodiments, the implant is not preloaded n the delivery device or inserter and/or is not provided within the same package e delivery device or inserter.

While a majority of the aqueous leaves the eye through the trabecular meshwork and Schlemm's canal, it is believed that at least about 10 to about 20 percent of the aqueous in humans leaves through the uveoscleral pathway. The degree with which uveoscleral outflow contributes to the total outflow of the eye appears to be species dependent. As used herein, the term "uveoscleral outflow pathway" is to be given its ordinary and customary meaning to a person of ordinary skill in the art (and it is not to be limited to a special or customized meaning), and refers without limitation to the space or passageway whereby aqueous exits the eye by passing through the ciliary muscle bundles located at or near an angle of the anterior chamber and into the tissue planes between the choroid and the sclera, which extend posteriorly to the optic nerve. From these tissue planes, it is believed that the aqueous travels through the surrounding scleral tissue and drains via the scleral and conjunctival vessels, or is absorbed by the uveal blood vessels.

As used herein, the term "supraciliary space" is to be given its ordinary and customary meaning to a person of ordinary skill in the art (and it is not to be limited to a special or customized meaning), and refers without limitation to the portion of the uveoscleral pathway through the ciliary muscle and between the ciliary body and the sclera, and the term "suprachoroidal space" is to be given its ordinary and customary meaning to a person of ordinary skill in the art (and it is not to be limited to a special or customized meaning), and refers without limitation to the portion of the uveoscleral outflow pathway between the choroid and sclera.

The term "implant" as used herein is a broad term, and is to be given its ordinary and customary meaning to a person of ordinary skill in the an (and it is not to be limited to a special or customized meaning), and refers without limitation to drainage shunts, stents, sensors, drug delivery implants, drugs, therapeutic agents, fluids, or any other device or substance capable of being permanently or temporarily inserted within an eye and left within a body after removal of a delivery instrument.

As used herein, "implants" refers to ocular implants which can be implanted into any number of locations in the eye. In some embodiments, the ocular implants are drainage implants designed to facilitate or provide for the drainage of aqueous humor from the anterior chamber of an eye into a physiologic outflow pathway in order to reduce intraocular pressure. In some embodiments, the implant can be configured to provide a fluid flow path for draining aqueous humor from the anterior chamber to a uveoscleral outflow pathway. In some embodiments, the aqueous humor is diverted to the supraciliary space and/or the suprachoroidal space of the uveoscleral outflow pathway.

If desired, more than one implant of the same or different type may be implanted. For example, the implants disclosed herein may be used in combination with trabecular bypass shunts, such as those disclosed in U.S. Patent Publication 2004/0050392, filed Aug. 28, 2002, and those described in U.S. Patent Publication 2005/0271704, filed Mar. 18, 2005, the entire contents of each of which are incorporated herein by reference. Additionally, implantation may be performed in combination with other surgical procedures, such as cataract surgery. All or a portion of the implant may be coated, e.g. with heparin, preferably in the flow path, to reduce blood thrombosis or tissue restenosis.

In some embodiments, at least some slight and/or predetermined flexibility is provided to an obturator, or trocar, of an implant delivery system for ocular tissue penetration and to conform in with an eye's structure and anatomy at or along the pathway to an implantation site. In some embodiments, at least some slight and/or predetermined flexibility is provided to an implant or stent to conform with the eye's structure and anatomy at or along the pathway to an implantation site. The terms "obturator" and "trocar" are used interchangeably herein, and in addition to their ordinary meanings, may refer to an elongate instrument with a generally rounded or non-sharp distal tip.

In accordance with several embodiments, an ocular implant delivery system includes a delivery device (e.g., an applicator or inserter) and an ocular implant. The implant may be preloaded on or within the delivery device and provided as a kit within a package for convenient use by an operator. The delivery device may include a generally elongated outer housing that is ergonomically contoured. The delivery device may also include an elongated insertion sleeve partially disposed in the outer housing and having a non-linear exposed distal portion extending out of a distal end of the housing. The non-linear exposed distal portion of the insertion sleeve may have a curvature adapted to conform to an anatomical curvature of the eye, such as the cornea and/or sclera. The delivery device may include an obturator, or trocar, passing through a lumen of the insertion sleeve and having a non-linear distal portion extending beyond the non-linear distal portion of the insertion sleeve. In one embodiment, the obturator has a rounded, blunt or non-faceted distal end in use, the non-linear distal portion of the obturator is adapted to provide access to a suprachoroidal space through a ciliary muscle attachment. In one embodiment, the access is provided without dissecting a ciliary body portion at the anterior chamber angle from the sclera but instead is provided by insertion of the obturator through a fibrous band of the ciliary muscle. In some embodiments, the non-linear distal portion of the obturator is flexible and has a curvature adapted to maintain pressure against the sclera during insertion into the suprachoroidal space. The delivery device may also include a trigger operatively coupled to the obturator such that movement of the trigger towards a proximal end of the housing retracts the obturator within the insertion sleeve, thereby deploying the implant off of the obturator.

The implant is adapted to be disposed on the non-linear portion of the obturator and positioned distally of the non-linear distal portion of the insertion sleeve prior to insertion of the delivery device into an eye. For example, the implant may be loaded on the obturator by inserting a distal end of the obturator within a lumen of the implant and advancing the implant over the obturator or advancing the obturator toward a distal end of the implant. In some embodiments, in use, a distal end of the insertion sleeve is adapted to react against a proximal end of the implant as the obturator is being retracted to deliver the implant. The insertion sleeve may be sized to extend through a corneal incision and into an anterior chamber of the eye. In some embodiments, the implant has a curvature which substantially matches the curvature of the non-linear portion of the obturator. In some embodiments, the curvature of the non-linear distal portion of the obturator and/or the implant is larger than a diameter of the eye.

In use, the trigger may be manually controlled and held in a forward position, and retracted in a backward motion to cause delivery of the implant once a distal end of the implant has been advanced to a desired location within the suprachoroidal space, wherein the backward motion of the obturator is adapted to prevent against over-insertion of the implant within the suprachoroidal space. In some embodiments, a distal tip of the obturator is rounded so as not to cause scraping of the sclera while still being adapted to provide access to the suprachoroidal space through the ciliary muscle attachment.

In some embodiments, the implant is an elongate tube having an outer diameter of the implant is between 300 and 400 microns. In some embodiments, a distal portion of the implant includes a plurality of circumferential retention members. A distal tip of the implant may be tapered. A proximal end of the implant may include a flange in some embodiments, the delivery device includes reuse prevention structures configured to limit use to a single use. For example, the reuse prevention structures ma include a pair of glue blocks mounted on each side of a trigger of the obturator adapted to melt upon sterilization to lock the trigger against further use.

In accordance with several embodiments, an ocular implant delivery system includes a delivery device, applicator or inserter having a generally elongated outer housing that is ergonomically contoured and an elongated insertion needle partially disposed in the outer housing and having a non-linear exposed distal portion. The delivery device may further include an implant pusher tube extending through a lumen of the elongated insertion needle and having a non-linear distal portion. In one embodiment, the delivery device includes an obturator passing through a lumen of the pusher tube and having a non-linear distal portion. In use, the non-linear distal portion of the obturator may be adapted to provide access to a suprachoroidal space through a ciliary muscle attachment. The non-linear distal portion of the obturator may be flexible and have a curvature adapted to maintain pressure against the sclera during insertion into the suprachoroidal space. The delivery device may also include a pusher tube trigger operatively coupled to the pusher tube such that movement of the pusher tube trigger towards a proximal end of the housing retracts the obturator toward the housing. In use, a distal end of the pusher tube may be adapted to react against a proximal end of an implant loaded on to the obturator as the obturator is being retracted within the housing to deliver the implant.

In one embodiment, the insertion needle is a corneal penetration needle (e.g., a 25±5 gauge needle) adapted to create a self-sealing corneal incision (e.g., at or near the corneal limbus). The non-linear portions of the insertion needle, pusher tube and/or obturator may have a substantially matching curvature. The system may also include an implant preloaded onto the obturator and provided together with the delivery device in a kit or packaging. The implant may have a curvature that substantially conforms to or matches, the curvatures of the insertion needle, pusher tube and obturator.

In some embodiments, the pusher tube trigger is operatively coupled to a trigger of the obturator. The obturator may be advanceable and retractable by actuation of the trigger of the obturator. In some embodiments, when the pusher tube is fully advanced the pusher tube is locked to prevent further motion. The delivery device may include reuse prevention structures designed and/or adapted to limit use of the delivery device to a single use. For example, the reuse prevention structures may include a pair of glue blocks mounted on each side of the pusher tube trigger adapted to melt upon sterilization to lock the pusher tube trigger against further use.

In accordance with several embodiments an ocular implant delivery device includes a generally elongated outer housing that is ergonomically contoured and an elongated insertion sleeve partially disposed in the outer housing and having a non-linear exposed distal portion. The ocular implant delivery device may also include a tubular support member surrounding a portion of the elongated insertion sleeve. The tubular support member may have a proximal end within the outer housing and a distal end extending outside of the outer housing. The tubular support member may be configured to facilitate coupling of the elongated insertion sleeve to the outer housing. The tubular support member may surround a portion of the elongated insertion sleeve. The delivery device may also include an obturator passing through a lumen of the elongated insertion sleeve and having a non-linear distal portion extending beyond the non-linear exposed distal portion of the elongated insertion sleeve and a trigger operatively coupled to the obturator such that actuation of the trigger retracts the obturator into the insertion sleeve, thereby causing a proximal end of an implant disposed on the non-linear portion of the obturator to react against a distal end of the insertion sleeve so as to facilitate deployment of the implant from the obturator. In some embodiments, the non-linear distal portion of the obturator carrying the implant is configured to be advanced into a suprachoroidal space of an eye and the non-linear distal portion of the obturator has a curvature configured to be larger than a diameter of the eye.

For purposes of summarizing embodiments of the invention(s), certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of some of the embodiments of the invention(s) and some of their features and advantages, certain preferred embodiments and modifications thereof will become apparent to those skilled in the art from the detailed description herein having reference to the figures that follow, which are intended to illustrate and not to limit the disclosure.

FIG. 5 is a simplified side view of an ocular implant illustrating features and advantages in accordance with certain embodiments.

FIG. 6 is a simplified bottom or lower view of the ocular implant of FIG. 5 illustrating features and advantages in accordance with certain embodiments.

FIG. 7 is a simplified top or upper view of the ocular implant of FIG. 5 illustrating features and advantages in accordance with certain embodiments.

FIG. 8 is a simplified sectional view along line 8-8 of the ocular implant of FIG. 7 illustrating features and advantages in accordance with certain embodiments.

FIG. 12 is a simplified perspective of a trocar assembly of the implant delivery device of FIG. 2 illustrating features and advantages in accordance with certain embodiments.

FIG. 13 is a simplified side view of the trocar assembly of FIG. 12 illustrating features and advantages in accordance with certain embodiments.

FIG. 14 is a simplified distal end view of the trocar assembly of FIG. 12 illustrating features and advantages in accordance with certain embodiments.

FIG. 15 is a simplified proximal end view of the trocar assembly of FIG. 12 illustrating features and advantages in accordance with certain embodiments.

FIGS. 18 to 22 are simplified schematic views illustrating a surgical procedure or method of implanting an ocular implant in the suprachoroidal space of an eye using the implant delivery device of FIG. 2, having features and advantages in accordance with certain embodiments wherein: FIG. 18 illustrates insertion of the implant and the delivery device into an anterior chamber of the eye; FIG. 19 illustrates positioning of the implant at an implantation site; FIG. 20 illustrates advancement and implantation of the implant in a suprachoroidal space formed between the choroid and the sclera; FIG. 21 illustrates retraction of a trocar of the delivery device from the suprachoroidal space; and FIG. 22 illustrates the removal of the delivery device from the anterior chamber of the eye with the implant remaining within the eye.

FIG. 25 is a simplified side view of a penetration needle of the implant delivery device of FIG. 23 illustrating features and advantages in accordance with certain embodiments.

FIG. 26 is a simplified bottom or lower view of the penetration needle of FIG. 25 illustrating features and advantages in accordance with certain embodiments.

FIG. 27 is a simplified perspective view of a penetration needle assembly of the implant delivery device of FIG. 23, including the penetration needle of FIG. 25, illustrating features and advantages in accordance with certain embodiments.

FIG. 28 is a simplified side view of the penetration needle assembly of FIG. 27 illustrating features and advantages in accordance with certain embodiments.

FIG. 29 is a simplified top or upper view of the penetration needle assembly of FIG. 27 illustrating features and advantages in accordance with certain embodiments.

FIG. 30 is a simplified sectional view along line 30-30 of FIG. 29 illustrating features and advantages in accordance with certain embodiments.

FIGS. 39 to 44 are simplified schematic views illustrating a surgical procedure or method of implanting an ocular implant in the suprachoroidal space of an eye using the implant delivery device of FIG. 23, having features and advantages in accordance with certain embodiments, wherein: FIG. 39 illustrates insertion of the implant and the delivery device into an anterior chamber of the eye through an incision made by an insertion needle of the delivery device; FIG. 40 illustrates deployment of a trocar and a pusher tube of the delivery or inserter system or device such that the implant is exposed within the anterior chamber FIG. 41 illustrates positioning of the implant at an implantation site; FIG. 42 illustrates advancement and implantation of the implant in the suprachoroidal space; FIG. 43 illustrates retraction of a trocar of the delivery device from the suprachoroidal space; and FIG. 44 illustrates the removal of the delivery device from the anterior chamber of the eye with the implant remaining within the eye.

DETAILED DESCRIPTION

The preferred embodiments of the invention described herein relate generally to intraocular pressure reduction and, in particular, to systems, devices and methods for delivering an intraocular implant to the suprachoroidal space, supraciliary space or other anatomical space within a uveoscleral outflow pathway of an eye to treat glaucoma, ocular hypertension and/or other ocular disorders.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
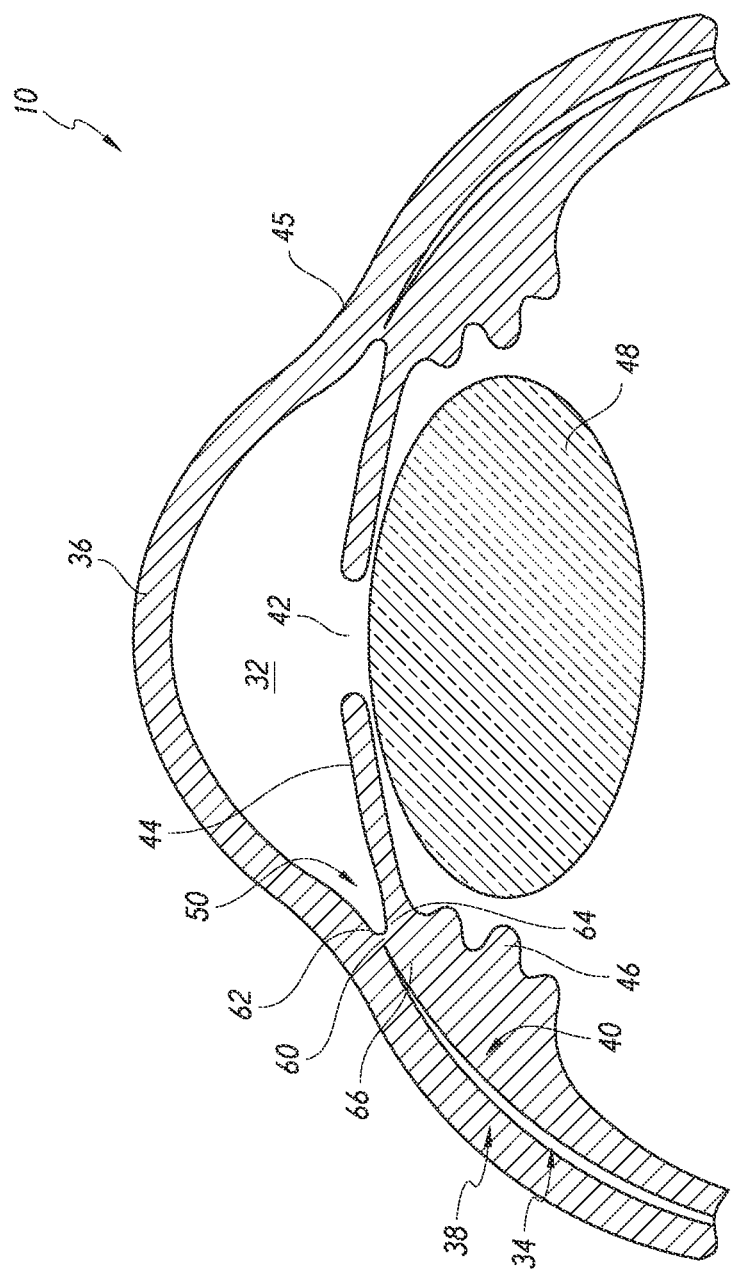
FIG. 1 is a simplified schematic sectional view of a portion of an eye illustrating certain ocular anatomical features thereof and therein.

FIG. 1 shows relative anatomical features of an eye 10. The features include an anterior chamber 32 and a sclera 38, which is a thick collagenous tissue that covers the entire eye 10 except a portion that is covered by a cornea 36. The cornea 36 is a thin transparent tissue that focuses and transmits light into the eye and through a pupil 42, which is a generally circular hole in the center of an iris 44 (colored portion of the eye), to a lens 48. The cornea 36 merges into the sclera 38 at a juncture referred to as a limbus 45. Ciliary bodies 46 are vascular tissue that extend along the interior of the sclera 38 from the outer edges of the iris in the limbal region to a choroid 40.

The anterior chamber 32 of the eye 10, which is bound anteriorly by the cornea 36 and posteriorly by the iris 44 and the lens 48, is filled with aqueous humor or aqueous fluid (which may be simply referred to herein as aqueous). Aqueous is produced primarily by the ciliary bodies 46 and flows into the posterior chamber, bounded posteriorly by the lens 48 and anteriorly by the iris 44. The aqueous humor then flows anteriorly through the pupil 42 and into the anterior chamber 32 until it reaches an anterior chamber angle 50, followed generally between the iris 44 and the cornea 36.

In a normal eye, at least some of the aqueous humor drains from the anterior chamber 32 through a trabecular meshwork into Schlemm's canal and thereafter through a plurality of collector ducts and aqueous veins, which merge with blood-carrying veins, and into systemic venous circulation. Intraocular pressure is maintained by an intricate balance between secretion and outflow of aqueous humor in the manner described above. Glaucoma is, in most cases, characterized by an excessive buildup of aqueous humor in the anterior chamber 32, which leads to an increase in intraocular pressure. Fluids are relatively incompressible, and thus, intraocular pressure is distributed relatively uniformly throughout the eye 10.

The choroid 40 is a vascular layer of the eye 10 located between the sclera 38 and a retina (not identified in FIG. 1). An optic nerve snot shown) transmits visual information to the brain and is the anatomic structure that is progressively destroyed by glaucoma, ocular hypertension, and/or other ocular or ophthalmic disorders.

Another existing aqueous drainage route is provided through a suprachoroidal space 34, which is a space or region generally defined between the sclera 38 and the choroid 40. The suprachoroidal space 34 is exposed to the anterior chamber 32 through the anterior chamber angle 50. The tissue connection between the anterior chamber 32 and suprachoroidal space 34 is generally via a fibrous attachment zone 60 generally disposed between a scleral spur 62 and iris processes 64 and/or ciliary muscle 66, which is a part of the choroid 40.

Certain embodiments of suprachoroidal implants, delivery devices, associated components and suprachoroidal implantation methods and procedures, and the like, among others, are disclosed in U.S. Patent Application Publication No. 2008/0228127, published Sep. 18, 2008, the entire content of which is incorporated by reference herein.

Delivery Device for Advancing Implant Through Pre-Formed Corneal Incision

Figure 2:
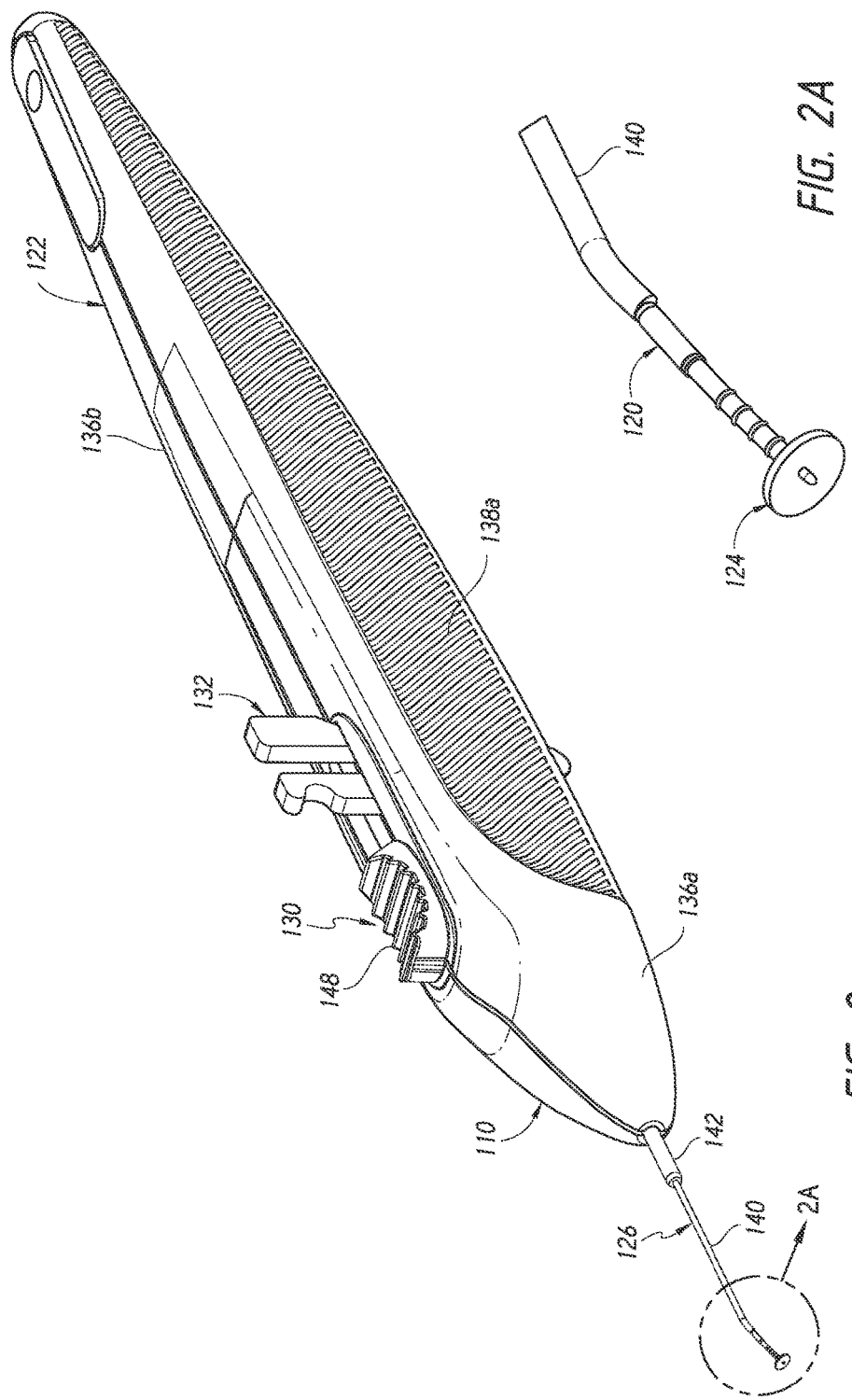
FIG. 2 is a simplified perspective view of an implant delivery device preloaded with an ocular implant (which is shown in detail in FIG. 2A), illustrating features and advantages in accordance with certain embodiments.
Figure 3:
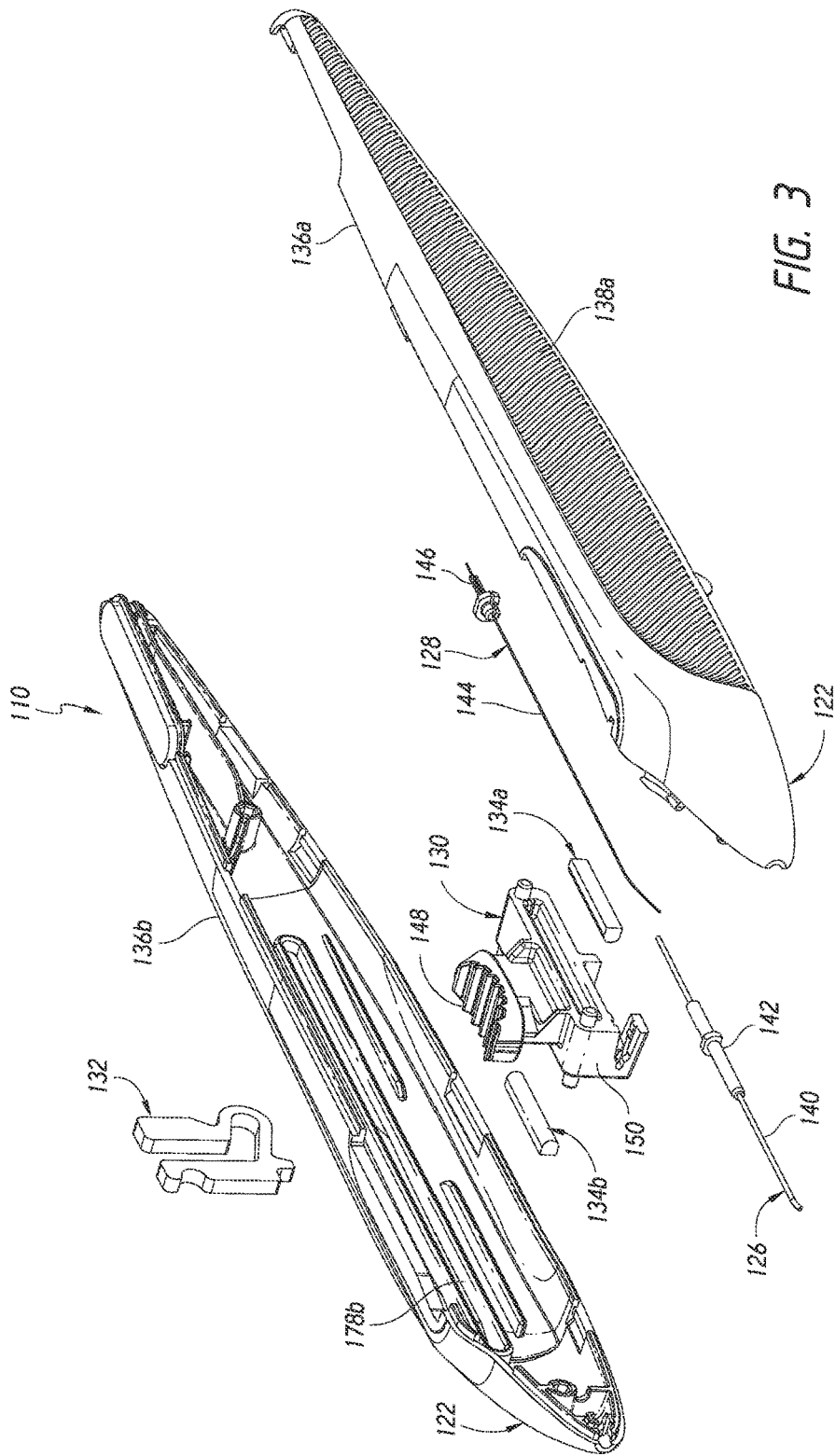
FIG. 3 is a simplified exploded perspective view of the implant delivery device of FIG. 2 illustrating features and advantages in accordance with certain embodiments.
Figure 4:
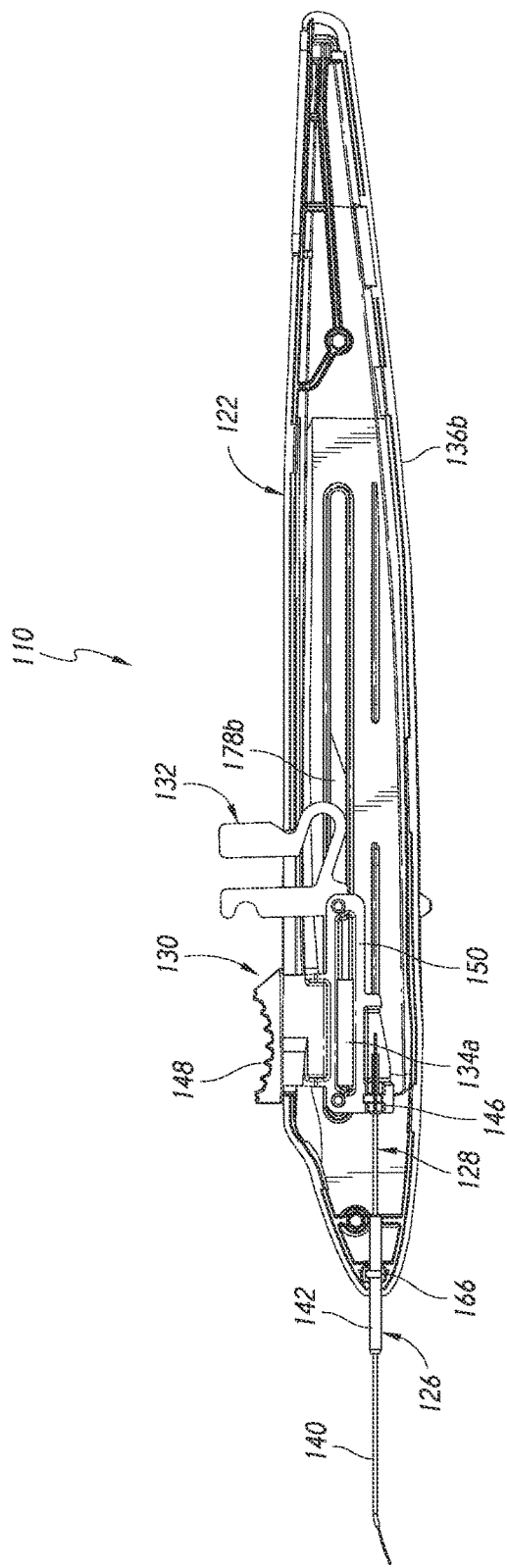
FIG. 4 is a simplified partially cut-off side view of the implant delivery device of FIG. 2 illustrating features and advantages in accordance with certain embodiments.

FIGS. 2-4 show different views of an implant delivery device or applicator 110, preloaded with an ocular implant 120, in accordance with some embodiments. The delivery device 110 is configured to implant at least a portion of the implant 120 in the suprachoroidal space 34 of the eye 10. In some embodiments, the delivery method is performed via an ab intern insertion procedure, in some embodiments, the implant delivery method is performed in combination with other ocular surgery, such as cataract surgery, and the implant is delivered through a preformed incision in the cornea or at the corneal limbus, which may be formed in conjunction with the other ocular surgery. The incision may be a self-sealing incision to facilitate quick recovery without requiring sutures in some embodiments, the ocular implant 120 is not preloaded within delivery device 110 (e.g., not preloaded in packaging at time of shipping).

The implant delivery device 110 can be provided in a sterile packaging for single-use operation. For example, a double polythene bag may be used for sterility purposes, in combination with a blister packaging to facilitate use by the operator while still maintaining safe usage.

The delivery device 110 is generally elongate in structure, and generally comprises an outer housing and handpiece 122, an implant retainer 124 (see FIG. 2A), an insertion sleeve, tube or needle assembly 126, a trocar assembly 128, a trocar trigger 130, a trigger safety device 132 and a pair of reuse prevention structures 134a and 134b.

The outer housing 122 encloses various componentry of the delivery device 110 and can comprise two housing portions such as a left housing portion 136a and a right housing portion 136b, which can be attached during fabrication of the delivery device 110.

Selected portions of the outer housing and handpiece 122 have ergonomic features such as the hand grip area 138a, which has a ribbed texture or the like to facilitate manual handling by a surgeon, medical operator or practitioner to similar hand grip area may be provided on the right housing portion 136b). Various internal structures of the outer housing 122 engage the other components of the delivery device 110, as discussed further below.

The outer housing 122 can efficaciously be fabricated from various suitable materials, as required or desired. In one non-limiting embodiment, the outer housing 122 comprises a thermoplastic material such as medical grade polycarbonate that is gamma stable.

The outer housing 122 can efficaciously be dimensioned in various suitable manners, as required or desired. In one non-limiting embodiment, the outer housing 122 has a length of about 5.60 inches, though other lengths may also be efficaciously utilized, for example, based on the size of the user's hand (e.g., between about 4 inches and about 8 inches or any length in between).

The implant retainer 124 (see FIG. 2A) is a generally disc shaped structure that is removably mounted on a distal tip of the trocar assembly 128 just distally of the implant 120. The implant retainer 124 is removed before the delivery device 110 is used. The implant retainer 124 may prevent undesirable movement of the implant 120 and prevent the implant 120 from sliding off the distal tip of the trocar assembly 128 during packaging, shipping and travel of the implant delivery device 110. The implant retainer 124 can efficaciously be fabricated from various suitable materials, as required or desired. In one non-limiting embodiment, the implant retainer 124 comprises molded silicone.

The insertion sleeve assembly 126 generally comprises an insertion sleeve 140 and a support member 142 fixedly attached thereto and to the outer housing 122. The insertion sleeve 140 may comprise a sleeve, tube or needle. The support member 142 may comprise a sleeve. Distal portions of the insertion sleeve 140 and support member 142 are exposed and extend beyond the distal tip of the delivery device 110 while proximal portions of the insertion sleeve 140 and support member 142 are contained within the outer housing 122. The insertion sleeve assembly 126 is discussed in further detail later herein.

The trocar assembly 128 generally comprises an obturator, or trocar, 144 and a trocar support member 146 attached thereto. The trocar support member 146 is mechanically coupled, connected or attached to the actuatable trocar trigger 130. In one embodiment, the trocar support member 146 is a clip, as illustrated in FIGS. 2-4. A substantial portion of the trocar 144 can extend through the insertion sleeve 140 with a distal portion extending beyond the insertion sleeve 140 on which the implant 120 is located. A proximal portion of the trocar 144 and the trocar support member 146 are contained within the outer housing 122. The trocar assembly 128 is discussed in further detail later herein.

The trocar trigger 130 generally comprises an upper finger or thumb actuatable portion 148 and a lower main body portion 150. The actuatable trigger portion 148 generally extends above the housing 122 while the main body portion 150 is generally contained within the housing 122. Before use, the trocar trigger 130 is in a forward position and, when in use, it is utilized to retract the trocar 144. The trigger main body portion 150 is mechanically coupled, connected or attached to the trocar assembly 128. The trocar trigger 130 is discussed in further detail later herein.

The trigger safety device 132 is removable and is positioned generally rearwardly with respect to the trocar trigger 130 and is mechanically coupled or engaged with the trocar trigger 130. The trigger safety device 132 prevents undesirable motion of the trocar trigger 130 during packaging, shipping and travel of the implant delivery device 110, as also discussed further below. In one embodiment, the trigger safety device 132 is a clip.

The reuse prevention structures 134a and 134b are mounted on each side of the trocar trigger 130 and within the outer housing 122. The reuse prevention structures 134a and 134b may advantageously provide a safety function to disallow reuse of the delivery device 110 so as to prevent any cross-contamination between unauthorized reuse of the single use device 110. As discussed further below, the reuse prevention structures 134a and 134b, in one embodiment, are glue blocks or preform structures that are adapted to melt, dissolve or otherwise shrink or disappear when any unapproved re-sterilization of the delivery device 110 is attempted and lock or jam the trocar trigger 130 so that its movement is thwarted. In some embodiments, a hot melt adhesive is used to freeze the trigger mechanism and prevent use after autoclave.

FIGS. 5-8 show different views of the ocular implant, stunt or shunt 120 in accordance with some embodiments. The implant 120 generally comprises an elongate implant body 151 and a proximal implant sleeve 152. The implant 120 and/or the implant body 151 comprises a lumen, channel, pathway or passage 154 extending therethrough for drainage of fluid (e.g., aqueous) from the anterior chamber 32 to the suprachoroidal space 34 and a plurality of generally circumferential retention features or structures, ribs, rings or anchors 156 to facilitate implantation and retention and/or stability in the suprachoroidal space 34. In the illustrated embodiment, the implant 120 comprises four retention features; however, other numbers of retention features may be used (e.g., two, three, five, six, seven, eight or more).

The implant 120 and/or the implant body 151 further comprises respective distal and proximal ribs, flanges or stops 158 and 160 which may hold the sleeve 152 in place. Moreover, the proximal structure 160 is dimensioned so that the implant cannot move rearwardly with respect to the distal end of the insertion sleeve 140. Thus, the insertion sleeve 140 can act as a backing tube to react against a proximal end of the implant 120 during removal of the implant 120 from the delivery device 110.

Advantageously, the implant 120 and/or the implant body 151 has a predetermined curvature and/or flexibility that substantially matches the curvature of the sclera and/or facilitates proper insertion in the suprachoroidal space 34. In some embodiments, the curvature of the implant 120 is configured to keep pressure on the sclera during implantation and prevent "understeer" and/or choroid penetration. In some embodiments, the curvature of implant is greater than a diameter of the eye (e.g., greater than 1 inch). The lumen 154, in accordance with certain embodiments, allows for drainage or flow of fluid (e.g., aqueous) from the anterior chamber 32 to the suprachoroidal space 34. The length of the implant 120 can range from about 1 mm to about 8 mm (e.g., 1 mm, 2 mm, 3 mm, 4 mm, 5 mm, 6 mm, 7 mm, 8 mm).

The implant 120 can efficaciously be fabricated from various suitable materials, as required or desired. In one non-limiting embodiment, the implant body 151 comprises a plastic, such as polyethersulfone (PES), and the sleeve 152 comprises a metal or alloy, such as titanium or a titanium alloy. In some embodiments, the sleeve 152 provides a visual aid in determining the proper depth of stent placement during implantation (e.g., one or more radiopaque markers).

The implant 120, in some embodiments, can also comprise a therapeutic agent or drug. For example, at least a portion of the implant 120 is coated with a therapeutic agent or drug. In one embodiment, at least the implant lumen 154 is coated with a therapeutic agent or drug, such as, but not limited to, heparin or the like.

The implant 120 can be efficaciously dimensioned in various suitable manners, as required or desired. In one non-limiting embodiment, the radius of curvature $R_8$ is about 1 inch, the diameter $D_8$ is about at least 0.0063 inches, and the diameter $D_5$ is about at least 340 microns. In some embodiments, the curvature is larger than the diameter of the eye (e.g., larger than 1 inch) to maintain pressure on the sclera during implantation. The implant 120 can be symmetrically designed such that it may be used in either the left or right eye. Other implants can be delivered by the delivery devices 110, 210 in addition to the implant 120.

Figure 9:
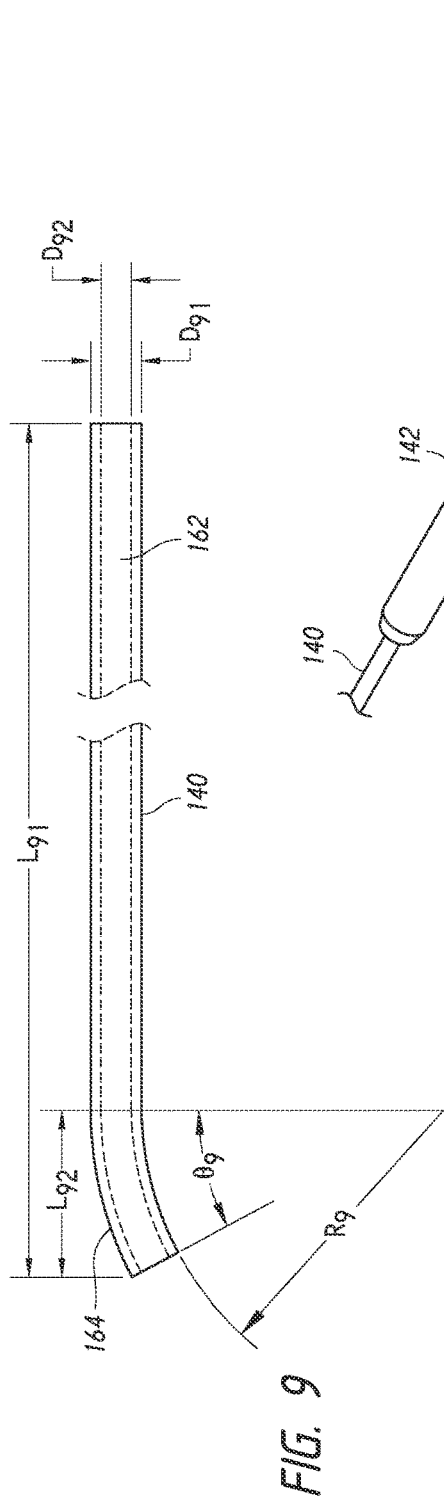
FIG. 9 is a simplified side view of an insertion sleeve of the implant delivery device of FIG. 2 illustrating features and advantages in accordance with certain embodiments.
Figure 10:
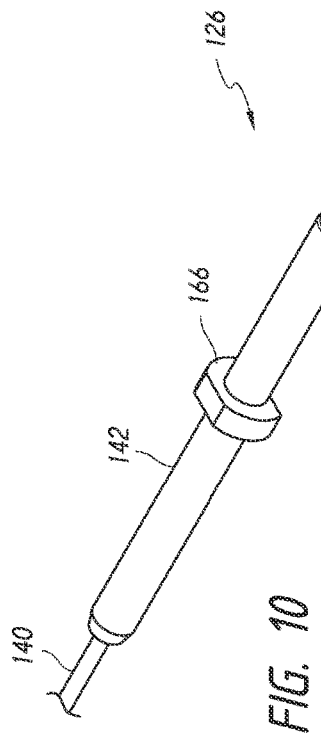
FIG. 10 is a simplified perspective view of an insertion sleeve assembly of the implant delivery device of FIG. 2, including the insertion sleeve of FIG. 9, illustrating features and advantages in accordance with certain embodiments.
Figure 11:
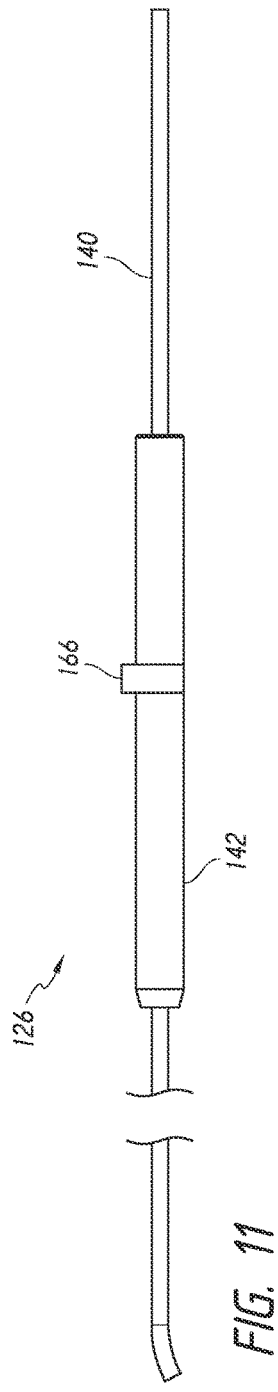
FIG. 11 is a simplified side view of the insertion sleeve assembly of FIG. 10 illustrating features and advantages in accordance with certain embodiments.

FIGS. 9-11 show different views of the insertion sleeve assembly 126 and insertion sleeve 140 in accordance with some embodiments. The insertion sleeve 140 is a generally elongated tubular structure with a lumen 162 extending therethrough and a distal curved or non-linear portion 164 to desirably-facilitate ab interno suprachoroidal implantation.

The insertion sleeve support 142 is an elongated member through which a portion of the insertion sleeve 140 extends and is fixedly attached thereto. The insertion sleeve support 142 includes a collar 166 which mates with a corresponding portion of the outer housing 122 to fixedly attach these structures.

The insertion sleeve 140 receives a portion of the trocar 144 which passes through the sleeve lumen 162. The sleeve distal curved or non-linear portion 164 advantageously provides proper curvature and alignment of the trocar 144 and/or the implant 120 for suprachoroidal implantation.

The insertion sleeve assembly 126 can efficaciously be fabricated from various suitable materials, as required or desired. In one non-limiting embodiment, the insertion sleeve 140 and sleeve support 142 comprise a liquid crystal polymer or thermoplastic such as polycarbonate which are molded to form the assembly. In another non-limiting embodiment, the insertion sleeve 140 and sleeve support 142 comprise stainless steel and are welded (spot or continuous) to form the assembly. The insertion sleeve 140 can efficaciously comprise 26±5 gauge hypodermic tubing, as required or desired, including 21, 22, 23, 24, 25, 26, 27, 28, 29, 30 and 31 gauge.

The insertion sleeve assembly 126 can be efficaciously dimensioned in various suitable manners, as required or desired. In one non-limiting embodiment, the length $L_{91}$ is about 1.8 inches, the length $L_{92}$ is about 0.06 inches, the diameter $D_{91}$ is about 0.018 inches, the diameter $D_{92}$ is about 0.001 inches, the radius of curvature $R_9$ is about 0.11 inches, and the angle $\theta_9$ is about 28° (degrees).

FIGS. 12-15 show different views of the trocar assembly 128, in accordance with some embodiments. The obturator, or trocar, 144 is a generally elongated structure with a curved or non-linear distal portion 168 having a distal-most end 170 that is configured to optimally penetrate ocular tissue so as to access the suprachoroidal space 34. In one embodiment, the distal-most end is rounded to glide smoothly down the sclera while still being adapted to dissect and separate the ciliary muscle attachment in order to enter the suprachoroidal space 34 atraumatically. In one embodiment, the distal-most end is adapted to puncture through a fibrous band at the anterior chamber angle to enter the suprachoroidal space 34.

The obturator, or trocar, 144 extends through the trocar support member 146, which is configured to engage the trocar trigger 130, and be retractable on actuation of the trocar trigger 130. The curved distal portion 168 may have a predetermined curvature to allow a proper angle of attack to penetrate ocular tissue to provide access for implantation of the implant 120 in the suprachoroidal space 34. The trocar may have slight flexibility to facilitate conformance to the eye anatomy during insertion. In one embodiment, the predetermined curvature is adapted to keep pressure on the sclera during implantation and prevent or inhibit "understeer" or choroid penetration.

In some embodiments, the trocar support member 146 is configured to mechanically engage, couple, connect or fixedly attach to a recessed portion of the trocar trigger 130. Thus, actuation or retraction of the trocar trigger 130 may result in movement and retraction of the obturator, or trocar 144.

The trocar assembly 128 can efficaciously be fabricated from various suitable materials, as required or desired. In one non-limiting embodiment, the trocar 144 comprises a metal or metal alloy such as spring tempered 304 stainless steel with a predetermined flexibility and resilience, and the trocar support member 146 comprises a metal or metal alloy such as 301 stainless steel with a predetermined hardness. The trocar 144 and trocar support member 146 can be welded together, such as, denoted by weld spots 172, or otherwise attached in other suitable manners, for example molding and the like, as needed or desired.

The trocar assembly 128 can be efficaciously dimensioned in various suitable manners, as required or desired. In one non-limiting embodiment, the radius of curvature $R_{13}$ of the trocar distal curved portion 168 is about 1 inch (which generally conforms to the implant's radius of curvature and may prevent implant creep), the diameter $D_{13}$ is about 0.006 inches (which provides a low tolerance fit within the implant's lumen), the length $L_{13}$ is about 0.17 inches, the overall unbent length of the trocar 144 is about 2.3 inches, and the radius of curvature of the trocar distal end tip 170 is in the range from about 0.001 to about 0.003 inches. In various embodiments, the radius of curvature $R_{13}$ of the trocar distal curved portion 168 can range from 0.4 inches to about 2.2 inches. In one embodiment, the curvature of the distal curved portion 168 is configured to be larger than the diameter of the eye (e.g., larger than 1 inch) in order to maintain pressure against the sclera during the implantation procedure.

Figure 16:
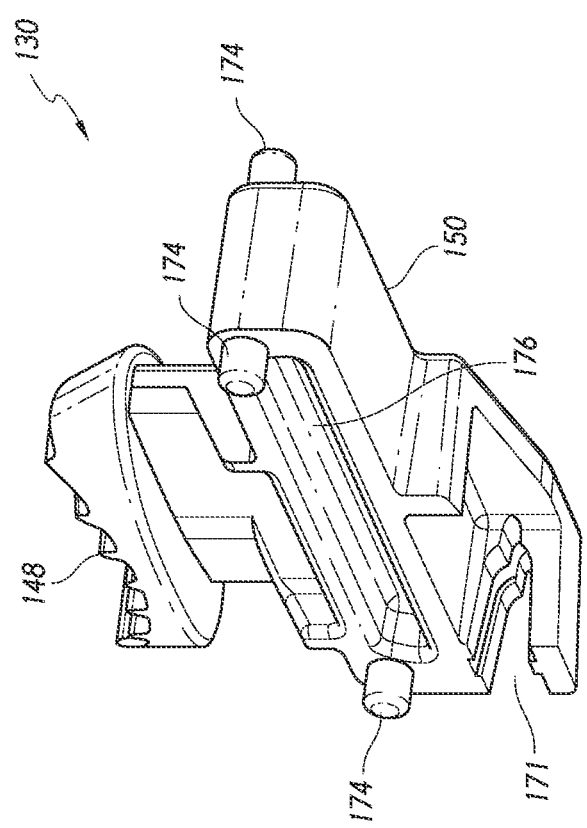
FIG. 16 is a simplified perspective view of a trocar trigger of the implant delivery device of FIG. 2 illustrating features and advantages in accordance with certain embodiments.

FIG. 16 shows a different view of the trocar trigger 130, in accordance with some embodiments. The ergonomic upper finger or thumb touch portion 148 has a ribbed texture configuration to facilitate its actuation by the operator. The lower main body portion 150 has several features that allow for the operation of the trocar trigger 130.

The trigger main body portion 150 comprises a slot, cavity, opening or recessed portion 171 which mates with and attaches to a portion of the trocar support member 146 (e.g., clip) thereby effectively coupling and connecting the trocar trigger 130 and the trocar 144. The trigger main body portion 150 may also comprise multiple pins 174 disposed generally symmetrically on either side, which slidably engage the internal structure of the outer housing 122, such as the left and right slots therein (one of which slots is depicted by reference numeral 178b in FIGS. 3 and 4).

The trigger main body portion 150 further comprises slots 176 on each side that respectively receive the reuse prevention structures 134a and 134b (e.g., glue blocks) that are mounted therein. As noted above, and discussed further herein, the glue blocks can be configured to melt, dissolve, or otherwise shrink or disappear and lock the trocar trigger 130 to prevent unapproved use for the safety of the patient. Other reuse prevention mechanisms may also be used. In some embodiments, a hot melt adhesive is used to freeze the trigger mechanism and prevent use after autoclave.

The trocar trigger 130 can efficaciously be fabricated from various suitable materials, as required or desired. In one non-limiting embodiment, the trocar trigger 130 comprises a plastic or thermoplastic, such as polyethylene.

Figure 17:
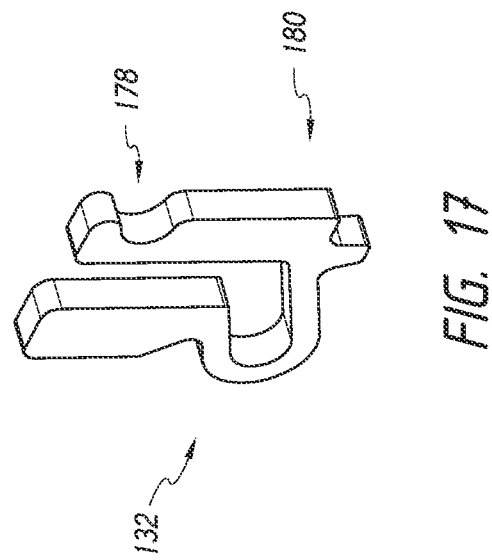
FIG. 17 is a simplified perspective view of a safety clip of the implant delivery device of FIG. 2 illustrating features and advantages in accordance with certain embodiments.

FIG. 17 shows a different view of the removable trigger safety device 132, in accordance with some embodiments. An upper portion 178 is exposed above the outer housing 122 and a lower portion 180 is contained within the outer housing 122. As shown, the trigger safety device 132 can comprise a clip mechanism.

As noted earlier, the trigger safety device 132 is configured to prevent or inhibit undesirable motion of the trocar trigger 130 during packaging, shipping and travel of the implant delivery device 110. The lower portion 180 is engaged with the trocar trigger 130 prior to use of the delivery device 110 and, by manipulation of the upper portion 178, the trigger safety device 132 is removed from the delivery device 110 prior to the surgical procedure.

The trigger safety device 132 can efficaciously be fabricated from various suitable materials, as required or desired. In one non-limiting embodiment, the trigger safety device 132 comprises a thermoplastic such as a polycarbonate, for example, Makrolon® 2458.

The delivery device 110 generally comprises, but is not limited to, materials composed of stainless steel, molded plastic and silicone, among others and equivalents thereof.

Methods of Implant Delivery Through Pre-Formed Corneal Incision

FIGS. 18-22 show some steps or acts of a surgical procedure or method of implanting the ocular implant 120 in the suprachoroidal space 34 of the eye 10 using the implant delivery device 110 in accordance with some embodiments. Given the details in the figures, the surgical method should be self-explanatory; however some textual description is provided below.

In some embodiments, a cohesive viscoelastic is added to the anterior chamber as needed, to maintain intraocular pressure for use of a gonioprism (surgeons may select a cohesive viscoelastic of their preference, including but not limited to, Heaton, Amvisc or Provise) through the incision created for implant or stent delivery or other surgery (e.g. cataract surgery).

If a gonioprism is used for visualization, the gonioprism is placed on the cornea. A surgical microscope and patient may be positioned to provide clear visualization of the trabecular meshwork on the nasal side of the eye through the gonioprism. The patient's head may be tilted as far as practical away from the surgeon, and the microscope may be tilted toward the surgeon to ensure a proper viewing angle.

In some embodiments, the anterior chamber angle is inspected using the gonioprism or other visualization member to ensure good visualization at the nasal implant location.

The implant delivery device 110 is removed from the blister tray and the implant retainer 124 is removed from the implant and trocar tip (e.g., using fine forceps) without disrupting the implant position and taking care that the implant 120 does not slide off the trocar 144.

The trigger safety device 132 may then be removed, taking care once again that the implant 120 does not slide off the trocar 144, and that the trocar trigger 130 is maintained in the forward position by the operator, and does not slide rearward.

If required, the anterior chamber can be deepened by injecting additional cohesive viscoelastic into the anterior chamber to aid in chamber maintenance. The inserter tip can be coated with a small drop of viscoelastic, as required.

Figure 18:
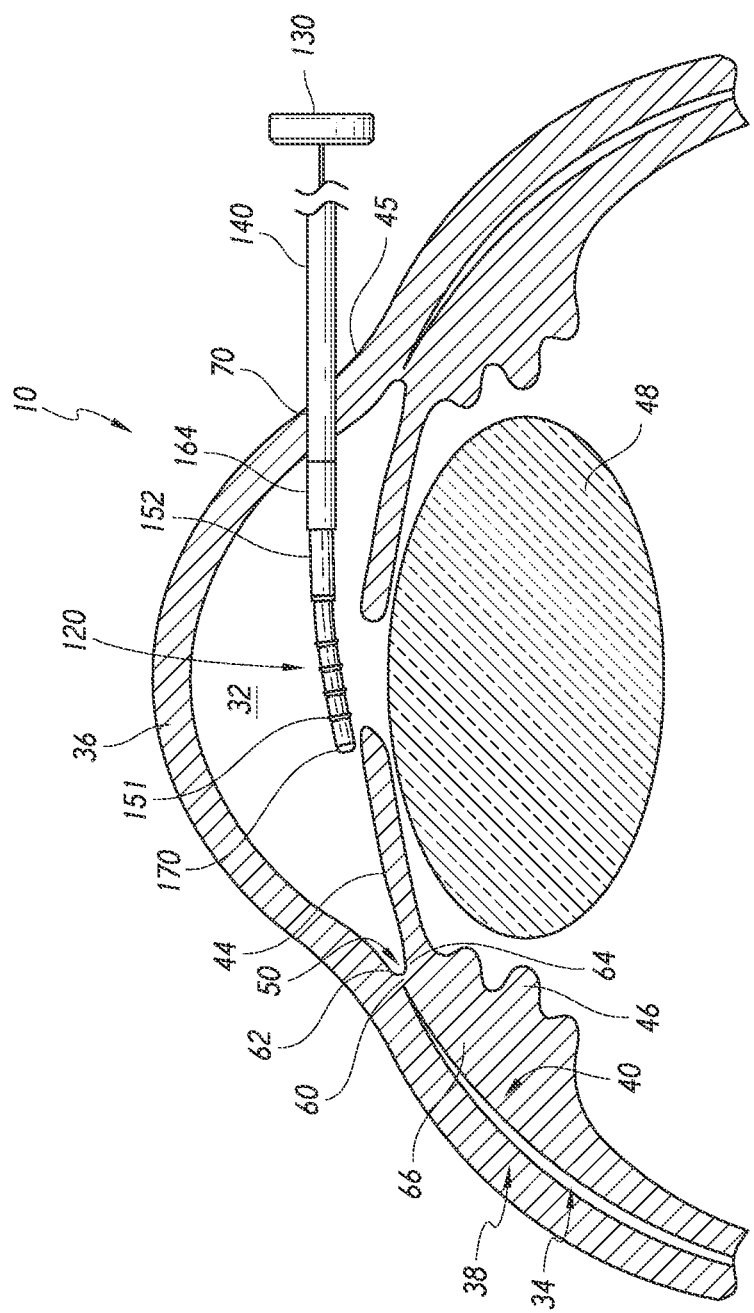

In accordance with some embodiments, the implantation procedure is performed in conjunction with another ophthalmic procedure, such as cataract surgery, and as illustrated in FIG. 18, the delivery instrument 110 with the implant 120 preloaded thereon at a distal portion thereof is introduced or inserted into the anterior chamber 32 through a preexisting or preformed corneal or limbal incision 70. The insertion sleeve 140 extends through the incision 70 and into the anterior chamber 32. The trocar trigger 130 is maintained in the forward position by the operator. The delivery device 110 may be advanced to the papillary margin before replacing the gonioprism onto the eye. In some embodiments, care is taken to avoid contact with the lens 48, cornea 36 and iris 44. Preloading the implant 120 on the delivery instrument 110 may reduce loading errors and contribute to ease of use.

Figure 19:
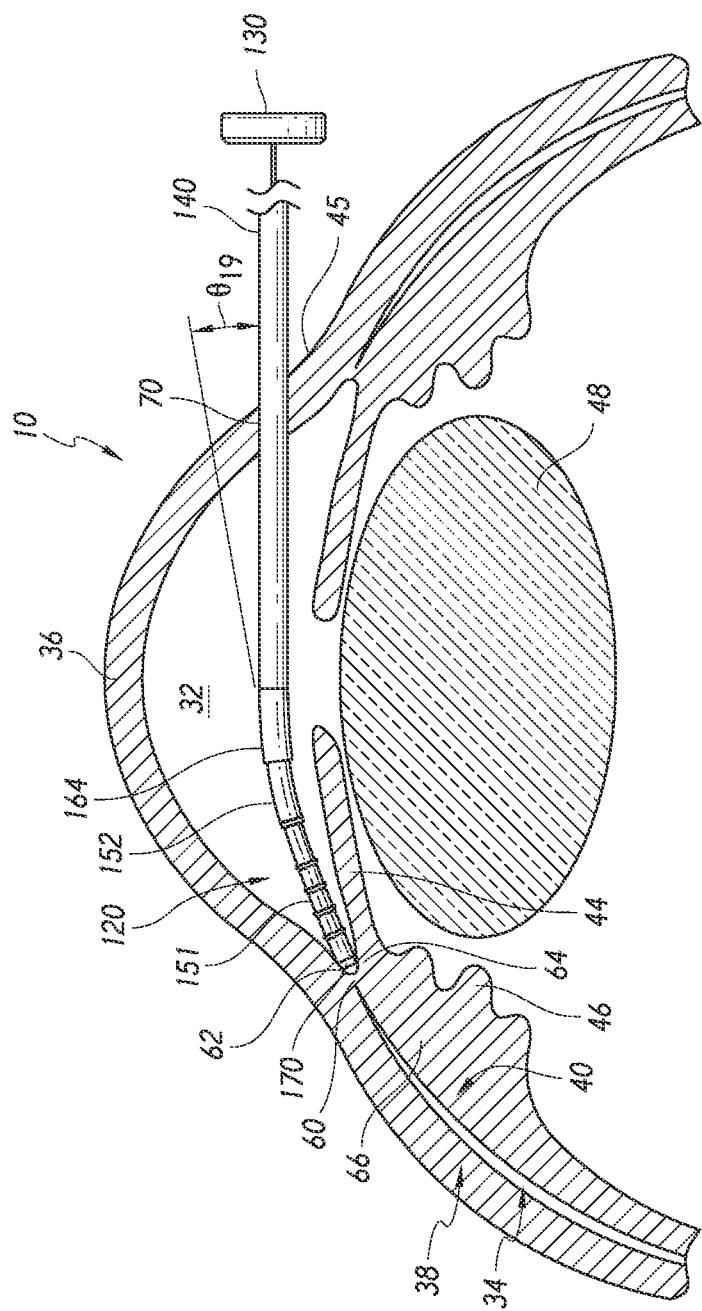

As illustrated in FIG. 19, the implant 120 may be advanced across the anterior chamber 32 to the anterior chamber angle 50 towards the scleral spur 62, until the trocar distal end 170 is adjacent the fibrous attachment zone 60. The trocar trigger 130 is maintained in the forward position by the operator, in accordance with some embodiments, the angle of attack $\theta_{19}$ is about 15° (degrees), though 10, 11, 12, 13, 14, 15, 16, 17, 18, 19 and 20° (degrees) or other attack angles may efficaciously be utilized, as needed or desired. In some embodiments, the delivery device 110 has a built-in configuration or design for a generally downward angle of about 15° (±5°-10°) (degrees) at the site of implantation or towards this site.

Figure 20:
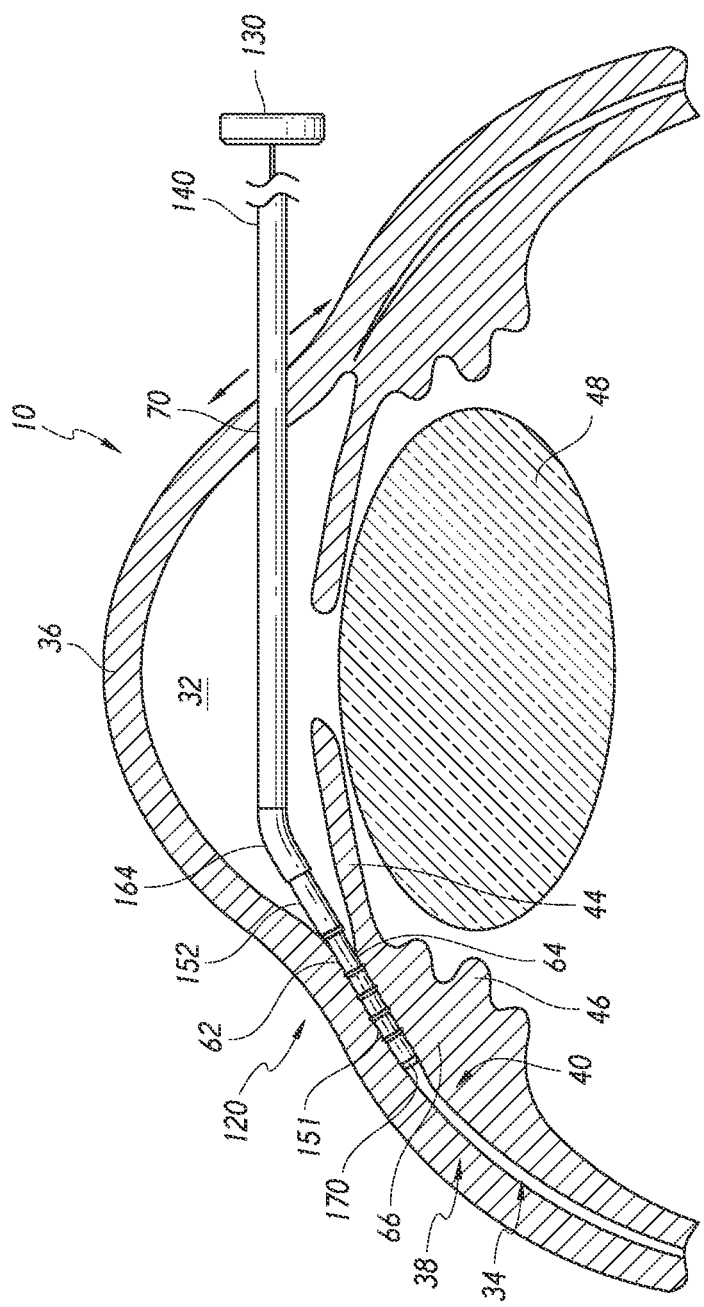

Next, as illustrated in FIG. 20, the trocar distal tip or end 170 penetrates through the tissue of and/or adjacent the fibrous attachment zone 60 and the implant 120 is advanced until its implantation position has been reached in the suprachoroidal space 34 with a predetermined portion of the implant sleeve 152 extending into the anterior chamber 32. The trocar trigger 130 is maintained in the forward position by the operator. In some embodiments, the trocar distal tip or end 170 is adapted to dissect and separate the ciliary muscle attachment in order to enter the suprachoroidal space atraumatically. In some embodiments, a generally narrow passage may be created into the suprachoroidal space by gently separating the iris processes away from the scleral spur with the tip 170 of the insertion trocar until the anterior and posterior portions of the scleral spur are substantially fully visible on a limited area e.g., create an approximately 0.5 mm to a maximum of about 1 mm width opening. The implant or stent 120 may then be advanced until the anterior surface of the implant or stent is substantially tangent to the posterior margin of the scleral spur. With finger or thumb firmly on the trocar trigger 130 in the forward position, the trocar/implant are carefully advanced into the suprachoroidal space until the implant proximal sleeve 152 just passes the scleral spur and enters the suprachoroidal space—in some embodiments, approximately half (or about 0.4 mm to about 0.7 mm) of the implant sleeve 152 remains in the anterior chamber.

In accordance with several embodiments, during implantation or insertion of the implant 120, an obturator (e.g., trocar 144) extends through the implant or stent lumen 154 to advantageously prevent tissue ingress and lumen clogging during implant insertion (e.g., prior to removal of the trocar 144 from the implant lumen 154). Moreover, advantageously, and in accordance with several embodiments, a generally rounded, and not sharp trocar or obturator tip or distal end 170 is utilized to glide smoothly down the sclera and prevent any undesirable sticking, scraping and/or attendant wound healing/fibrosis/encapsulation issues, while still being sharp enough to dissect and separate the ciliary muscle attachment in order to enter the suprachoroidal space atraumatically.

In accordance with some non-limiting embodiments, the outer diameter of the stent or implant 120 is between about 300 µm and 400 µm (e.g., 350 µm, 360 µm, 375 µm, 380 µm, 390 µm), which can advantageously avoid and/or mitigate any cyclodialysis cleft issues related with implantation. For example, in some embodiments, the delivery device 110 does not create a cyclodialysis cleft substantially larger than the implant 120 itself, and in other embodiments, does not create a cyclodialysis cleft in that the delivery device 110 and implant 120 are delivered through fibrous tissue bands of the ciliary muscle as opposed to dissecting the ciliary muscle from the sclera at the anterior chamber angle.

Figure 21:
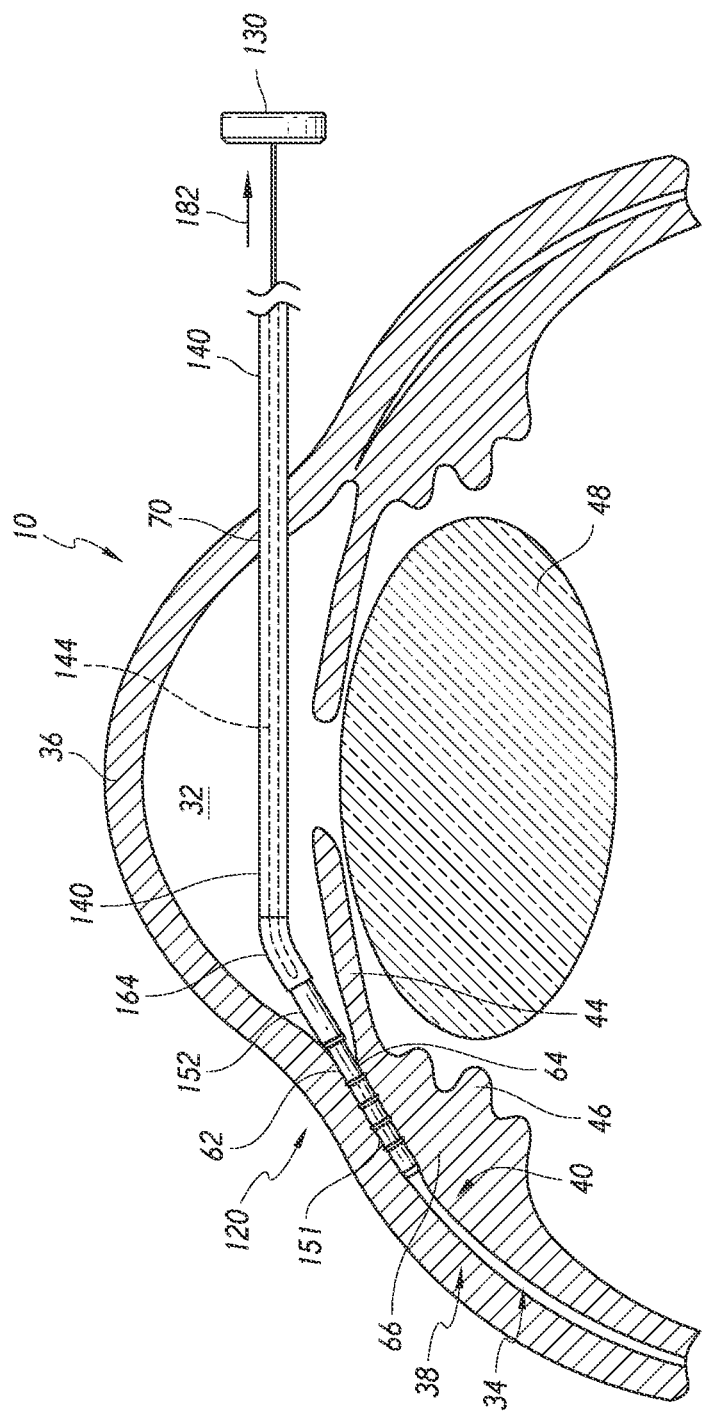

Next, as illustrated in FIG. 21, the trocar trigger 130 is moved in a rear or proximal direction 182 or position by the operator so that the trocar 144 is retracted from the implant lumen 154 and the suprachoroidal space 34. In some embodiments, once the implant or stent is in position at the proper depth, the trocar trigger button is slid backwards until the implant or stent 120 is released. In accordance with several embodiments, such a backwards movement of the trocar trigger 130 helps to inhibit or prevent deep placement of the stent or implant 120 within the suprachoroidal space. (Similar configurations can be efficaciously employed in connection with the placement of the implant 220, as needed or desired.) In some embodiments, a backing tube (e.g., insertion sleeve 140) is configured to react against a proximal end of the implant 120 during removal of the trocar 144.

Figure 22:
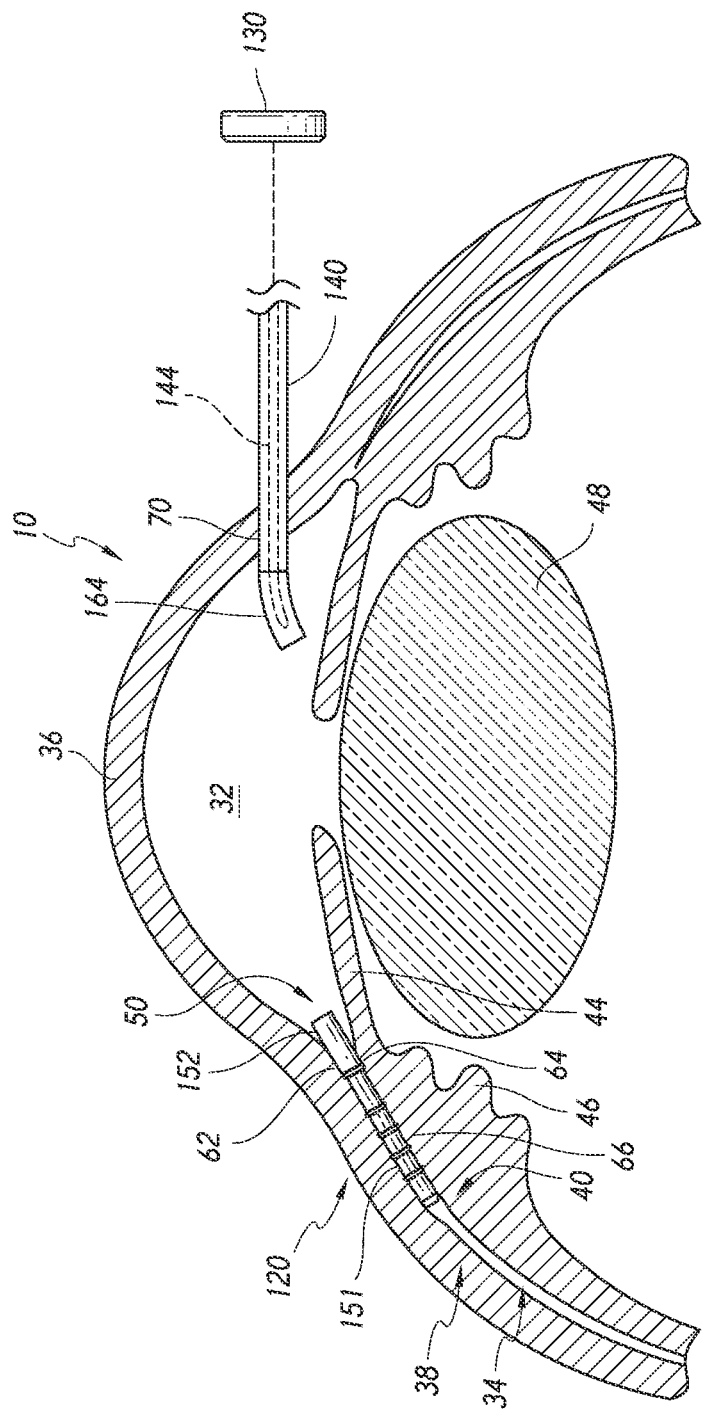

As illustrated in FIG. 22, the delivery device 110 may then be retracted and the insertion sleeve 140 can be removed from the anterior chamber 32 with the implant 120 remaining within the eye 10 and at least a portion implanted in the suprachoroidal space 34.

In some embodiments, the operator confirms that the implant is in a proper position (e.g., the proximal end rests in the anterior chamber with an unobstructed inlet) using the operating microscope and gonioprism. The anterior chamber can be irrigated and aspirated with balanced salt solution (BSS) to remove all viscoelastic. If needed, the posterior edge of the incision is pressed down to facilitate substantially complete removal of the viscoelastic. The anterior chamber can then be inflated with saline solution to achieve physiologic pressure, as required.

In some embodiments, a predetermined curvature of both (or at least one of) the implant 120 and delivery device 110 is provided to desirably keep pressure on the sclera during implantation and prevent "understeer" or choroid penetration. The delivery device 110 can be curved to maintain the implant 120 at the same curvature during the shelf life, which desirably prevents plastic creep and thus maintains the implant's or stout's curvature specification. In one non-limiting embodiment, the curvature is larger than a diameter of the eye (e.g., larger than the 1 inch) in order to maintain the pressure on the sclera.

Delivery Device for Advancing Implant Through Device-Formed Corneal Incision

Figure 23:
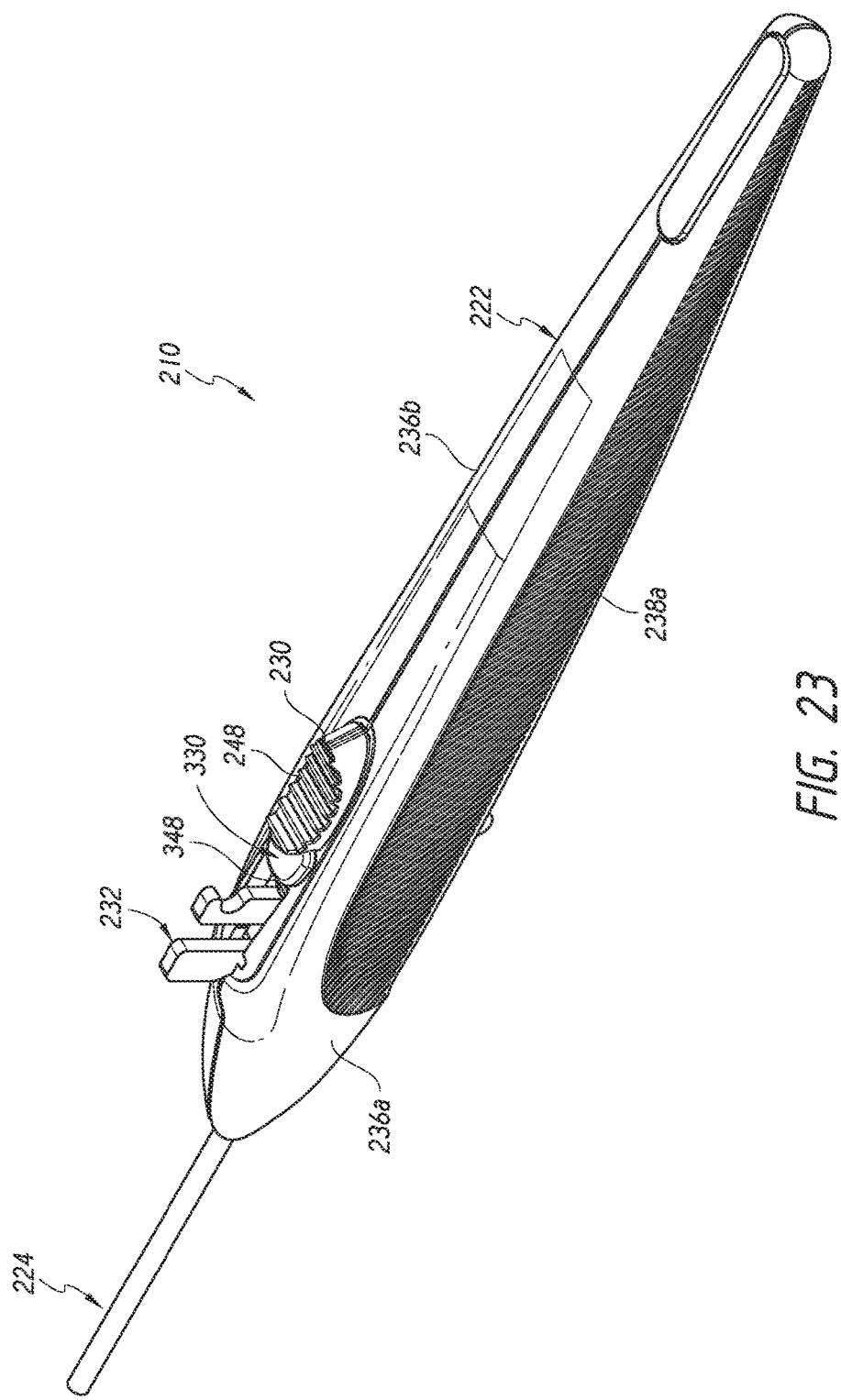
FIG. 23 is a simplified perspective view of an implant delivery device, preloaded with an ocular implant, illustrating features and advantages in accordance with certain embodiments.
Figure 24:
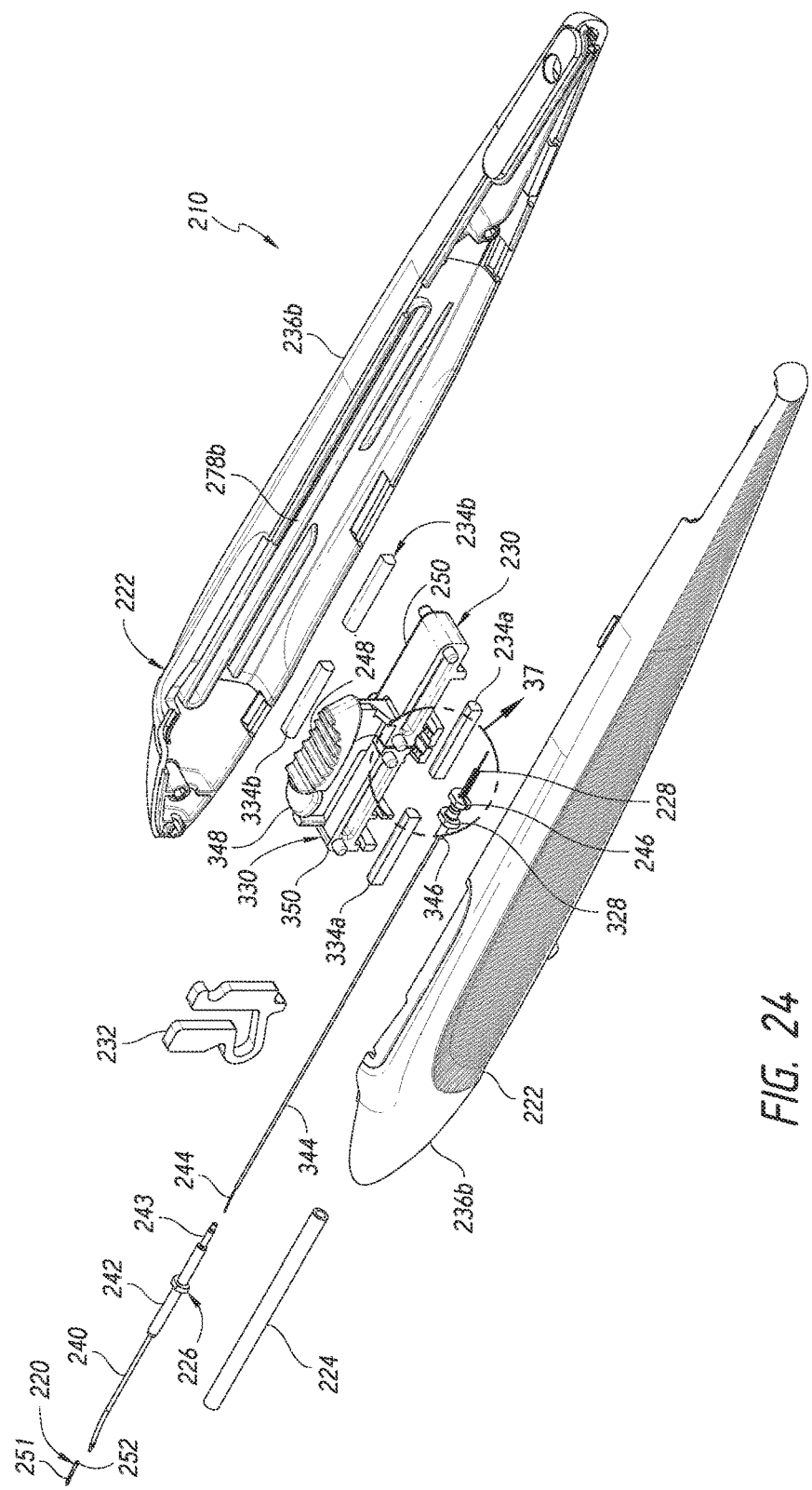
FIG. 24 is a simplified exploded perspective view of the implant delivery device, including the implant, of FIG. 23 illustrating features and advantages in accordance with certain embodiments.

FIGS. 23 and 24 show different views of an implant delivery device, inserter or applicator 210, preloaded with an ocular implant 220, in accordance with some embodiments. The delivery device 210 is configured to deliver and position the implant 220 in the suprachoroidal space 34 of the eye 10. In some embodiments, the delivery method is performed via an ab interno procedure. In some embodiments, the implant is delivered through a self-sealing corneal incision (e.g., at or near the limbus) formed by a corneal penetration needle of the delivery device 210. The implant 220 may be preloaded on or within the delivery device 210 (e.g., on art obturator, or trocar, of the delivery device 210) and provided as a kit within a single packaging. In some embodiments, the implant 220 is not preloaded on the delivery device 210 (e.g. not preloaded prior to shipping in the packaging).

The delivery device 210 can be provided in a sterile packaging for single-use operation. For example, a double polythene bag may be used for sterility purposes, in combination with a blister packaging to facilitate use by the operator while still maintaining safe usage.

The delivery device 210 is generally elongate in structure, and generally comprises an outer housing and handpiece 222, a removable protective tube 224, a cortical penetration needle assembly 226, a trocar assembly 228, a trocar trigger 230, a pusher tube assembly 328, a pusher tube trigger 330, a trigger safety device 232 and/or two pairs of reuse prevention structures 234a, 234b and 334a, 334b.

The outer housing 222 is similar to the outer housing 122 and encloses various componentry of the delivery device 210 and can comprise two housing portions such as a left housing portion 236a and a right housing portion 236b, which are attached during fabrication of the delivery device 210.

Selected portions of the outer housing 222 have ergonomic features such as the hand grip area 238a which has a ribbed texture or the like to facilitate manual handling by a surgeon, medical operator or practitioner (a similar hand grip area is provided on the right housing portion 236b). Various internal structures of the outer housing 222 engage the other components of the delivery device 210, as discussed further below.

The outer housing 222 can efficaciously be fabricated from various suitable materials, as required or desired. In one non-limiting embodiment, the outer housing 222 comprises a thermoplastic material, such as medical grade polycarbonate that is gamma stable.

The outer housing 222 can efficaciously dimensioned in various suitable manners, as required or desired. In one non-limiting embodiment, the outer housing 222 has a length of about 5.60 inches, though other lengths may also be efficaciously utilized, for example, based on the size of the user's hand (e.g., from about 4 inches to about 8 inches and any length in between).

The protective cover tube 224 may be removably mounted on a portion of the cortical penetration needle assembly 226 that extends beyond a distal end of the outer housing 222. The protective cover tube 224 may be removed before the delivery device 210 is used. One purpose of the protective cover tube 224 may be to protect the conical penetration needle assembly 226 and the components therein during packaging, shipping and travel of the implant delivery device 210.

The protective cover tube 224 can efficaciously be fabricated from various suitable materials, as required or desired. In one non-limiting embodiment, the protective cover tube 224 comprises a thermoplastic, such as low density polyethylene (LDPE).

The corneal penetration needle assembly 226 generally comprises a corneal penetration needle 240 and a support member 242 (e.g., sleeve) fixedly attached thereto and to the outer housing 222. Optionally, a seal 243 is provided to further protect the inner componentry of the delivery device 210 from undesirable fluid entrance. Distal portions of the corneal penetration needle 240 and support member 242 may be exposed and extend beyond the distal tip of the delivery device 210, while proximal portions of the corneal penetration needle 240 and support member 242 may be contained within the outer housing 222. Portions of the needle 240 may comprise a hydrophilic or hydrophobic coating. The corneal penetration needle assembly 226 is discussed in further detail later herein.

The trocar assembly 228 generally comprises an obturator, or trocar 244 and a trocar support member 246 (e.g., collar) fixedly attached thereto. The trocar support member 246 is mechanically coupled, connected or attached to the actuatable trocar trigger 230. A substantial distal portion of the trocar 244 extends through the corneal penetration needle 240 (and pusher tube) with a distal end portion also extending through the implant 220. A proximal portion of the trocar 244 and the trocar support member 246 are contained within the outer housing 222. The trocar assembly 228 is discussed in further detail later herein.

The trocar trigger 230 generally comprises an upper finger or thumb actuatable portion 248 and a lower main body portion 250. The actuatable trigger portion 248 generally extends outside the outer housing 222 while the main body portion 250 is generally contained within the outer housing 222. Before use, the trocar trigger 230 is in a rear position and, when in use, it is utilized to first advance and then retract the trocar 244. The trigger main body portion 250 is mechanically coupled, connected or attached to the trocar assembly 228. The trocar trigger 230 is also mechanically and/or operatively coupled to the pusher tube trigger 330. The trocar trigger 230 is discussed in further detail later herein.

The pusher tube assembly 328 generally comprises a pusher tube 344 and a pusher tube collar 346 fixedly attached thereto. The pusher tube collar 346 is mechanically coupled, connected or attached to the actuable pusher tube trigger 330. A substantial portion of the distal portion of the pusher tube 344 extends through the insertion needle 340, with a distal end being positioned proximal of the implant 220. A proximal portion of the pusher tube 344 and the pusher tube collar 346 are contained within the outer housing 222. The pusher tube assembly 328 is discussed in further detail later herein.

The pusher tube trigger 330 generally comprises an upper portion 348 distally proximate to the upper finger or thumb actuable trocar trigger portion 248 and a lower main body portion 350. The upper portion 348 generally extends outside the housing 222 while the main body portion 350 is generally contained within the housing 222. Before use, the pusher tube trigger 330 is in a rear position and, when in use, it is utilized to advance the pusher tube 344 (and the implant 220). The trigger main body portion 350 is mechanically coupled, connected or attached to the pusher tube device 328. The pusher tube trigger 330 is also mechanically and/or operatively coupled to the trocar trigger 230. The pusher tube trigger 330 is discussed in further detail later herein.

The trigger safety member 232 (e.g., clip) may be removable and positioned generally forwardly with respect to the pusher tube trigger 330. The trigger safety member 232 is mechanically coupled or engaged with the pusher tube trigger 330. In some embodiments, the trigger safety member 232 inhibits undesirable motion of the pusher tube trigger 330 and the trocar trigger 230 during packaging, shipping and travel of the implant delivery device 210. The trigger safety member 232 may be substantially the same in structure as the trigger safety device 132 discussed above.

The reuse prevention structures 234a, 234b and 334a, 334b may be mounted on each side of the trocar trigger 230 and the pusher tube trigger 330 respectively, and within the outer housing 222. The reuse prevention structures 234a, 234b and 334a, 334b advantageously provide a safety function to disallow reuse of the delivery device 210 so as to prevent any cross-contamination between unauthorized reuse of the single use device 210. In some embodiments, the reuse prevention structures 234a, 2341b and 334a, 334b comprise glue blocks or preforms that are adapted to melt or dissolve when any unapproved re-sterilization of the delivery device 210 is attempted and lock or jam the trocar trigger 230 and the pusher tube trigger 330 so that their movement is thwarted. In some embodiments, a hot melt adhesive is used to freeze the trigger mechanism and prevent use after autoclave.

The implant 220 has an implant body 251 with a proximal sleeve 252 and is located within a distal end portion of the insertion needle 240 when the delivery device 210 is loaded with the implant prior to packaging and storage or before use. The implant 220 is substantially the same in structure as the implant 120 discussed above.

FIGS. 25-40 show different views of the insertion or corneal penetration needle assembly 226 and insertion or corneal penetration needle 240 in accordance with some embodiments. The insertion needle 240 is a generally elongated tubular structure with a lumen 262 extending therethrough and a distal curved or non-linear portion 264 to desirably facilitate ab interim suprachoroidal implantation. The insertion needle 240 has a distal end cutting tip 265 which allows corneal penetration by the device to desirably form a self-sealing incision in the cornea (e.g., at or adjacent the limbus). The cutting tip 265 is advantageously sized, shaped and dimensioned to form such a self-sealing incision.

The insertion needle support 242 is an elongated member through which a portion of the needle 240 extends and is attached thereto. The insertion needle support 242 may include a collar 266 that mates with a corresponding portion of the outer housing 222 to fixedly attach these structures.

A seal 243 is mounted on a proximal end portion of the insertion needle 240. The seal 243 may advantageously protect the inner componentry of the delivery device 210 from undesirable fluid entrance and may engage an internal structure of the delivery device 210 and/or housing 222. The insertion or corneal penetration needle 240 may comprise a hydrophilic or hydrophobic coating along at least a portion of its length.

The insertion needle 240 receives a portion of the pusher tube 344 that passes through the needle lumen 262 and contains the preloaded implant 220 distal of the pusher tube 344, which in turn receives a portion of the trocar 244. The needle distal curved or non-linear portion 264 advantageously provides proper curvature and alignment of the trocar 244 and the implant 220 for suprachoroidal implantation.

The insertion needle assembly 226 can efficaciously be fabricated from various suitable materials, as required or desired. In one non-limiting embodiment, the insertion sleeve 240 and support member 242 comprise stainless steel and are welded (spot or continuous) to form the assembly, and the seal 243 can comprise silicone or the like. The insertion or corneal penetration needle 240 can efficaciously comprise 25±5 gauge hypodermic tubing, as required or desired, including, 20, 21, 22, 23, 24, 25, 26, 28, 29 and 30 gauge.

The insertion needle assembly 226 can efficaciously be dimensioned in various suitable manners, as required or desired. In one non-limiting embodiment, the length $L_{251}$ is about 1.22 inches, the curved length $L_{252}$ is about 0.3 inches, the diameter $D_{25}$ is about 0.02 inches, the radius of curvature $R_{25}$ is about 1 inch, and the width $W_{26}$ is about 0.031 inches. The radius of curvature $R_{25}$ can have the same or substantially the same radius of curvature as the trocar 244. In some embodiments, the curvature of the insertion needle assembly 226 is adapted to be larger than a diameter of the eye (e.g., greater than 1 inch) to, for example, maintain pressure on the sclera during a delivery or implantation procedure.

Figure 31:
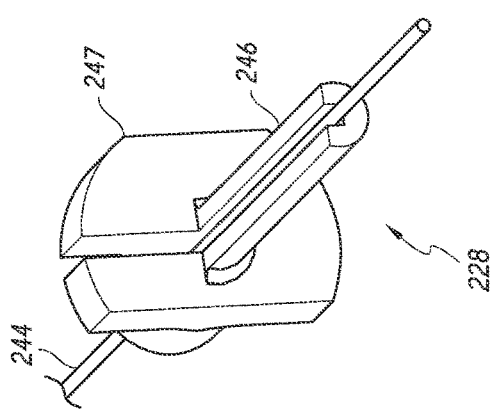
FIG. 31 is a simplified perspective view of a trocar assembly of the implant delivery device of FIG. 23 illustrating features and advantages in accordance with certain embodiments.
Figure 32:
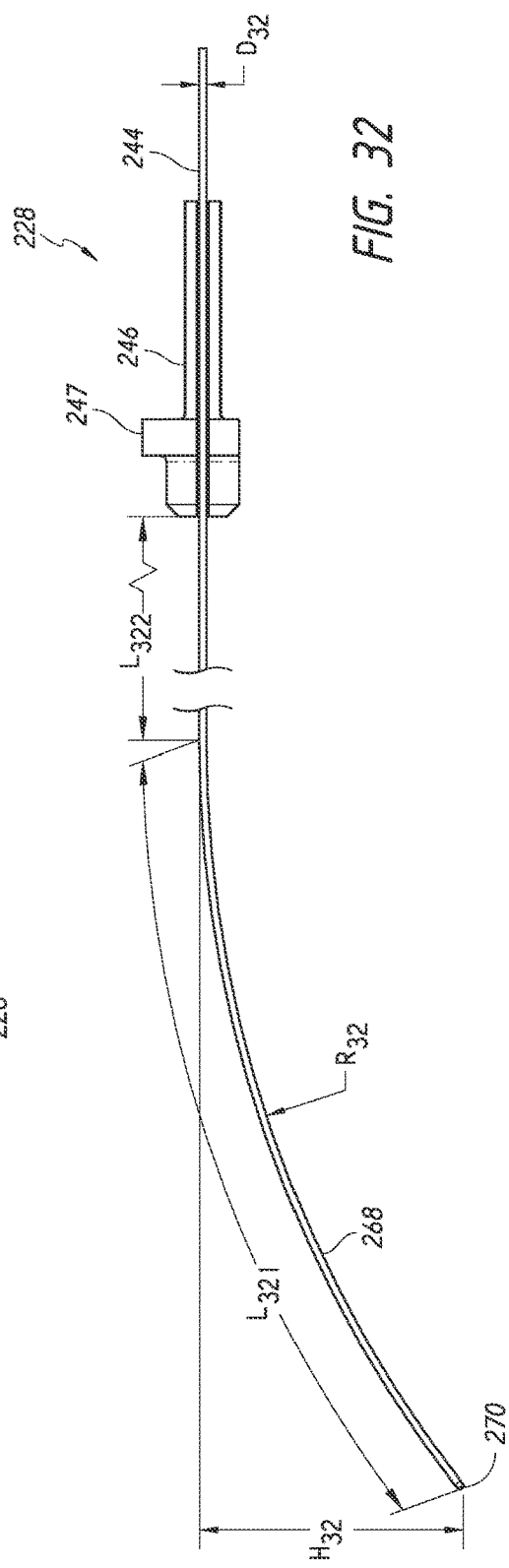
FIG. 32 is a simplified side view of the trocar assembly of FIG. 31 illustrating features and advantages in accordance with certain embodiments.

FIGS. 31 and 32 show different views of the trocar device or assembly 228, in accordance with some embodiments. The obturator, or trocar 244 is a generally elongated structure with a curved or non-linear distal portion 268 with a distal-most end 270 that is configured to optimally penetrate ocular tissue so as to access the suprachoroidal space 34.

The trocar 244 extends through the trocar support member 246, which is configured to engage the trocar trigger 230, and be advanceable and retractable on actuation of the trigger 230. The curved distal portion 268 has a predetermined curvature to allow a proper angle of attack to penetrate ocular tissue to provide access for implantation of the implant 220 in the suprachoroidal space 34.

More particularly, a collar portion 247 of the trocar support member 246 is mechanically engaged, coupled, connected or fixedly attached to a recessed portion of the trocar trigger 230. Thus, actuation, advancement or retraction of the trocar trigger 230 results in movement, advancement and retraction of the trocar 244.

The trocar assembly 228 can efficaciously be fabricated from various suitable materials, as required or desired. In one non-limiting embodiment, the trocar 244 comprises a metal or metal alloy such as spring tempered 304 stainless steel with a predetermined flexibility and resilience, and the trocar support member 246 comprises a metal or metal alloy such as 303 stainless steel with predetermined properties. The trocar 244 and trocar support member 246 (e.g., collar) can be welded together (spot or continuous welding), or otherwise attached in other suitable manners, for example molding and the like, as needed or desired.

The trocar assembly 228 can efficaciously be dimensioned in various suitable manners, as required or desired. In one non-limiting embodiment, the radius of curvature $R_{32}$ of the trocar distal curved portion 268 is about 1 inch (which generally conforms to the needle's, pusher tube's and implant's radius of curvature and prevents implant creep and disorientation), the diameter $D_{32}$ is about 0.006 inches (which provides a low tolerance fit within the implant's lumen), the curved length $L_{321}$ is about 0.67 inches, the length $L_{322}$ is about 2.1 inches, the overall unbent length of the trocar 244 is about 3.15 inches, the radius of curvature of the trocar distal end tip 270 is in the range from about 0.001 to about 0.003 inches, and the dimension $H_{32}$ is about 0.22 inches in various embodiments, the radius of curvature $R_{32}$ of the trocar distal curved portion 268 can range from 0.4 inches to about 2.2 inches. In some embodiments, the curvature of the distal curved portion 268 is adapted be slightly larger than a diameter of the eye (e.g., larger than 1 inch) to, for example, maintain pressure on the sclera during the delivery or implantation procedure. It should be appreciated, that the above non-limiting dimensions can involve that at least the trocar dimensions $H_{32}$, $R_{32}$ and/or $L_{321}$ (or other related dimensions) can reflect an after "bend" manufacturing or fabrication process or step that has been performed or implemented on the trocar 244.

Figure 33:
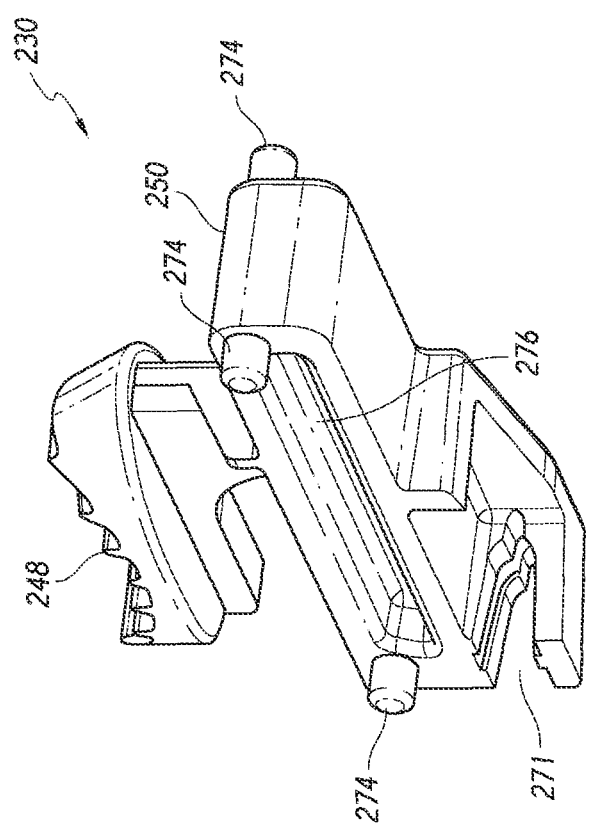
FIG. 33 is a simplified perspective view of a trocar trigger of the implant delivery device of FIG. 23 illustrating features and advantages in accordance with certain embodiments.

FIG. 33 shows a different view of the trocar trigger 230, in accordance with some embodiments. The ergonomic upper finger or thumb touch portion 248 has a ribbed texture configuration to facilitate its actuation by the operator. The lower main body portion 250 has several features that allow for the operation of the trocar trigger 230.

The trigger body portion 250 comprises a slot, cavity, opening or recessed portion 271 which mates with and attaches to a portion of the trocar collar portion 247 thereby effectively coupling and connecting the trigger 230 and the trocar 244. The trigger body portion 250 may also comprise multiple pins 274 disposed generally symmetrically on either side which slidably engage the internal structure of the housing 222 such as the left and right slots therein, one of which slots is depicted by reference numeral 278b in FIG. 24.

The trigger body portion 250 may further comprise slots 276 on each side which respectively receive the reuse prevention structures 234a and 234b that are mounted therein. The reuse prevention structures (e.g., glue blocks or preforms) may be configured to melt or otherwise dissolve or degrade and lock the trocar trigger 230 to prevent unapproved use for the safety of the patient. In some embodiments, a hot melt adhesive is used to freeze the trigger mechanism and prevent use after autoclave.

The trocar trigger 230 can efficaciously be fabricated from various suitable materials, as required or desired. In one non-limiting embodiment, the trocar trigger 230 comprises a plastic or thermoplastic, such as polyethylene.

Figure 34:
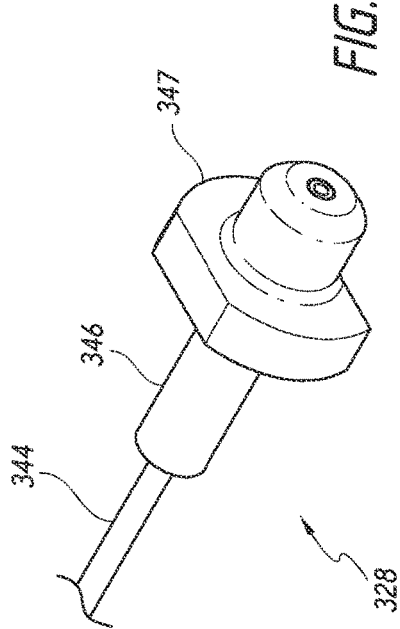
FIG. 34 is a simplified perspective view of a pusher tube assembly of the implant delivery device of FIG. 23 illustrating features and advantages in accordance with certain embodiments.
Figure 35:
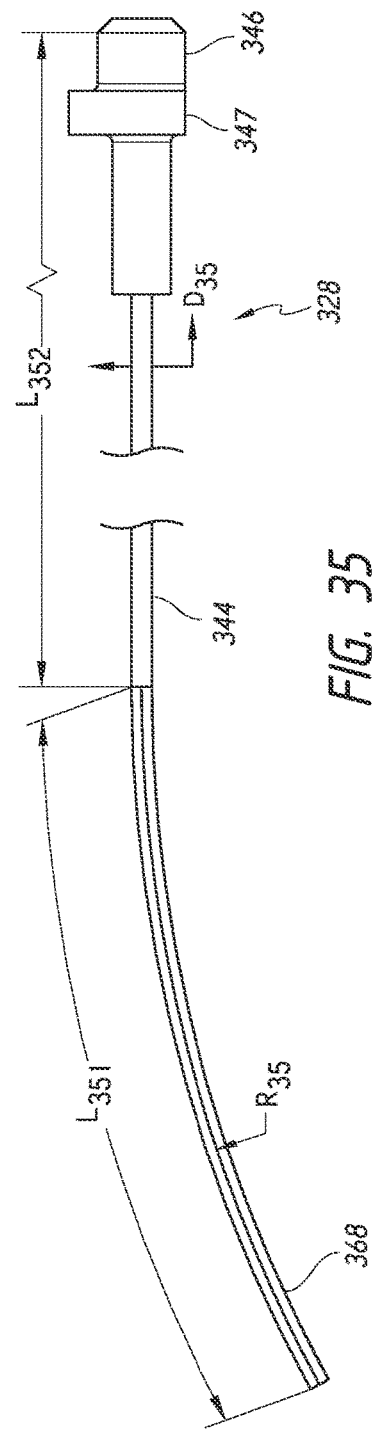
FIG. 35 is a simplified side view of the pusher tube assembly of FIG. 34 illustrating features and advantages in accordance with certain embodiments.

FIGS. 34 and 35 show different views of the pusher tube assembly 328, in accordance with some embodiments. The pusher tube 344 is a generally elongated structure with a curved or non-linear distal portion 368.

The pusher tube 344 extends from the pusher tube support member 346 that is configured to engage the pusher tube trigger 330, and be advanceable on actuation of the trigger 330, and desirably be lockable thereafter, in some embodiments. The curved distal portion 368 may have a predetermined curvature to allow a proper angle of attack for the trocar 244 to penetrate ocular tissue to provide access for implantation of the implant 220 in the suprachoroidal space 34. The predetermined curvature may be configured to match the curvature of the sclera.

More particularly, a collar portion 347 of the pusher tube collar 346 mechanically engages, couples, connects or fixedly attaches to a recessed portion of the pusher tube trigger 330. Thus, actuation and advancement of the pusher tube trigger 330 results in movement and advancement of the pusher tube 344.

The pusher tube assembly 328 can efficaciously be fabricated from various suitable materials, as required or desired. In one non-limiting embodiment, the pusher tube 344 comprises nitinol tubing, and the pusher tube collar 346 comprises nitinol bar stock. The pusher tube 344 and collar 346 can be welded together (spot or continuous welding), or otherwise attached in other suitable manners, for example molding and the like, as needed or desired.

The pusher tube assembly 328 can efficaciously be dimensioned in various suitable manners, as required or desired. In one non-limiting embodiment, the radius of curvature $R_{35}$ of the pusher tube distal curved portion 368 is about 1 inch (which generally conforms to the needle's, trocar's and implant's radius of curvature and prevents implant creep and disorientation), the diameter $D_{35}$ is about 0.014 inches (which provides a low tolerance fit within the needle's lumen), the curved length $L_{351}$ is about 0.5 inches, the length $L_{352}$ is about 2.1 inches, and the overall unbent length of the pusher tube 344 is about 2.57 inches. In various embodiments, the radius of curvature $R_{35}$ of the pusher tube distal curved portion 368 can range from 0.4 inches to about 2.2 inches, in some embodiments, the curvature of the pusher tube distal curved portion 368 is adapted to be slightly larger than a diameter of an eye (e.g., greater than 1 inch), for example, maintain pressure on the sclera during the delivery or implantation procedure. It should be appreciated, that the above non-limiting dimensions can involve that at least the pusher tube dimensions $L_{351}$ and/or $R_{35}$ (or other related dimensions) can reflect an after "bend" manufacturing or fabrication process or step that has been performed or implemented on the pusher tube 344.

Figure 36:
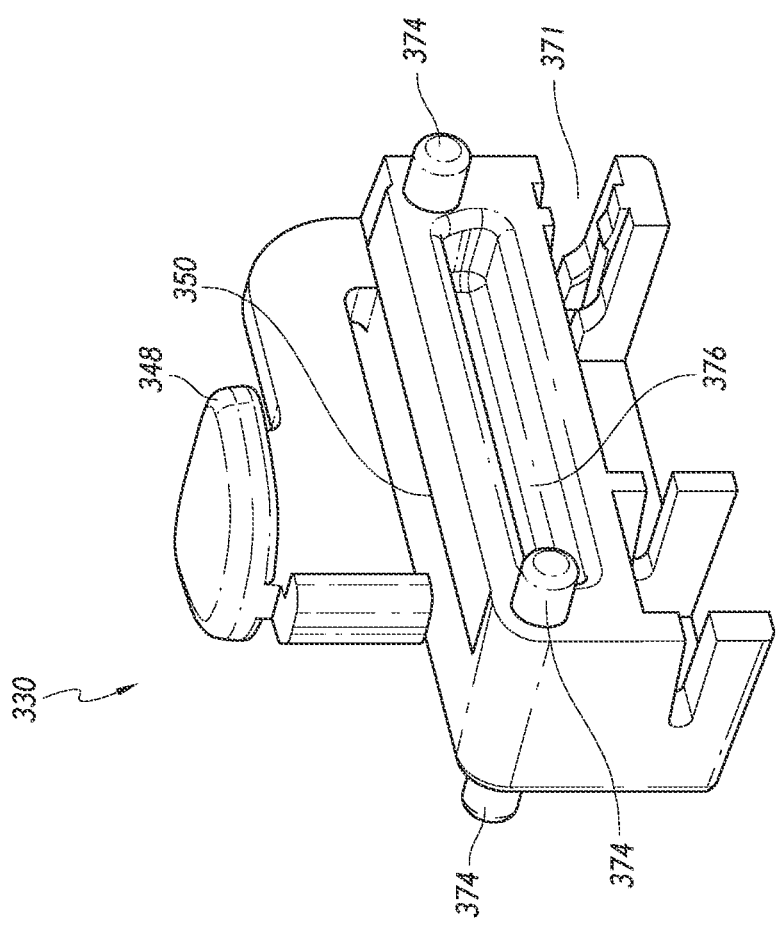
FIG. 36 is a simplified perspective view of a pusher tube trigger of the implant delivery device of FIG. 23 illustrating features and advantages in accordance with certain embodiments.

FIG. 36 shows a different view of the pusher tube trigger 330, in accordance with some embodiments. The upper trigger portion 348 is distally disposed of the trocar trigger portion 248 and actuable with movement of the same. The lower main body portion 350 has several features that allow for the operation of the pusher tube trigger 330.

The trigger main body portion 350 may comprise a slot, cavity, opening or recessed portion 371 that mates with and attaches to a portion of the pusher tube collar portion 347, thereby effectively coupling and connecting the trigger 330 and the pusher tube 344. The trigger body portion 350 may also comprise multiple pins 374 disposed generally symmetrically on either side that slidably engage the internal structure of the housing 222 such as the left and right slots therein (one of which slots is depicted by reference numeral 278b in FIG. 24.)

The trigger main body portion 350 may further comprise slots 376 on each side which respectively receive the reuse prevention structures 334a and 334b that are mounted therein. The reuse prevention structures 334a and 334b are adapted to prevent unapproved use for the safety of the patient.

The pusher tube trigger 330 can efficaciously be fabricated from various suitable materials, as required or desired. In one non-limiting embodiment, the pusher tube trigger 330 comprises a plastic or thermoplastic such as polyethylene.

Figure 37:
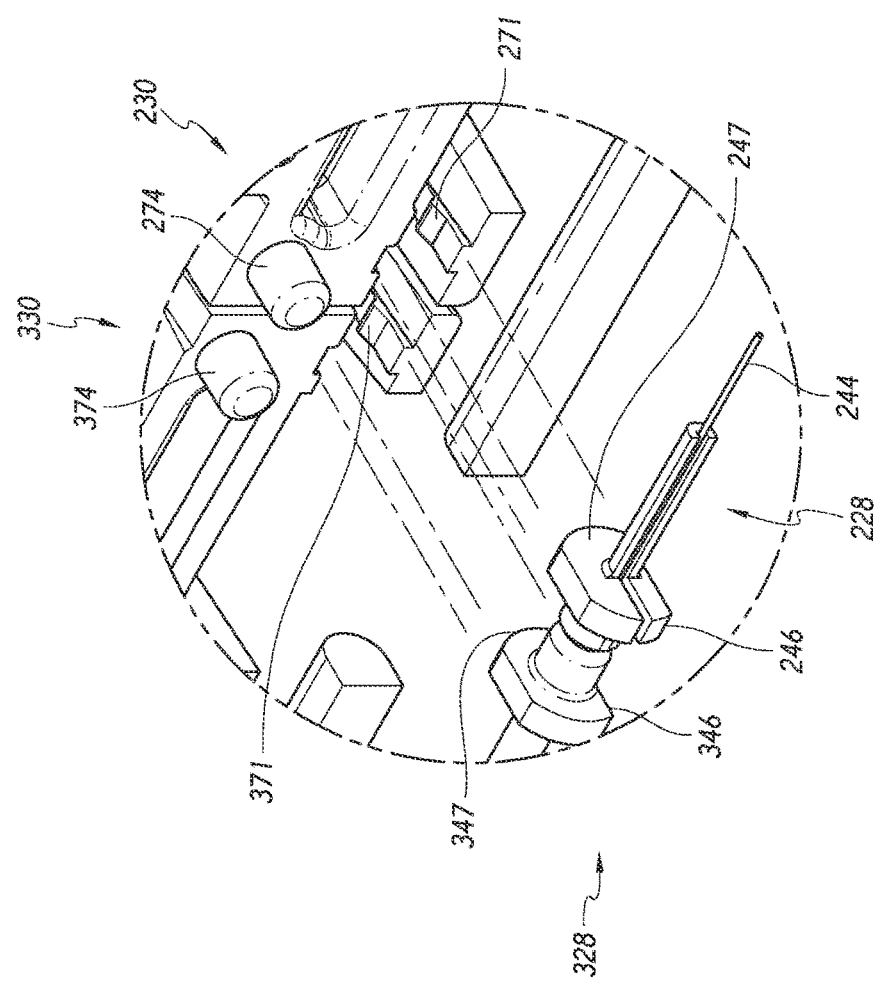
FIG. 37 is a simplified perspective detail view from FIG. 24 of the engagement between a collar of the trocar assembly and the trocar trigger and between a collar of the pusher tube assembly and the pusher tube trigger illustrating features and advantages in accordance with certain embodiments.
Figure 38:
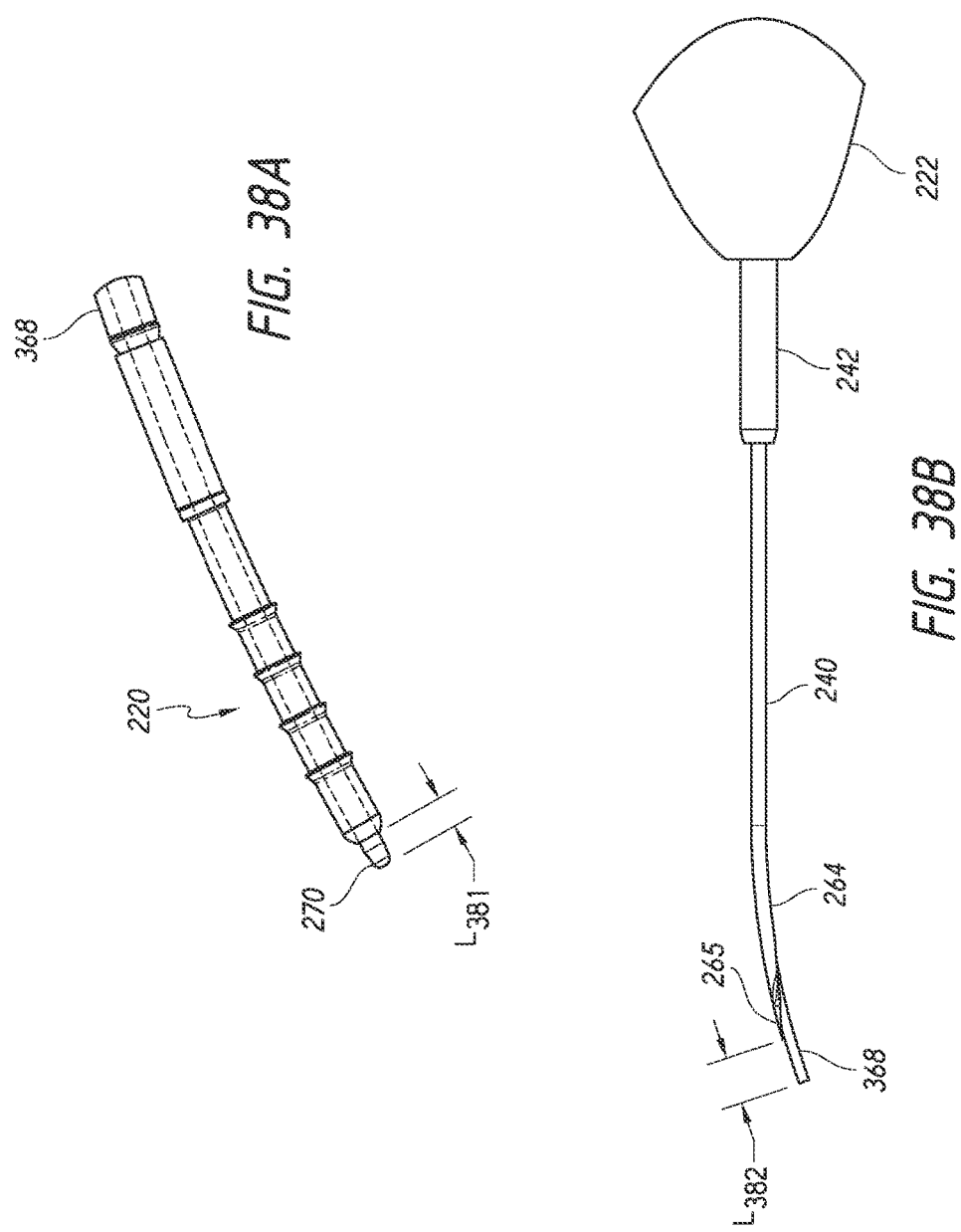
FIGS. 38A and 38B illustrate an implant loaded on the obturator, trocar, of the delivery device of FIG. 23 and a distal end of the delivery device of FIG. 23, respectively, in accordance with certain embodiments.

FIG. 37 is a detailed view illustrating the attachment or mating between the trocar assembly 228 and the trocar trigger 230 and the attachment or mating between the pusher tube device 328 and the pusher tube trigger 330, in particular, the trocar device collar portion 247 engages and is received within the trocar trigger recessed portion 271 and the pusher tube collar portion 347 engages and is received within the pusher tube trigger recessed portion 371, thereby operatively coupling the trocar 244 with its trigger 230 and the pusher tube 344 with its trigger 330.

FIGS. 38A and 38B illustrate certain non-limiting dimensions based on the positions of the trocar trigger 230 and the pusher tube trigger 330 in connection with, in some embodiments, the ocular implant 220. In FIG. 38A, which also shows the implant 220 loaded, both the trocar and pusher tube triggers and are in the forward position, and in a non-limiting embodiment the length $L_{381}$ is about 0.002 inches. In FIG. 38B, the pusher tube trigger 330 is in a generally fully forward position, and in some embodiments locked, as needed or desired, and the trocar trigger 230 is retracted, and in a non-limiting embodiment the length $L_{382}$ is about 0.064 inches.

The delivery device 210 generally comprises, but is not limited to, materials composed of stainless steel, molded plastic and nitinol, among others and equivalents thereof.

Methods of Implant Delivery Through Device-Formed Corneal Incision

FIGS. 39-44 illustrate steps or acts of a surgical procedure or method of implanting the ocular implant 220 in the suprachoroidal space 34 of the eye 10 using the implant delivery or inserter system or device 210 in accordance with some embodiments. Given the details in the figures the surgical method should be self-explanatory, however some textual description is provided below, (Briefly, and in accordance with some embodiments: in FIG. 39 both the triggers 230 and 330 are in a rear position; in FIG. 40 both the triggers 230 and 330 are in a forward position; in FIG. 41 both the triggers 230 and 330 are still or maintained in a generally forward position; in FIG. 42 both the triggers 230 and 330 are still or maintained in a generally forward position; in FIG. 43 the trocar trigger 230 is retracted and/or in a rear position while the pusher tube trigger 330 is in a locked position; and in FIG. 44 the trocar trigger 230 remains in its rear position.)

In some embodiments, a surgical microscope and the patient are positioned to provide a substantially clear visualization of the trabecular meshwork through a gonioprism on the nasal side of the eye. The patient's head can be tilted as far as practical from the surgeon, and the microscope can be tilted toward the surgeon to ensure a proper viewing angle.

The delivery device 210 is removed from its package. The protective cover tube 224 is carefully removed from the insertion needle and the safety member 232 holding the triggers is removed by the operator taking care that the triggers 230 and 330 are maintained in the rear position.

If a gonioprism is used, the gonioprism is placed on the cornea, and the anterior chamber angle is inspected using the gonioprism to ensure a good visualization at the nasal implant location. The gonioprism is then removed. Other visualization devices may be used or the procedure may be performed without use of a visualization device.

Figure 39:
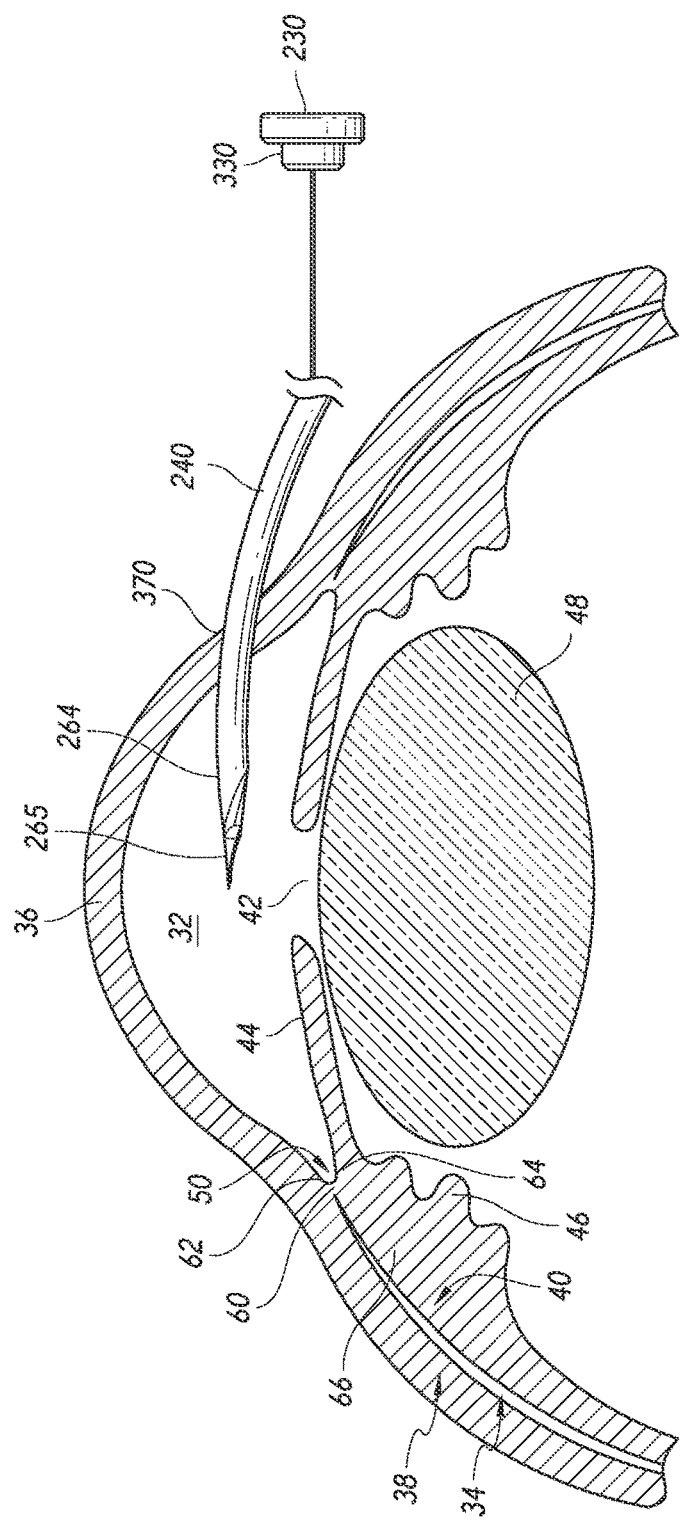

FIG. 39 illustrates formation of a self-sealing incision 370 by the insertion or corneal penetration needle 240, and more particularly, the cutting distal end tip 265 of the needle 240 of the delivery device 210, such that a portion of the needle 240 extends into the anterior chamber 32. At this stage, both the trocar trigger 230 and the pusher tube trigger 330 are maintained in the rear position by the operator, in some embodiments, a temporal clear corneal incision is made using a sharp cutting tip of the device. If a clear corneal incision has already been made, a cohesive viscoelastic may be used to maintain the anterior chamber before passing the needle 240 through the incision.

Figure 40:
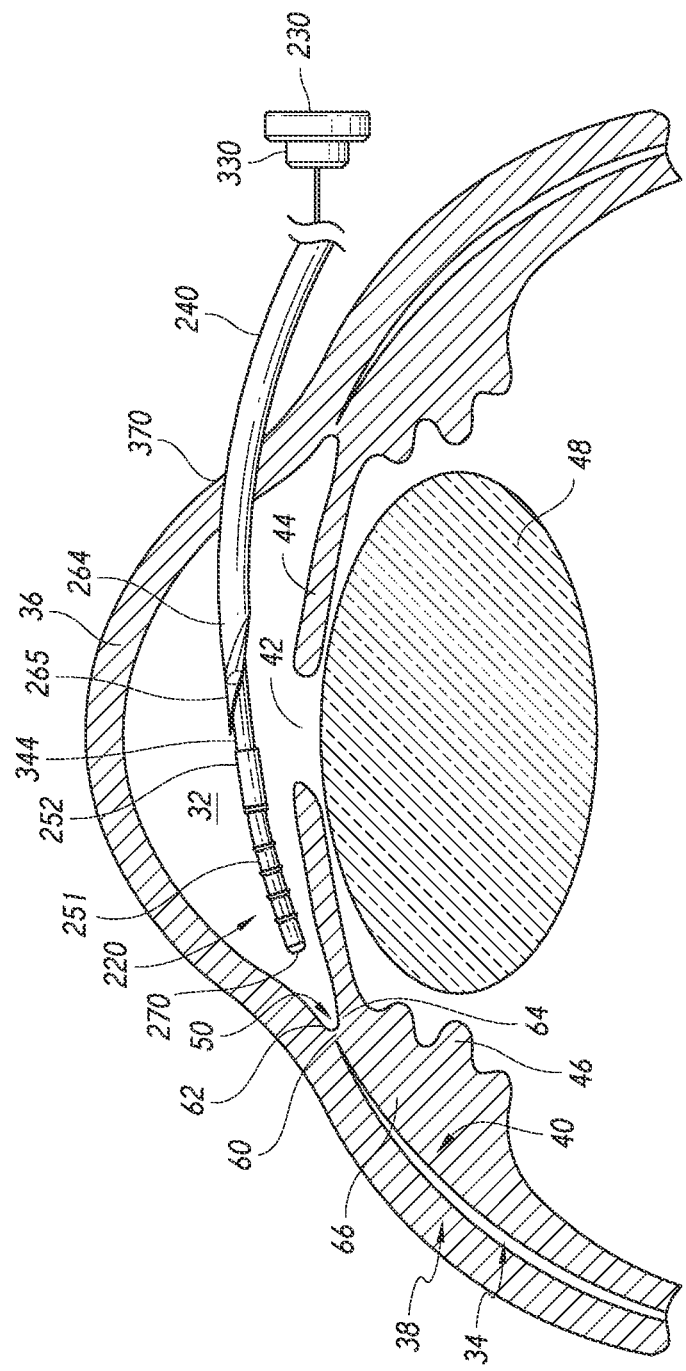

FIG. 40 illustrates forward deployment of the triggers such that the implant 220 is exposed and advanced within the anterior chamber 32 along with the trocar 244 such that the trocar distal end tip 270 extends by a predetermined distance beyond the implant 220. In some embodiments, once the insertion needle enters the eye and is past the pupillary margin, the trocar trigger (and as such the pusher tube trigger 330) are advanced to the fully forward position, thereby exposing the implant or stent 220 and the trocar tip 270.)

Figure 41:
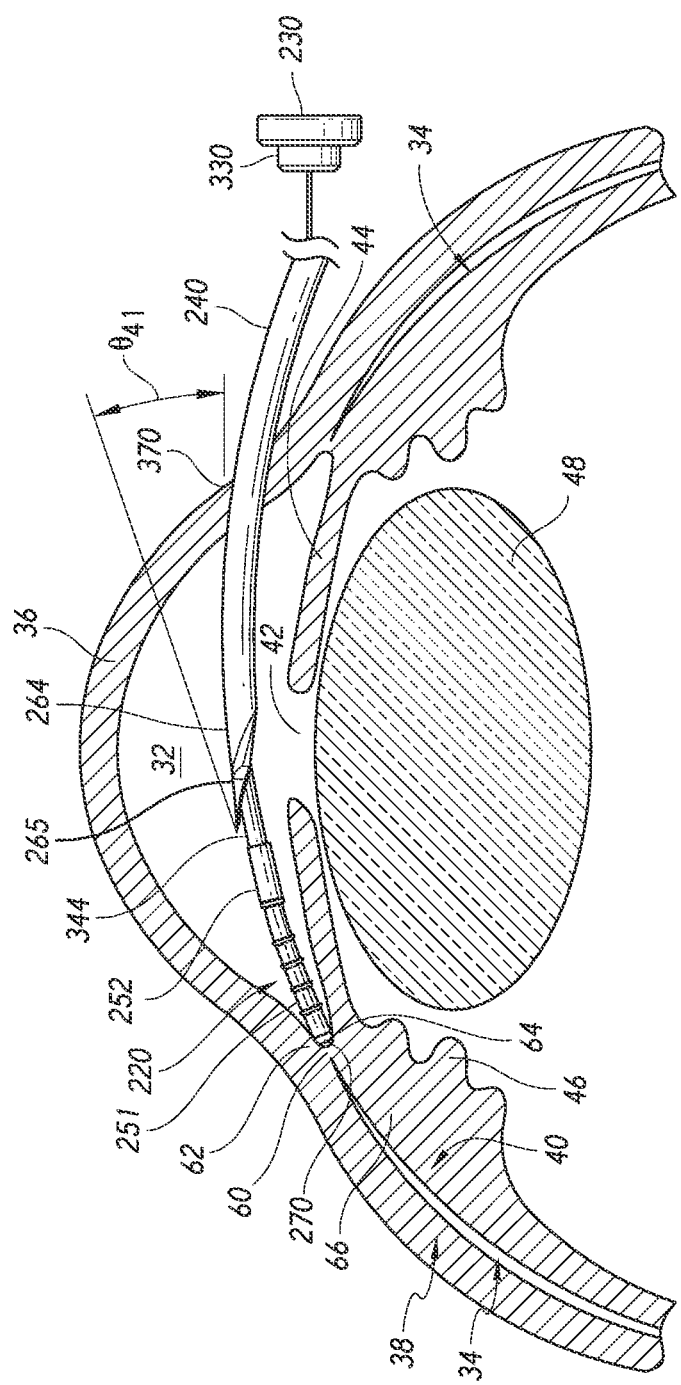

As illustrated in FIG. 41, the implant 220 is advanced across the anterior chamber 32 and positioned at the implantation site with the trocar distal end 270 adjacent the fibrous attachment zone 60. At this stage, both triggers are maintained in the forward position by the operator, with the pusher tube trigger 330 desirably locked in position so that the implant 220 cannot be proximally displaced. The angle of attack $\theta_{41}$ is about 15° (degrees), though 10, 11, 12, 13, 14, 15, 16, 17, 18, 19 and 20° (degrees) or other attack angles may efficaciously be utilized, as needed or desired. In some embodiments, a gonioprism is placed on the cornea, and the trocar/implant are guided across the anterior chamber to the nasal angle. Care is taken to avoid contact with the lens, cornea and iris. The trocar/implant may be advanced to the anterior chamber angle just posterior to the scleral spur. In some embodiments, the delivery device 210 has a built-in configuration or design for a generally downward angle of about 15° (±5°-10°) (degrees) at a site of implantation or towards the site of implantation.

Figure 42:
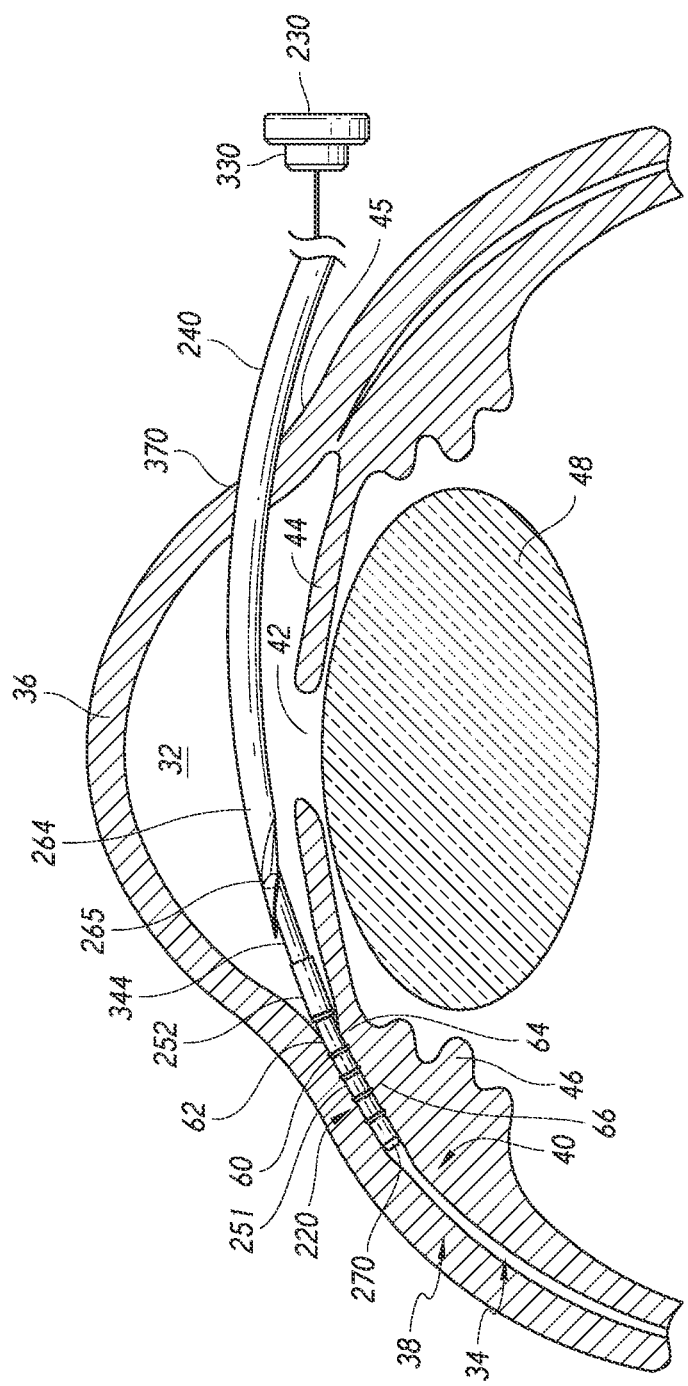

Next, as illustrated in FIG. 42, the trocar distal tip or end 270 penetrates through the tissue of and/or adjacent the fibrous attachment zone 60 and the implant 220 is advanced until its implantation position has been reached in the suprachoroidal space 34 with a predetermined portion of the implant sleeve 252 extending into the anterior chamber 32. The trocar trigger 230 is maintained in the forward position by the operator at this stage. In some embodiments, a generally narrow passage is created into the suprachoroidal space by gently separating the iris processes away from the scleral spur with the tip of the insertion trocar until the anterior and posterior portions of the scleral spur are substantially fully visible on a limited area e.g., create an approximately 0.5 mm to a maximum of about 1 mm width opening. The trocar/implant are continued to be advanced along the posterior margin of the scleral spur. With finger or thumb holding the rear/trocar trigger in the forward position, the trocar/implant are carefully advanced into the suprachoroidal space until the implant proximal sleeve just passes the scleral spur and enters the suprachoroidal space in some embodiments, approximately half (or about 0.4 mm to about 0.7 mm) of the implant sleeve remains in the anterior chamber.

In accordance with several embodiments, during implantation or insertion of the implant 220 the trocar, or obturator, 244 extends through the implant or stent lumen 154 to advantageously prevent tissue ingress and lumen clogging during implant insertion (prior to removal of the trocar, or obturator, 244 from the implant lumen 154).

Figure 43:
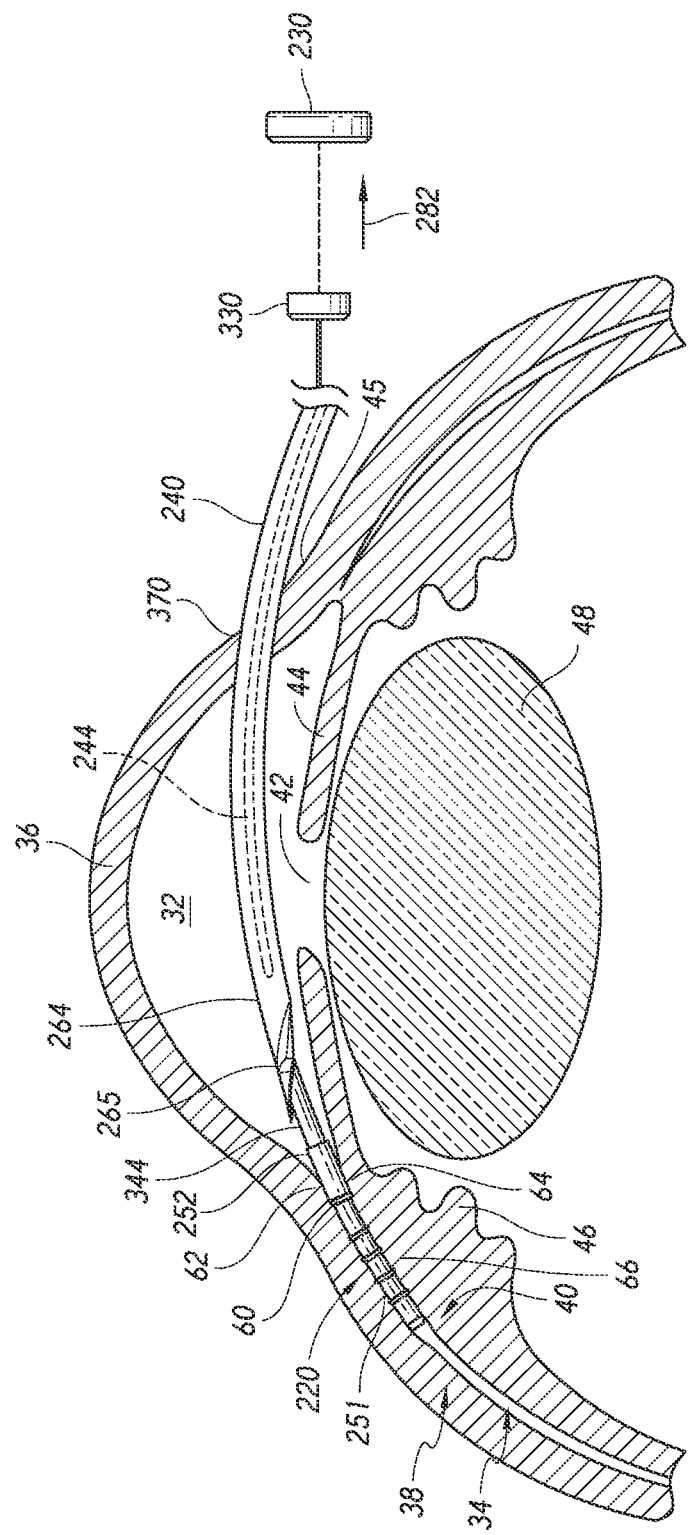

Next, as illustrated in FIG. 43, the trocar trigger 230 is moved in a rear or proximal direction 282 by the operator so that the trocar 244 is retracted from the implant lumen and the suprachoroidal space 34. In some embodiments, once the implant or stent 220 is in position at the proper depth, the trocar trigger button is slid backwards until the implant or stent 220 is released. The backwards movement of the trocar trigger 230 may advantageously prevent or inhibit over-insertion of the implant 220. In some embodiments, a backing tube is configured to react against a proximal end of the implant 220 during removal of the trocar 244.

Figure 44:
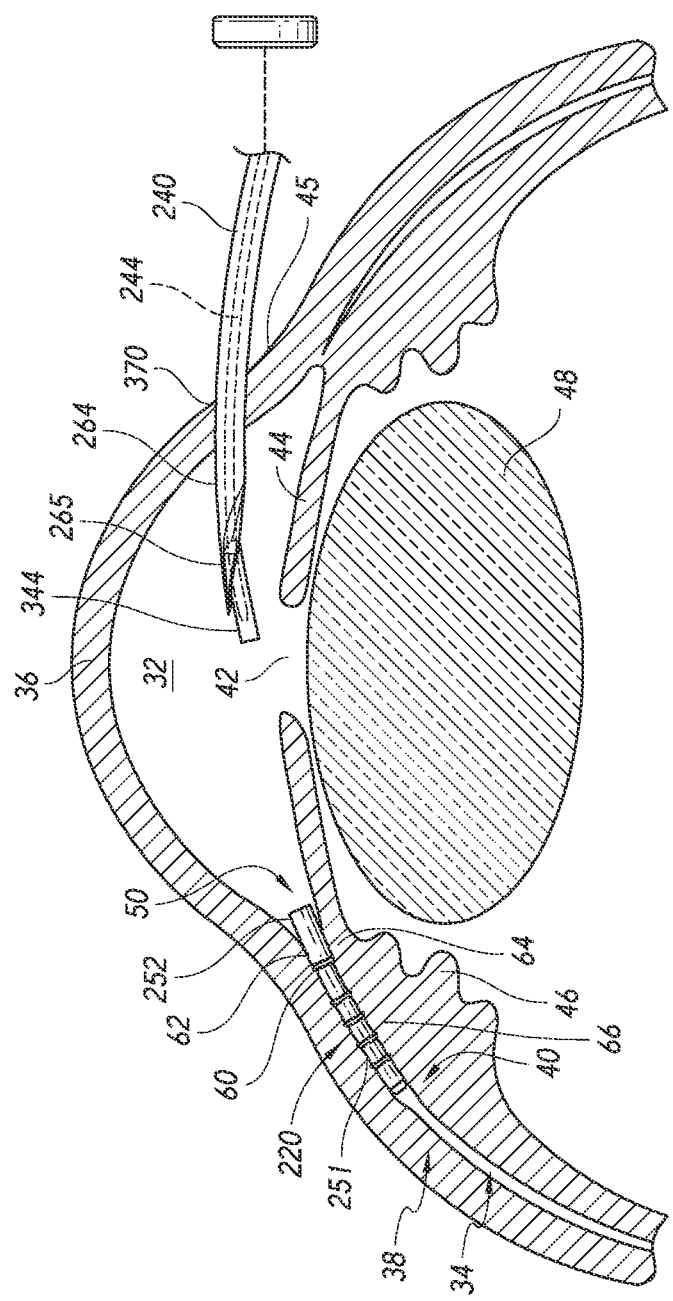

As illustrated in FIG. 44, the delivery device 210 is retracted and the insertion needle 240 is removed from the anterior chamber 32 with the implant 220 remaining within the eye 10 and implanted in the suprachoroidal space 34. In some embodiments, the incision 270 desirably self-seals to facilitate quick recovery without requiring sutures.

In some embodiments, the operator confirms that the implant is in a proper position (e.g., the proximal end rests in the anterior chamber with an unobstructed inlet) using the operating microscope and gonioprism. The anterior chamber can be irrigated and aspirated with balanced salt solution (BSS) to remove all viscoelastic, if used, if needed, the posterior edge of the incision is pressed down to facilitate substantially complete removal of the viscoelastic, if used. The anterior chamber can then be inflated with saline solution to achieve physiologic pressure, as required.

In some embodiments, a predetermined curvature of both (or at least one of) the implant or stent 220 and delivery device 210 is provided to desirably keep pressure on the sclera during implantation and prevent "understeer" or choroid penetration. The delivery device 210 can be curved to maintain the implant or stent 220 at the same curvature during the shelf life which desirably prevents plastic creep and thus maintain the implant's or stent's curvature specification. In one non-limiting embodiment, the curvature is larger than a diameter of the eye (e.g., larger than a 1 inch diameter) order to maintain the pressure on the sclera.

In some embodiments, the pusher tube 344 is configured to react against a proximal end of the implant or stent 220 during trocar or obturator removal. Advantageously, the "lazy" curve or curvature of the needle 240 and/or substantially the entire system 210 (see, e.g., FIGS. 39 to 44) maintains, in accordance with some embodiments, about a 15° angle at the implantation site, though 10, 11, 12, 13, 14, 15, 17, 18, 19 and 20° (degrees) or other angles may efficaciously be utilized, as needed or desired.

Moreover, in accordance with some embodiments, the needle 240 advantageously traverses across the eye (finite height anterior chamber clearance) without contacting the iris or cornea. In some embodiments, the implant or stent 220 is maintained at its specified, predetermined or required or desired curvature throughout substantially its shelf life, for example, to prevent plastic creep.

Drugs and Therapeutic Agents

In some embodiments, the implants disclosed herein can provide for delivery of a therapeutic agent or drug. The therapeutic agent can be, for example, an intraocular pressure-lowering drug. In some embodiments, the therapeutic agent or drug is introduced concurrently with the delivery of the shunt to the eye. The therapeutic agent or drug can be part of the implant itself. For example, the therapeutic agent or drug can be embedded in the material of the shunt, or coat at least a portion of the implant. The therapeutic agent or drug may be present on various portions of the implant. For example, the therapeutic agent or drug may be present on the distal end of the implant, or the proximal end of the implant. The implant can include combination of therapeutic agents or drugs. The different therapeutic agents or drugs can be separated or combined. One kind of therapeutic agent or drug can be present at the proximal end of the implant, and a different kind of therapeutic agent or drug can be present at the distal end of the implant. For example, an anti-proliferative agent may be present at the distal end of the implant to prevent growth, and a growth-promoting agent may be applied to the proximal end of the implant to promote growth.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect (additional non-limiting examples of such anti-VEGF compounds are described in Appendix A, which is attached herewith and made a part of this application); classes of known ophthalmic drugs, including: glaucoma agents, such as adrenergic antagonists, including for example, beta-blocker agents such as atenolol, propranolol, metipranolot betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluorometholone, loteprednol, medrysone, fluocinolone acetonide, triamcinolone acetonide, triamcinolone, beclomethasone, budesonide, flunisolide, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof, transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as ginkgo biloba; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonsists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves demyelination) such as glatimir; myelin inhibitors such as anti-NgR Blocking Protein, NgR(310) ecto-Fc; other immune modulators such as FK506 binding proteins FKBP51); and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and Valdecoxib; other immune-modulating agents such as aldesleukin, adalimumab (HUMIRA®), azathioprine, basiliximab daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; antiparasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or antiherpetic agents such as acyclovir, cidofovir, famciclovir, gangciclovir, valacyclovir, valganciclovir vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; antiplatelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

In some embodiments, the therapeutic agent is delivered through the implant to the desired location in the eye, such as the suprachoroidal space of the uveoscleral outflow pathway. In some embodiments, the therapeutic agent is delivered to the suprachoroidal space of the uveoscleral outflow pathway in combination with a therapeutic agent delivered via trans pars plana vitrectomy, thereby delivering a therapeutic agent to both sides of the retina. In some embodiments, the implant can improve access of topical medication to the posterior uvea. In some embodiments, the implant is used to deliver a topical medication to treat a chorio-retinal disease.

In some embodiments, the delivery device 110 provides implantation through a preformed or prior conical incision while the delivery device 210 does so through a self-created and self-sealing incision such that a "closed chamber" operation is performed.

The delivery device 110 is configured, in some embodiments, so that the implant is supported on a trocar wire or obturator in an exposed configuration. In some embodiments, the delivery device 210 supports the implant on a trocar wire or obturator within an insertion or corneal penetration needle.

In some embodiments, the delivery device 110 comprises a silicone retainer to hold the implant in place during travel. The delivery device 210, in some embodiments, incorporates a curved delivery system that provides adequate side loads and friction to hold the implant in place during travel and shipping.

The delivery device 110, in certain embodiments, employs a single trigger operation to release the implant. The delivery device 210, in accordance with some embodiments, utilizes a dual trigger operation to expose and release the implant trocar and implant pusher tube triggers. Once the insertion needle penetrates the cornea, both triggers advance to expose the implant or stent and the trocar and obturator. The from pusher tube trigger locks the pusher tube in a forward position, thereby preventing the implant or stent from retracting back into the needle. After implant or stent implantation, the rear trocar trigger is retracted to retract the trocar and release the implant or stent.

It should be appreciated, in accordance with some embodiments, that the disclosed implant is prevented from backward movement based advantageously on the delivery device configuration. For example, the implant 120 is prevented from backward movement because of the insertion sleeve's distal end relative dimensioning and the implant 220 is prevented from backward movement because of pusher tube's distal end relative dimensioning.

Moreover, because of the material properties of the disclosed trocars, creep during shelf life should advantageously not be an issue of concern. Also, in accordance with some embodiments, given that the implants and trocars are asymmetrically curved, this orientation as packaged, prevents any undesirable rotation of the implants with respect to the trocars even when in use. Furthermore, in accordance with some embodiments, at least the implants and trocars have predetermined curvatures which, because of their selected flexibility, can conform to the particular space or ocular location they are inserted or advanced into.

In some embodiments, the delivery device 110 is configured for use in combination with another ocular surgery, such as cataract surgery. The delivery device 110 can include a preloaded implant 120 and have a pre-curved tip. The device 110 advantageously may have an ergonomic handpiece.

In some embodiments, the delivery device 210 is configured for stand-alone, in-office surgery without being performed in conjunction with other ocular surgery (e.g., cataract surgery). The delivery device 210 can include a preloaded implant 220 and can have a pre-curved tip. Also, in some embodiments, the device 210 has integrated corneal penetration and closed chamber capability so as to perform the procedure through a self-sealing incision. The device 210 may advantageously include an ergonomic handpiece. Preloading the implant 220 on the delivery instrument 210 may reduce loading errors and contribute to ease of use.

Certain embodiments provide for the implant, trocar and/or the pusher tube to flex and allow for the implant to conform to the anatomy of the suprachoroidal space.

The delivery device geometries, such as with respect to the attack angle and curvature, can advantageously ensure proper placement of the implant in the suprachoroidal space, supraciliary space, or other anatomical space.

In some embodiments, the low friction (e.g., polyethylene on polycarbonate) trigger operation, in accordance with some embodiments, advantageously allows for smooth operation during the delivery procedures. The safety members (e.g., safety clips) may advantageously prevent undesirable trigger motion during shipment and transportation of the delivery devices.

Embodiments of the trocar or obturator material and tip shape provide several advantages which include: use of high temper stainless spring steel; pointed enough tip to pierce ciliary muscle attachment; rounded enough tip to prevent irritation/tissue damage in suprachoroidal space at sclera/choroid; material and shape allows constant force against sclera during advancement in order to assure proper placement of implant within suprachoroidal space; and trocar curvature generally matches implant or stent shape to prevent plastic creep during shelf life. Moreover, advantageously, and in accordance with some embodiments, a generally rounded, and not sharp trocar or obturator tip or distal end, e.g. 170 or 270, is utilized to glide smoothly down the sclera and prevent any undesirable sticking, scraping and attendant wound healing/fibrosis/encapsulation issues, while still being sharp enough to dissect and separate the ciliary muscle attachment in order to enter the suprachoroidal space atraumatically.

Also, in accordance with some non-limiting embodiments, the outer diameter of the stent or implant 220 is between about 300 µm and 400 µm (e.g., 350 µm, 360 µm, 375 µm, 380 µm, 390 µm), which can advantageously avoid and/or mitigate any cyclodialysis cleft issues related with implantation. For example, in some embodiments, the delivery device 210 does not create a cyclodialysis cleft substantially larger than the implant 220 itself, and in other embodiments, does not create a cyclodialysis cleft in that the delivery device 210 and implant 220 are delivered through fibrous tissue bands of the ciliary muscle as opposed to dissecting the ciliary muscle from the sclera at the anterior chamber angle.

With respect to embodiments of the delivery device 210, the curved, flared and coated stainless steel insertion or corneal penetration needle is advantageously shaped to fit anatomically within eye the and avoid iris touch. Also, the tight corneal incision can minimize fluid loss from the eye by forming a substantially closed chamber self-sealing entry. Moreover, the lowered sliding friction of the needle shaft once in the eye may advantageously prevent movement during this delicate surgery, and any resultant loss of view during any interoperative gonioscopy.

In some embodiments, and once again with respect to embodiments of the delivery device 210, the superelastic nitinol pusher tube provides backup support for the implant or stent during implantation, and allows minimal sliding force during trigger operation. Also, in accordance with some embodiments, the polyethylene protective tube prevents damage to the needle tip during shipment.

The delivery device 210, in accordance with some embodiments, can advantageously be used in a "closed chamber" procedure, which may have one or more of the following advantages: no viscoelastic is required to inflate the anterior chamber; there is minimal loss of fluid from anterior chamber (this reduces chance of hypotony); no separate blade is required to form the corneal incision; results in faster surgery; there is only one time entry into the eye; a safer procedure with less chance or lowered probability for adverse event (e.g., endophthalmitis); and less expensive and more cost effective.

The curved insertion needle, trocar or obturator and pusher tube of the delivery device 210 also, in certain embodiments allows for retention of the implant or stent shape during its entire shelf life (including during shipping) to prevent creep (such as, loss of implant or stent curvature). Moreover, the closed-chamber procedure can allow for enhanced surgical safety in a non-deepened anterior chamber by substantially matching the curvature of the cornea and allowing traversing of the eye in an ab intern procedure.

Terminology

Conditional language, for example, among others, "can," "could," "might," or "may," unless specifically stated otherwise, or otherwise understood within the context as used, is generally intended to convey that certain embodiments include, while other embodiments do not include, certain features, elements and/or steps.

Methods

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention(s). The methods disclosed herein include certain actions taken by a practitioner; however, they can also include any third-party instruction of those actions, either expressly or by implication. For example, actions such as "forming an incision" include "instructing the formation of an incision."

Ranges

The ranges disclosed herein encompass any and all overlap, subranges, and combinations thereof as well as individual numerical values within that range. For example, description of a range such as from about 5 to about 30 degrees should be considered to have specifically disclosed subranges such as from 5 to 10 degrees, from 10 to 20 degrees, from 5 to 25 degrees, from 15 to 30 degrees etc., as well as individual numbers within that range, for example, 5, 10, 15, 20, 25, 12, 15.5 and any whole and partial increments therebetween. Language such as "up to," "at least," "greater than," "less than," "between," and the like includes the number recited. Numbers preceded by a term such as "about" or "approximately" include the recited numbers. For example, "about 10%" includes "10%." For example, the terms "approximately", "about", and "substantially" as used herein represent an amount close to the stated amount that still performs a desired function or achieves a desired result.

CONCLUSION

From the foregoing description, it will be appreciated that a novel approach for intraocular pressure control has been disclosed. While the components, techniques and aspects of embodiments of the invention have been described with a certain degree of particularity, it is manifest that many changes may be made in the specific designs, constructions and methodology herein above described without departing from the spirit and scope of this disclosure.

While a number of preferred embodiments of the invention and variations thereof have been described in detail, other modifications and methods of using and medical, diagnostic, research and therapeutic applications for the same will be apparent to those of skill in the art. Accordingly, it should be understood that various applications, modifications, and substitutions may be made of equivalents without departing from the spirit of embodiments of the invention or the scope of the claims.

Various modifications and applications of the embodiments of the invention may occur to those who are skilled in the art, without departing from the true spirit or scope of the embodiments of the invention. It should be understood that the invention(s) is not limited to the embodiments set forth herein for purposes of exemplification, but is to be defined only by a fair reading of the appended claims, including the full range of equivalency to which each element thereof is entitled.

What is claimed is:

1. An ocular implant delivery system comprising:
   a delivery device comprising:
      a generally elongated outer housing that is contoured;
      an elongated insertion sleeve partially disposed in the outer housing and having a non-linear exposed distal portion extending out of a distal end of the housing, wherein the non-linear exposed distal portion has a first radius of curvature;

an obturator passing through a lumen of the insertion sleeve and having a non-linear distal portion extending beyond the non-linear distal portion of the insertion sleeve, wherein the non-linear distal portion of the obturator has a second radius of curvature that is larger than the first radius of curvature, wherein, in use, the non-linear distal portion of the obturator is adapted to provide access to a suprachoroidal space of an eye through a ciliary muscle attachment, wherein the non-linear distal portion of the obturator is flexible; and a trigger mechanically coupled to the obturator such that movement of the trigger towards a proximal end of the housing retracts the obturator within the insertion sleeve; and an implant adapted to be disposed on the non-linear portion of the obturator and positioned distally of the non-linear distal portion of the insertion sleeve prior to insertion of the delivery device into the eye, wherein, in use, a distal end of the insertion sleeve is adapted to react against a proximal end of the implant as the obturator is being retracted to release the implant.

2. The system of claim 1, wherein the insertion sleeve is sized to extend through a corneal incision and into an anterior chamber of the eye.

3. The system of claim 1, wherein the implant has a radius of curvature which substantially matches the second radius of curvature of the non-linear distal portion of the obturator.

4. The system of claim 3, wherein the second radius of curvature of the non-linear distal portion of the obturator and the radius of curvature of the implant are larger than a curvature of the eye.

5. The system of claim 1, wherein, in use, the trigger is manually controlled and held in a forward position, and retracted in a backward motion to cause release of the implant once a distal end of the implant has been advanced to a desired location within the suprachoroidal space, wherein the backward motion of the obturator is adapted to prevent against over-insertion of the implant within the suprachoroidal space.

6. The system of claim 1, wherein a distal tip of the obturator is rounded so as not to cause scraping of the sclera while still being adapted to provide access to the suprachoroidal space through the ciliary muscle attachment.

7. The system of claim 1, wherein the implant is an elongate tube, and wherein an outer diameter of the implant is between 300 and 400 microns.

8. The system of claim 1, wherein a distal portion of the implant includes a plurality of circumferential retention members.

9. The system of claim 1, wherein a distal tip of the implant is tapered and wherein a proximal end of the implant includes a flange.

10. The system of claim 1, wherein the delivery device further comprises reuse prevention structures adapted to prevent reuse of the delivery device.

11. The system of claim 10, wherein the reuse prevention structures comprise a pair of glue blocks mounted on each side of the trigger and adapted to melt upon sterilization to lock the trigger against further use.

12. The system of claim 1, wherein the implant is provided in a kit with the implant preloaded on the obturator.

13. The system of claim 1, wherein in use, the trigger is manually controlled and held in a forward position during implantation, and then retracted in a backward motion to cause release of the implant once the implant has been advanced to a desired location within the suprachoroidal space.

14. The system of claim 1, wherein a body of the implant includes a plurality of circumferential retention members.

15. The system of claim 1, wherein a distal tip of the implant is rounded or beveled and wherein a proximal end of the implant includes a flange.

16. The system of claim 1, wherein the first radius of curvature of the elongated insertion sleeve is configured to provide proper alignment of the obturator for suprachoroidal implantation of the implant.

17. The system of claim 1, wherein the second radius of curvature of the non-linear distal portion of the obturator is sized to maintain pressure against a sclera of the eye during insertion into the suprachoroidal space.

18. An ocular implant delivery device, comprising:

a generally elongated outer housing that is contoured;

an elongated insertion sleeve partially disposed in the outer housing and having a non-linear exposed distal portion that has a first radius of curvature;

a tubular support member surrounding a portion of the elongated insertion sleeve, the tubular support member having a proximal end within the outer housing and a distal end extending outside of the outer housing, wherein the tubular support member is configured to facilitate coupling of the elongated insertion sleeve to the outer housing, and wherein the tubular support member surrounds a portion of the elongated insertion sleeve;

an obturator passing through a lumen of the elongated insertion sleeve and having a non-linear distal portion extending beyond the non-linear exposed distal portion of the elongated insertion sleeve, wherein the non-linear distal portion of the obturator has a second radius of curvature that is larger than the first radius of curvature; and a trigger mechanically coupled to the obturator such that actuation of the trigger retracts the obturator into the insertion sleeve, thereby causing a proximal end of an implant disposed on the non-linear portion of the obturator to react against a distal end of the insertion sleeve so as to facilitate deployment of the implant from the obturator, wherein the non-linear distal portion of the obturator carrying the implant is configured to be advanced into a suprachoroidal space of an eye.

19. The system of claim 18, wherein the implant is an elongate tube, and wherein an outer diameter of the implant is between 300 and 400 microns.

20. The system of claim 18, wherein a distal portion of the implant includes a plurality of circumferential retention members.

21. The system of claim 18, wherein a distal tip of the implant is tapered and wherein a proximal end of the implant includes a flange.

22. The system of claim 18, wherein a distal tip of the implant is rounded or beveled and wherein a proximal end of the implant includes a flange.

23. The system of claim 18, wherein the implant is provided in a kit with the implant preloaded on the obturator.

24. The system of claim 18, wherein in use, the trigger is manually controlled and held in a forward position during implantation, and then retracted in a backward motion to cause release of the implant once the implant has been advanced to a desired location within the suprachoroidal space.

25. The system of claim 18, wherein the curvature of the non-linear distal portion of the obturator is configured to be larger than a curvature of the eye.

* * * * *